United States Patent
Angibaud et al.

(10) Patent No.: US 7,053,105 B2
(45) Date of Patent: May 30, 2006

(54) FARNESYL TRANSFERASE INHIBITING QUINOLINE AND QUINAZOLINE DERIVATIVES AS FARNESYL TRANSFERASE INHIBITORS

(75) Inventors: Patrick René Angibaud, Fontaine-Bellenger (FR); Marc Gaston Venet, Le Mesnil-Esnard (FR); Isabelle Noëlle Constance Pilatte, Louviers (FR)

(73) Assignee: Janssen Pharmaceutica, N.V., Beerse (BE)

( * ) Notice: Subject to any disclaimer, the term of this patent is extended or adjusted under 35 U.S.C. 154(b) by 106 days.

(21) Appl. No.: 10/381,363

(22) PCT Filed: Sep. 18, 2001

(86) PCT No.: PCT/EP01/10867

§ 371 (c)(1), (2), (4) Date: Mar. 24, 2003

(87) PCT Pub. No.: WO02/24682

PCT Pub. Date: Mar. 28, 2002

(65) Prior Publication Data

US 2003/0203904 A1 Oct. 30, 2003

(30) Foreign Application Priority Data

Sep. 25, 2000 (EP) .................. 00203365

(51) Int. Cl.
*A61K 31/47* (2006.01)
*C07D 215/38* (2006.01)
*C07D 215/20* (2006.01)

(52) U.S. Cl. ............. 514/313; 514/314; 514/311; 546/159; 546/169; 546/173; 546/168; 546/170

(58) Field of Classification Search .......... 514/313, 514/314, 311; 546/159, 169, 173, 168, 170
See application file for complete search history.

(56) References Cited

U.S. PATENT DOCUMENTS 6,458,800 B1 * 10/2002 Angibaud et al. .......... 514/267
6,596,735 B1 * 7/2003 Yang ......................... 514/313

FOREIGN PATENT DOCUMENTS

| EP | 0371564 B1 | 6/1990 |
|---|---|---|
| EP | 1106612 A1 | 6/2001 |
| WO | WO 97/16443 A2 | 5/1997 |
| WO | WO 97/21701 A1 | 6/1997 |
| WO | WO 98/40383 A1 | 9/1998 |
| WO | WO 98/49157 A1 | 11/1998 |
| WO | WO 98/55124 A1 | 12/1998 |
| WO | WO 00/01386 A1 | 1/2000 |
| WO | WO 00/01411 A1 | 1/2000 |
| WO | WO 00/12498 A1 | 3/2000 |
| WO | WO 00/12499 A1 | 3/2000 |
| WO | WO 00/39082 A2 | 7/2000 |
| WO | WO 2000039082 * | 7/2000 |
| WO | WO 00/47574 A1 | 8/2000 |

OTHER PUBLICATIONS

Kohl et al., "Selective Inhibition of ras-Dependent Transformation by a Farnesyttransferase Inhibitor," *Science*, 1993, pp. 1934–1937, vol. 260, No. 5116.

Rak et al., "Mutant ras Oncogenes Upregulate VEGF/VPF Expression: Implications for Induction and Inhibition of Tumor Angiogenesis." *Cancer Research*, 1995, pp. 4575–4580, vol. 55, No. 20.

* cited by examiner

*Primary Examiner*—D. Margaret Seaman

(57) ABSTRACT

This invention comprises the novel compounds of formula (I) wherein r, s, t, $Y^1$—$Y^2$, $R^1$, $R^2$, $R^3$, $R^4$, $R^5$ and $R^7$ have defined meanings, having farnesyl transferase inhibiting activity; their preparation, compositions containing them and their use as a medicine.

19 Claims, No Drawings

FARNESYL TRANSFERASE INHIBITING QUINOLINE AND QUINAZOLINE DERIVATIVES AS FARNESYL TRANSFERASE INHIBITORS

CROSS REFERENCE TO RELATED APPLICATIONS

This application is the national stage of Application No. PCT/EP01/10867, filed Sep. 18, 2001 which application claims priority from EP 00203365.2 filed Sep. 25, 2000.

The present invention is concerned with novel 2-substituted quinoline and quinazoline derivatives, the preparation thereof, pharmaceutical compositions comprising said novel compounds and the use of these compounds as a medicine as well as methods of treatment by administering said compounds.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer. A particular group of oncogenes is known as ras which have been identified in mammals, birds, insects, mollusks, plants, fungi and yeasts. The family of mammalian ras oncogenes consists of three major members ("isoforms"): H-ras, K-ras and N-ras oncogenes. These ras oncogenes code for highly related proteins generically known as $p21^{ras}$. Once attached to plasma membranes, the mutant or oncogenic forms of $p21^{ras}$ will provide a signal for the transformation and uncontrolled growth of malignant tumor cells. To acquire this transforming potential, the precursor of the $p21^{ras}$ oncoprotein must undergo an enzymatically catalyzed farnesylation of the cysteine residue located in a carboxyl-terminal tetrapeptide. Therefore, inhibitors of the enzymes that catalyzes this modification, i.e. farnesyl transferase, will prevent the membrane attachment of $p21^{ras}$ and block the aberrant growth of ras-transformed tumors. Hence, it is generally accepted in the art that farnesyl transferase inhibitors can be very useful as anticancer agents for tumors in which ras contributes to transformation.

Since mutated oncogenic forms of ras are frequently found in many human cancers, most notably in more than 50% of colon and pancreatic carcinomas (Kohl et al., Science, vol 260, 1834–1837, 1993), it has been suggested that farnesyl tranferase inhibitors can be very useful against these types of cancer.

In EP-0,371,564 there are described (1H-azol-1-ylmethyl) substituted quinoline and quinolinone derivatives which suppress the plasma elimination of retinoic acids. Some of these compounds also have the ability to inhibit the formation of androgens from progestines and/or inhibit the action of the aromatase enzyme complex.

In International Patent Specifications WO 97/16443, WO 97/21701, WO 98/40383 and WO 98/49157, there are described 2-quinolone derivatives which exhibit farnesyl transferase inhibiting activity. International Patent Specification WO 00/39082 describes a class of novel 1,2-annelated quinoline compounds, bearing a nitrogen- or carbon-linked imidazole, which show farnesyl protein transferase and geranylgeranyl transferase inhibiting activity. Certain 2-substituted quinoline compounds, including certain 2-amino, 2-methyl, 2-aldehyde and 2-chloro compounds, are also described but only as intermediates for the preparation of the annelated compounds. Various 2-substituted quinoline derivatives are also described in EP 1106612. Other quinolone compounds having farnesyl transferase inhibiting activity are described in WO 00/12498, 00/12499 and 00/47574.

Unexpectedly, it has been found that the present novel 2-substituted quinoline and quinazoline compounds show farnesyl protein transferase inhibiting activity.

The present invention concerns compounds of formula (I):

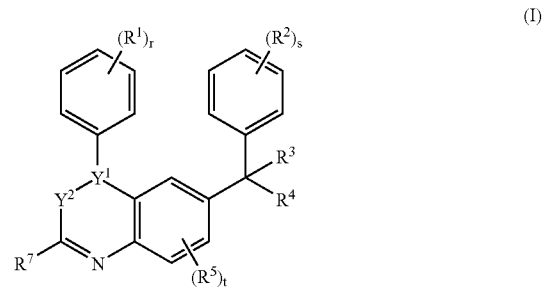

or a pharmaceutically acceptable salt or N-oxide or stereochemically isomeric form thereof, wherein r and s are each independently 0, 1, 2, 3, 4 or 5;

t is 0, 1, 2 or 3;

$>Y^1—Y^2—$ is a trivalent radical of formula

  (y-1)

  (y-2)

wherein $R^9$ is hydrogen, halo, cyano, $C_{1-6}$alkyl, hydroxy$C_{1-6}$alkyl, $C_{1-6}$alkyloxy$C_{1-6}$alkyl, —$(CR^{20}R^{21})_p$—$C_{3-10}$cycloalkyl, $C_{2-6}$alkenyl, $C_{2-6}$alkynyl, $C_{1-6}$alkyloxy, halocarbonyl, hydroxycarbonyl, $C_{1-6}$alyloxycarbonyl, aryl or a group of formula —$NR^{22}R^{23}$, —$C_{1-6}$alkyl-$NR^{22}R^{23}$, —$C_{2-6}$alkenyl-$NR^{22}R^{23}$, —$CONR^{22}R^{23}$ or —$NR^{22}$—$C_{1-6}$alkyl-$NR^{22}R^{23}$;

p is 0 to 5;

$R^{20}$ and $R^{21}$ are independently hydrogen or $C_{1-6}$ alkyl and are independently defined for each iteration of p in excess of 1;

$R^{22}$ and $R^{23}$ are independently hydrogen, $C_{1-6}$ alkyl or —$(CR^{20}R^{21})_p$—$C_{3-10}$cycloalkyl, or together with the adjacent nitrogen atom form a 5- or 6-membered heterocyclic ring optionally containing one, two or three further heteroatoms selected from oxygen, nitrogen or sulphur and optionally substituted by one or two substituents each independently selected from halo, hydroxy, cyano, nitro, $C_{1-6}$alkyl, halo$C_{1-6}$alkyl, $C_{1-6}$alkyloxy, $OCF_3$, hydroxycarbonyl, $C_{1-6}$alkyloxycarbonyl, aminocarbonyl, mono- or di-($C_{1-6}$alkyl)aminocarbonyl, amino, mono- or di($C_{1-6}$alkyl)amino, $C_{1-6}$alkylsulfonylamino, oxime, or phenyl;

each $R^1$ and $R^2$ are independently azido, hydroxy, halo, cyano, nitro, $C_{1-6}$alkyl, —$(CR^{20}R^{21})_p$—$C_{3-10}$cycloalkyl, cyano$C_{1-6}$alkyl, hydroxy$C_{1-6}$alkyl, $C_{1-6}$alkyloxy$C_{1-6}$alkyl, hydroxycarbonyl$C_{1-6}$alkyloxy$C_{1-6}$alkyl, $R^{24}S$ $C_{1-6}$alkyl, trihalomethyl, aryl$C_{1-6}$alkyl, $Het^2C_{1-6}$alkyl, —$C_{1-6}$alkyl-$NR^{22}R^{23}$, —$C_{1-6}$alkylN$R^{22}C_{1-6}$alkyl-$NR^{22}R^{23}$, —$C_{1-6}$alkylN$R^{22}COC_{1-6}$alkyl, —$C_{1-6}$alkylN$R^{22}COAlkAr^2$, —$C_{1-6}$alkylN$R^{22}COAr^2$, $C_{1-6}$alkylsulphonylamino$C_{1-6}$alkyl, $C_{1-6}$alkyloxy, hydroxyC$_{1-6}$alkyloxy, C$_{1-6}$alkyloxyC$_{1-6}$alkyloxy, —OC$_{1-6}$alkyl-NR$^{22}$R$^{23}$, trihalomethoxy, arylC$_{1-6}$ alkyloxy, Het$^2$C$_{1-6}$alkyloxy, C$_{1-6}$alkylthio, C$_{2-6}$alkenyl, cyanoC$_{2-6}$alkenyl, —C$_{2-6}$alkenyl-NR$^{22}$R$^{23}$, hydroxycarbonylC$_{2-6}$alkenyl, C$_{1-6}$alkyloxycarbonylC$_{2-6}$alkenyl, C$_{2-6}$alkynyl, —CHO, C$_{1-6}$alkylcarbonyl, hydroxyC$_{1-6}$alkylcarbonyl, hydroxycarbonyl, C$_{1-6}$alkyloxycarbonyl, —CONR$^{22}$R$^{23}$, —CONR$^{22}$—C$_{1-6}$alkyl-NR$^{22}$R$^{23}$, —CONR$^{22}$—C$_{1-6}$alkyl-Het$^2$, —CONR$^{22}$—C$_{1-6}$alkyl-Ar$^2$, —CONR$^{22}$—O—C$_{1-6}$alkyl, —CONR$^{22}$—C$_{1-6}$alkenyl, —NR$^{22}$R$^{23}$, —OC(O)R$^{24}$, —CR$^{24}$=NR$^{25}$, —CR$^{24}$=N—OR$^{25}$, —NR$^{24}$C(O)NR$^{22}$R$^{23}$, —NR$^{24}$SO$_2$R$^{25}$, —NR$^{24}$C(O)R$^{25}$, —S(O)$_{0-2}$R$^{24}$, —SO$_2$NR$^{24}$R$^{25}$, —C(NR$^{26}$R$^{27}$)=NR$^{28}$; —Sn(R$^{24}$)$_3$, —SiR$^{24}$R$^{24}$R$^{25}$, —B(OR$^{24}$)$_2$, —P(O)OR$^{24}$OR$^{25}$, aryloxy, Het$^2$-oxy, or a group of formula —Z, —CO—Z or —CO—NR$^y$—Z in which R$^y$ is hydrogen or C$_{1-4}$alkyl and Z is phenyl or a 5- or 6-membered heterocyclic ring containing one or more heteroatoms selected from oxygen, sulphur and nitrogen, the phenyl or heterocyclic ring being optionally substituted by one or two substituents each independently selected from halo, cyano, hydroxycarbonyl, aminocarbonyl, C$_{1-6}$alkylthio, hydroxy, —NR$^{22}$R$^{23}$, C$_{1-6}$-alkylsulphonylamino, C$_{1-6}$alkyl, haloC$_{1-6}$alkyl, C$_{1-6}$alkyloxy or phenyl; or two R$^1$ and R$^2$ substituents adjacent to one another on the phenyl ring may independently form together a bivalent radical of formula —O—CH$_2$—O— (a-1)

—O—CH$_2$—CH$_2$—O— (a-2)

—O—CH=CH— (a-3)

—O—CH$_2$—CH$_2$— (a-4)

—O—CH$_2$—CH$_2$—CH$_2$— (a-5)

—CH=CH—CH=CH— (a-6)

R$^{24}$ and R$^{25}$ are independently hydrogen, C$_{1-6}$ alkyl, —(CR$_{20}$R$_{21}$)p-C$_{3-10}$cycloalkyl or arylC$_{1-6}$alkyl;

R$^{26}$, R$^{27}$ and R$^{28}$ are independently hydrogen and C$_{1-6}$alkyl or C(O) C$_{1-6}$alkyl;

R$^3$ is hydrogen, halo, cyano, C$_{1-6}$alkyl, —(CR$^{20}$R$^{21}$)$_p$—C$_{3-10}$cycloalkyl, haloC$_{1-6}$alkyl, cyanoC$_{1-6}$alkyl, hydroxyC$_{1-6}$alkyl, C$_{1-6}$alkyloxyC$_{1-6}$alkyl, arylC$_{1-6}$alkyloxy C$_{1-6}$alkyl, C$_{1-6}$alkylthioC$_{1-6}$alkyl, hydroxycarbonylC$_{1-6}$alkyl, C$_{1-6}$alkylcarbonyl C$_{1-6}$alkyl, C$_{1-6}$alkyloxycarbonylC$_{1-6}$alkyl, —C$_{1-6}$alkyl-NR$^{22}$R$^{23}$, —C$_{1-6}$alkyl-CONR$^{22}$R$^{23}$, arylC$_{1-6}$alkyl, Het$^2$C$_{1-6}$alkyl, C$_{2-6}$alkenyl, —C$_{2-6}$alkenyl NR$^{22}$R$^{23}$, C$_{2-6}$alkynyl, hydroxycarbonyl, C$_{1-6}$alkyloxycarbonyl, aryl, or Het$^2$; or a radical of formula —O—R$^{10}$ (b-1)

—S—R$^{10}$ (b-2)

—NR$^{11}$R$^{12}$ (b-3) or

—N=CR$^{10}$R$^{11}$ (b-4)

wherein R$^{10}$ is hydrogen, C$_{1-6}$alkyl, —(CR$^{20}$R$^{21}$)$_p$—C$_{3-10}$cycloalkyl, arylC$_{1-6}$alkyl, C$_{2-6}$alkenyl, C$_{2-6}$alkynyl, C$_{1-6}$alkylcarbonyl, aryl, a group of formula —NR$^{22}$R$^{23}$R or —C$_{1-6}$alkylC(O)OC$_{1-6}$alkyl NR$^{22}$R$^{23}$, or a radical of formula -Alk-OR$^{13}$ or -Alk-NR$^{14}$R$^{15}$;

R$^{11}$ is hydrogen, C$_{1-6}$alkyl, —(CR$^{20}$R$^{21}$)$_p$—C$_{3-10}$cycloalkyl, C$_{2-6}$alkenyl, C$_{2-6}$alkynyl, aryl or arylC$_{1-6}$alkyl;

R$^{12}$ is hydrogen, hydroxy, C$_{1-6}$alkyl, —(CR$^{20}$R$^{21}$)$_p$—C$_{3-10}$cycloalkyl, C$_{1-6}$alkylcarbonylC$_{1-6}$alkyl, arylC$_{1-6}$alkyl, C$_{2-6}$alkenyl, C$_{2-6}$alkynyl, aryl, C$_{1-6}$alkyloxy, a group of formula —NR$^{22}$R$^{23}$, C$_{1-6}$alkylcarbonylamino, C$_{1-6}$alkylcarbonyl, haloC$_{1-6}$alkylcarbonyl, arylC$_{1-6}$alkylcarbonyl, arylcarbonyl, C$_{1-6}$alkyloxycarbonyl, trihaloC$_{1-6}$alkyloxycarbonyl, C$_{1-6}$alkyloxyC$_{1-6}$alkylcarbonyl, aminocarbonyl, mono- or di(C$_{1-6}$alkyl)aminocarbonyl wherein the alkyl moiety may optionally be substituted by one or more substituents independently selected from aryl and C$_{1-6}$alkyloxycarbonyl substituents; aminocarbonylcarbonyl, mono- or di(C$_{1-6}$alkyl)aminoC$_{1-6}$alkylcarbonyl, or a radical of formula -Alk-OR$^{13}$ or Alk-NR$^{14}$R$^{15}$;

wherein Alk is C$_{1-6}$alkanediyl;

R$^{13}$ is hydrogen, C$_{1-6}$alkyl, —(CR$^{20}$R$^{21}$)$_p$—C$_{3-10}$cycloalkyl, C$_{2-6}$alkenyl, C$_{2-6}$allknyl, C$_{1-6}$alkylcarbonyl, hydroxyC$_{1-6}$alkyl, aryl or arylC$_{1-6}$alkyl;

R$^{14}$ is hydrogen, C$_{1-6}$alkyl, —(CR$^{20}$R$^{21}$)$_p$—C$_{3-10}$cycloalkyl, C$_{2-6}$alkenyl, C$_{2-6}$alkynyl, aryl or arylC$_{1-6}$ alkyl;

R$^{15}$ is hydrogen, C$_{1-6}$alkyl, —(CR$^{20}$R$^{21}$)$_p$—C$_{3-10}$cycloalkyl, C$_{2-6}$alkenyl, C$_{2-6}$alkynyl, C$_{1-6}$alkylcarbonyl, aryl or arylC$_{1-6}$alkyl;

R$^4$ is a radical of formula

(c-1)

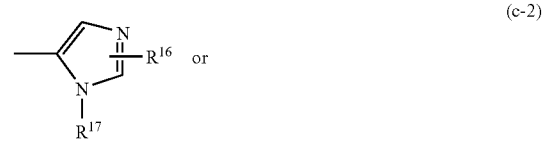
(c-2)

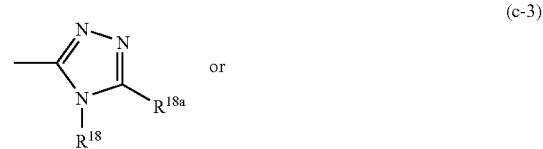
(c-3)

(c-4)

wherein R$^{16}$ is hydrogen, halo, C$_{1-6}$alkyl, —(CR$^{20}$R$^{21}$)$_p$—C$_{3-10}$cycloalkyl, hydroxyC$_{1-6}$aklyl, C$_{1-6}$alkyloxy C$_{1-6}$alkyl, C$_{1-6}$alkylS(O)$_{0-2}$C$_{1-6}$alkyl, C$_{1-6}$alkyloxy, C$_{1-6}$alkylthio, a group of formula —NR$^{22}$R$^{23}$, hydroxycarbonyl, C$_{1-6}$alkyloxycarbonyl or aryl, R$^{17}$ is hydrogen, C$_{1-6}$alkyl, —(CR$^{20}$R$^{21}$)$_p$—C$_{3-10}$cycloalkyl, hydroxyC$_{1-6}$alkyl, C$_{1-6}$alkyloxyC$_{1-6}$alkyl, aryl C$_{1-6}$alkyl, trifluoromethyl, trifluoromethylC$_{1-6}$alkyl, hydroxycarbonylC$_{1-6}$alkyl, C$_{1-6}$akyloxycarbonylC$_{1-6}$alkyl, mono- or di (C$_{1-6}$alkyl)aminosulphonyl or —C$_{1-6}$alkyl P(O)OR$^{24}$OR$^{25}$;

R$^{18}$ is hydrogen, C$_{1-6}$alkyl, —(CR$^{20}$R$^{21}$)$_p$—C$_{3-10}$cycloalkyl, arylC$_{1-6}$alkyl or C$_{1-6}$alkyloxyC$_{1-6}$alkyl;

R$^{18a}$ is hydrogen, —SH or —S C$_{1-4}$alkyl $R^5$ is cyano, hydroxy, halo, $C_{1-6}$alkyl, —$(CR^{20}R^{21})_p$—$C_{3-10}$ cycloalkyl, $C_{2-6}$alkenyl, $C_{2-6}$alkynyl, $C_{1-6}$alkyloxy, aryl$C_{1-6}$alkyloxy, Het$^2C_{1-6}$alkyloxy, hydroxycarbonyl, $C_{1-6}$alkyloxycarbonyl, or a group of formula —$NR^{22}R^{23}$ or —$CONR^{22}R^{23}$;

$R^7$ is (A) a group selected from:
- (A1) $C_{1-10}$alkyl,
- (A2) —$(CR^{20}R^{21})_p$—$C_{3-10}$cycloalkyl, $C_{2-6}$alkenyl, or $C_{2-6}$alkynyl; or
- (A3) $C_{1-6}$alkylthio, the groups (A1), (A2) and (A3) being optionally substituted by one or more substituents selected from:
- (Aa) halo, cyano, —$OR^{29}$, $COOR^{29}$, —$CONR^{22}R^{23}$, or —$NR^{22}R^{23}$; or
- (Ab) —$OAlkNR^{22}R^{23}$, —$OAlkCONR^{22}R^{23}$, —$COOAlkAr^2$, —$NR^{22}AlkNR^{22}R^{23}$, —$NR^{22}AlkCN$, —$NR^{22}Alk$-$C_{1-6}$hydroxyalkyl, —$NR^{22}AlkOC_{1-6}$alkyl, —$NR^{22}AlkCOOC_{1-6}$alkyl, —$NR^{22}AlkSAlk$-$Ar^2$, —$NR^{22}Alk$-$Ar^2$, —$NR^{22}Alk$-$Het^2$ or —$NR^{22}$ $C_{2-6}$alkenyl;

or $R^7$ is (B) a group selected from:
- (B1) —$COOR^{29}$, —$CHO$, —$COC_{1-6}$alkyl, —$CONR^{22}R^{23}$, —$NR^{22}R^{23}$ or —$NHCOC_{1-15}$alkyl; or
- (B2) halo, —$COAlkAr^2$, —$COAlkHet^2$, —$CONR^{22}(CR^{20}R^{21})_p$—$C_{3-10}$cycloalkyl, —$CONR^{22}$ $C_{2-6}$alkenyl, —$CONR^{22}$ $Ar^2$, —$CONR^{22}Het^2$, —$CONR^{22}$ $AlkNR^{22}R^{23}$, —$CONR^{22}$ $AlkAr^2$, —$CONR^{22}AlkHet^2$, —$NHCO(CR^{20}R^{21})_p$—$C_{3-10}$cycloalkyl, —$NHCO$ $C_{2-10}$alkenyl, —$NHCOAlkOC_{1-6}$alkyl, —$NHCOAlkOCOC_{1-6}$alkyl, —$NHCOAlkCOOC_{1-6}$alkyl, —$NHCOAr^2$, —$NHCOOAr^2$, —$NHCOAlkAr^2$, —$NHCOC_{2-6}$alkenyl$Ar^2$, —$NHCOAlkOAr^2$, —$NHCOAlkSAr^2$, —$NHCOHet^2$, —$NHCOAlkHet^2$, —$NHCOC_{2-6}$alkenyl$Het^2$, —$NHCOAlkOHet^2$, —$NHCOAlkSHet^2$, —$NHCONR^{22a}R^{23a}$, —$NHCSNR^{22a}R^{23a}$ in which $R^{22a}$ and $R^{23a}$ represent groups represented by $R^{22}$ and $R^{23}$ above or in addition one or two groups selected from $C_{2-6}$ alkenyl, -$AlkCOOC_{1-6}$alkyl, $Ar^2$, Het$^2$, -$AlkAr^2$, -$AlkHet^2$, or —$(CR^{20}R^{21})_p$—$C_{3-10}$cycloalkyl; and $R^{29}$ is hydrogen, $C_{1-6}$ alkyl, $Ar^2C_{1-6}$ alkyl, Het$^2C_{1-6}$ alkyl;

a group of formula —$NR^{24}SO_2R^{25}$;
a group of formula —$C(NR^{26}R^{27})$=$NR^{28}$;
a group of formula —NH—NH—$R^{40}$ in which $R^{40}$ is $Ar^2$, Het$^2$, —$C_{1-6}$alkyl$Ar^2$, —$C(O)Het^2$, —$C(O)Ar^2$, —$C(O)C_{1-6}$alkyl, —$C(O)C_{1-6}$alkyl$Ar^2$, —$C(O)$ NHAr2, —$C(S)$NHAr$^2$, —$C(S)C_{1-6}$alkyl, an oxime, $C_{1-6}$alkyl oxime or aryl $C_{1-6}$alkyl oxime group;

or $R^7$ is (C) a group of formula;
- (C1) —Z—$Ar^2$ or —Z—Het$^2$, or
- (C2) —Z—O—$Ar^2$ or —Z—S—$Ar^2$ in which Z is (Ca) a chemical bond, or a $C_{1-6}$alkanediyl or $C_{2-6}$alkenediyl group optionally substituted by hydroxy, a group of formula —$NR^{22}R^{23}$, $OR^{24}$ or cyano; or
(Cb) a carbonyl group;

$Ar^2$ is phenyl, naphthyl or phenyl or naphthyl substituted by one to five substituents each independently selected from halo, hydroxy, cyano, nitro, $C_{1-6}$alkyl, halo$C_{1-6}$alkyl, -alkyl$NR^{22}R^{23}$, $C_{1-6}$alkyloxy, $OCF_3$, hydroxycarbonyl, $C_{1-6}$alkyloxycarbonyl, —$CONR^{22}R^{23}$, —$NR^{22}R^{23}$, $C_{1-6}$alkylsulfonylamino, oxime or phenyl, or a bivalent substituent of formula —O—$CH_2$—O— or —O—$CH_2$—$CH_2$—O—;

Het$^2$ is a mono- or bi-cyclic heterocyclic ring containing one or more heteroatoms selected from oxygen, sulphur and nitrogen and optionally substituted by one or two substituents each independently selected from halo, hydroxy, cyano, nitro, $C_{1-6}$akyl, halo$C_{1-6}$alkyl, -alkyl$NR^{22}R^{23}$, $C_{1-6}$alkyloxy, $OCF_3$, hydroxycarbonyl, $C_{1-6}$alkyloxycarbonyl, —$CONR^{22}R^{23}$, —$NR^{22}R^{23}$, $C_{1-6}$alkylsulfonylamino, oxime or phenyl:

provided that (A) when r and s are each 1, t is 0, $R^1$ is 3-chloro, $R^2$ is 4-chloro, $R^3$ is hydroxy and $R^4$ is 1-methyl-1H-imidazol-5-yl, and (a) when >$Y^1$—$Y^2$ is a radical of formula (y-2), in which $R^9$ is hydrogen, then $R^7$ is not amino, methyl, —CHO or chloro, or (b) when >$Y^1$—$Y^2$ is a radical of formula (y-1), then $R^7$ is not chloro; and (B) when >$Y^1$—$Y^2$ is a radical of formula (y-2) and $R^4$ is a radical of formula (c-1), (c-2) or (c-4) then the group $R^7$ is (i) a group A1 substituted by substituents (Ab), a group (A2) substituted by substituents (Aa) (other than halo) or (Ab), or a group (A3) optionally substituted by substituents (Aa) or (Ab) as defined above; or (ii) a group (B2) as defined above; or (iii) a group(C1) in which Z is (Cb), or a group (C2) as defined above.

As used in the foregoing definitions and hereinafter, halo is generic to fluoro, chloro, bromo and iodo; $C_{1-4}$alkyl defines straight and branched chain saturated hydrocarbon radicals having from 1 to 4 carbon atoms such as, e.g. methyl, ethyl, propyl, butyl, 1-methylethyl, 2-methylpropyl and the like; $C_{1-6}$alkyl includes $C_{1-4}$alkyl and the higher homologues thereof having 5 to 6 carbon atoms such as, for example, pentyl, 2-methyl-butyl, hexyl, 2-methylpentyl and the like; $C_{1-6}$alkanediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof; halo$C_{1-6}$alkyl defines $C_{1-6}$alkyl containing one or more halo substituents for example trifluoromethyl; $C_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like. The term "S(O)" refers to a sulfoxide and "S(O)$_2$" to a sulfone. Aryl defines phenyl, naphthalenyl or phenyl substituted with one or more substituents each independently selected from halo, $C_{1-6}$alkyl, $C_{1-6}$alkyloxy or trifluoromethyl, cyano, hydroxycarbonyl.

The pharmaceutically acceptable acid addition salts as mentioned hereinabove are meant to comprise the therapeutically active non-toxic acid addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-amino-salicylic, pamoic and the like acids.

The term acid addition salts also comprises the hydrates and the solvent addition forms which the compounds of formula (I) are able to form. Examples of such forms are e.g. hydrates, alcoholates and the like.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

Whenever used hereinafter, the term "compounds of formula (I)" is meant to include also the pharmaceutically acceptable acid addition salts and all stereoisomeric forms.

In the following discussion of preferred compounds according to the invention it will be appreciated that the provisos recited above in relation to formula (I) will still apply.

Examples of compounds of formula (I) include those wherein one or more of the following restrictions apply:

r and s are each independently 0, 1 or 2;
t is 0 or 1;
$>Y^1—Y^2—$ is a trivalent radical of formula $$>C=CR^9— \quad (y\text{-}2)$$

wherein $R^9$ is hydrogen, cyano, halo, $C_{1-6}$alkyl, hydroxy$C_{1-6}$alkyl, hydroxycarbonyl or aminocarbonyl;

$R^1$ is halo, $C_{1-6}$alkyl, $—(CR^{20}R^{21})_p—C_{3-10}$cycloalkyl, trihalomethyl, trihalomethoxy, $C_{2-6}$alkenyl, hydroxycarbonyl$C_{2-6}$alkenyl, $C_{2-6}$alkynyl, $C_{1-6}$alkyloxy, hydroxy$C_{1-6}$alkyloxy, amino$C_{1-6}$alkyloxy, $C_{1-6}$alkylthio, hydroxycarbonyl, $C_{1-6}$alkyloxycarbonyl, $—CONR^{22}R^{23}$, or $—CH=NOR^{25}$; or two $R^1$ substituents adjacent to one another on the phenyl ring may independently form together a bivalent radical of formula

—O—CH$_2$—O—  (a-1)

—O—CH$_2$—CH$_2$—O—  (a-2)

$R^2$ is halo, cyano, nitro, cyano$C_{1-6}$alkyl, $—C_{1-6}$alkylNR$^{22}$R$^{23}$; cyano$C_{2-6}$alkenyl, $—NR^{22}R^{23}$, CHO, $C_{1-6}$alkyloxycarbonyl, $—CONR^{22}R^{23}$; or two $R^2$ substituents adjacent to one another on the phenyl ring may independently form together a bivalent radical of formula —O—CH$_2$—O—  (a-1)

—O—CH$_2$—CH$_2$—O—  (a-2)

$R^3$ is hydrogen, halo, $C_{1-6}$alkyl, $—(CR^{20}R^{21})_p—C_{3-10}$cycloalkyl, halo$C_{1-6}$alkyl, cyano$C_{1-6}$alkyl, hydroxy$C_{1-6}$alkyl, $C_{1-6}$alkyloxy$C_{1-6}$alkyl, $—C_{1-6}$alkylNR$^{22}$R$^{23}$, Het$^2C_{1-6}$alkyl, $—C_{2-6}$alkenylNR$^{22}$R$^{23}$, or -Het$^2$; or a group of formula —O—R$^{10}$  (b-1)

—NR$^{11}$R$^{12}$  (b-3)

wherein $R^{10}$ is hydrogen, $C_{1-6}$alkyl, or $—(CR^{20}R^{21})_p—C_{3-10}$cycloalkyl, or a group of formula -Alk-OR$^{13}$ or -Alk-NR$^{14}$R$^{15}$;

$R^{11}$ is hydrogen or $C_{1-6}$alkyl;

$R^{12}$ is hydrogen, hydroxy, $C_{1-6}$alkyl, $—(CR^{20}R^{21})_p—C_{3-10}$cycloalkyl, $C_{1-6}$alkyloxy, $C_{1-6}$alkylcarbonyl, aminocarbonyl, or a radical of formula -Alk-OR$^{13}$ or Alk-NR$^{14}$R$^{15}$;

wherein Alk is $C_{1-6}$alkanediyl;

$R^{13}$ is hydrogen, $C_{1-6}$alkyl or $—(CR^{20}R^{21})_p—C_{3-10}$cycloalkyl;

$R^{14}$ is hydrogen, $C_{1-6}$alkyl, or $—(CR^{20}R^{21})_p—C_{3-10}$cycloalkyl;

$R^{15}$ is hydrogen or $C_{1-6}$alkyl;

$R^4$ is a radical of formula (c-2) or (c-3)

wherein $R^{16}$ is hydrogen, halo or $C_{1-6}$alkyl, $R^{17}$ is hydrogen, $C_{1-6}$alkyl, $—(CR^{20}R^{21})_p—C_{3-10}$cycloalkyl, $C_{1-6}$alkyloxy-$C_{1-6}$alkyl or trifluoromethyl;

$R^{18}$ is hydrogen, $C_{1-6}$alkyl or $—(CR^{20}R^{21})_p—C_{3-10}$cycloalkyl;

$R^{18a}$ is hydrogen;

$R^5$ is cyano, halo, $C_{1-6}$alkyl, $C_{2-6}$alkynyl, $C_{1-6}$alkyloxy or $C_{1-6}$alkyloxycarbonyl;

$R^7$ is cyano, a $C_{1-10}$alkyl, $C_{2-6}$alkenyl or $C_{2-6}$ alkynyl group or a $C_{1-10}$alkyl, $C_{2-6}$alkenyl or $C_{2-6}$ alkynyl group substituted by one or more substituents selected from cyano, $—OR^{29}$, $—COOR^{25}$ and $—CONR^{22}R^{23}$, $—NR^{22}AlkNR^{22}R^{23}$, $—NR^{22}C_{2-6}$alkenyl; or a group of formula: $—COOR^{29}$, $—CONR^{22}R^{23}$, $—CONR^{22}—(CR^{20}R^{21})_p—C_{3-10}$cycloalkyl, $—CONR^{22}C_{2-6}$alkenyl, $—CONR^{22}Het^2$, $—CONR^{22}Alk-NR^{22}R^{23}$, $—NH-COC_{1-6}$alkyl, $—NHCOHet^2$ or $—NHCOAlkHet^2$ Het$^2$ is a 5- or 6-membered monocyclic heterocyclic ring containing one, two or three heteroatoms selected from oxygen, sulphur or nitrogen for example pyrrolidinyl, imidazolyl, triazolyl, pyridyl, pyrimidinyl, furyl, morpholinyl, piperazinyl, piperidinyl, thiophenyl, thiazolyl or oxazolyl, or a 9- or 10-membered bicyclic heterocyclic ring especially one in which a benzene ring is fused to a heterocyclic ring containing one, two or three heteroatoms selected from oxygen, sulphur or nitrogen for example indolyl, quinolinyl, benzimidazolyl, benzotriazolyl, benzoxazolyl, benzothiazolyl or benzodioxolanyl.

A group of interesting compounds consists of those compounds of formula (I) wherein one or more of the following restrictions apply:

$>Y^1—Y^2—$ is a trivalent radical of formula (y-2), wherein $R^9$ is hydrogen, halo, $C_{1-4}$alkyl, hydroxycarbonyl, or $C_{1-4}$alkyloxycarbonyl;

r is 0, 1 or 2;

s is 0 or 1;

t is 0;

$R^1$ is halo, $C_{1-6}$alkyl or two $R^1$ substituents ortho to one another on the phenyl ring may independently form together a bivalent radical of formula (a-1);

$R^2$ is halo, cyano, nitro, CHO, oxime, or two $R^2$ substituents ortho to one another on the phenyl ring may independently form together a bivalent radical of formula (a-1);

$R^3$ is halo, Het$^2$ or a group of formula (b-1) or (b-3) wherein $R^{10}$ is hydrogen or a group of formula -Alk-OR$^{13}$.

$R^{11}$ is hydrogen;

$R^{12}$ is hydrogen, $C_{1-6}$alkyl, $C_{1-6}$alkylcarbonyl, hydroxy, $C_{1-6}$alkyloxy or mono- or di($C_{1-6}$alkyl)amino$C_{1-6}$alkylcarbonyl;

Alk is $C_{1-6}$alkanediyl and $R^{13}$ is hydrogen;

R⁴ is a group of formula (c-2) or (c-3) wherein
  R¹⁶ is hydrogen, halo or mono- or di($C_{1-4}$alkyl)amino;
  R¹⁷ is hydrogen or $C_{1-6}$alkyl;
  R¹⁸ is hydrogen or $C_{1-6}$alkyl;
  R¹⁸ᵃ is hydrogen;
  R⁷ is cyano, a $C_{1-10}$alkyl group or a $C_{1-10}$alkyl group substituted by amino, —NR²²AlkNR²²R²³ or —NR²²$C_{2-6}$alkenyl; or R⁷ is $C_{2-6}$alkenyl, COOR²⁹, —CONR²²R²³, —CONR²²Het², —CONR²²$C_{1-6}$alkyl Het², —CONR²²(CR²⁰R²¹)$_p$—$C_{3-10}$cycloalkyl, —NH-COC$_{1-6}$alkyl or Z-Het² where Z is a carbonyl group
aryl is phenyl.

A particular group of compounds consists of those compounds of formula (I) wherein
>Y¹—Y² is a trivalent radical of formula (y-2), r is 0 or 1, s is 1, t is 0,
R¹ is halo, $C_{(1-4)}$alkyl or forms a bivalent radical of formula (a-1),
R² is halo, cyano or $C_{1-4}$alkyl,
R³ is hydrogen or a radical of formula (b-1) or (b-3),
R¹⁰ is hydrogen or -Alk-OR¹³, R¹¹ is hydrogen and R¹² is hydrogen or $C_{1-6}$alkylcarbonyl and R¹³ is hydrogen;
R⁴ is a radical of formula (c-2) or (c-3), wherein R¹⁶ is hydrogen, R¹⁷ is $C_{1-6}$alkyl, R¹⁸ is $C_{1-6}$alkyl, R¹⁸ᵃ is hydrogen;
and R⁷ is cyano,
a $C_{1-10}$alkyl or $C_{2-6}$alkenyl group or a $C_{1-10}$alkyl or $C_{2-6}$alkenyl group substituted by one or more substituents selected from: —NR²²R²³, —NR²²AlkNR²²R²³ and —NR²²$C_{2-6}$alkenyl;
or R⁷ is group of formula:
—COOR²⁹, —CONR²²R²³, —CONR²²(CR²⁰R²¹)$_p$—$C_{3-10}$cycloalkyl, —CONR²²$C_{2-6}$alkenyl, —CONR²²Ar², —CONR²²Het², —CONR²²AlkNR²²R²³, —CONR²²AlkAr², —CONR²²AlkHet² or —NHCOC$_{1-10}$alkyl;
or a group of formula —Z-Het²
  in which Z is a chemical bond or a carbonyl group.

More preferred compounds are those compounds of formula (I) wherein >Y¹—Y² is a trivalent radical of formula (y-2), r is 0 or 1, s is 1, t is 0, R¹ is halo, preferably chloro and most preferably 3-chloro, R² is halo, preferably 4-chloro or 4-fluoro, or cyano, preferably 4-cyano, R³ is hydrogen or a radical of formula (b-1) or (b-3), R⁹ is hydrogen, R¹⁰ is hydrogen, R¹¹ is hydrogen and R¹² is hydrogen,
R⁴ is a radical of formula (c-2) or (c-3), wherein R¹⁶ is hydrogen, R¹⁷ is $C_{1-6}$alkyl, R¹⁸ is $C_{1-6}$alkyl, R¹⁸ᵃ is hydrogen;
and R⁷ is cyano or a group of formula
—COOR²⁹
—CONR²²R²³
—CONR²²(CR²⁰R²¹)$_p$—$C_{3-10}$cycloalkyl
—CONR²²$C_{2-6}$alkenyl
—CONR²²AlkNR²²R²³
or a group of formula —Z-Het² in which Z is a chemical bond or a carbonyl group.

Especially preferred compounds are those compounds of formula (I) wherein >Y¹—Y² is a trivalent radical of formula (y-2), r and s are 1, t is 0, R¹ is halo, preferably chloro, and most preferably 3-chloro or R¹ is $C_{1-4}$alkyl, preferably 3-methyl, R² is halo, preferably chloro, and most preferably 4-chloro, or cyano, preferably 4-cyano, R³ is a radical of formula (b-1) or (b-3), R⁹ is hydrogen, R¹⁰ and R¹¹ are hydrogen and R¹² is hydrogen or hydroxy, R⁴ is a radical of formula (c-2) or (c-3), wherein R¹⁶ is hydrogen, R¹⁷ is $C_{1-6}$alkyl preferably methyl, R¹⁸ is $C_{1-6}$alkyl preferably methyl, R¹⁸ᵃ is hydrogen; and R⁷ is selected from cyano, hydroxycarbonyl, aminocarbonyl, methylaminocarbonyl, n-propylaminocarbonyl, n-butylaminocarbonyl, cyclopropylaminocarbonyl, prop-1-en-2-ylaminocarbonyl, 1-ethoxycarbonyl-piperidin-4-ylaminocarbonyl, dimethylaminoethylaminocarbonyl, 4-morpholinylethylaminocarbonyl, 4-methylpiperazinylcarbonyl or 3-pyridyl.

The most preferred compounds according to the invention are:
(±)-4-(3-chlorophenyl)-α-(4-chlorophenyl)-α-(1-methyl-1H-imidazol-5-yl)-2-[(2-propenylamino)methyl]-6-quinolinemethanol,
(±)-4-(3-chlorophenyl)-α-(4-chlorophenyl)-2-[[[2-(diethylamino)ethyl]amino]methyl]-α-(1-methyl-1H-imidazol-5-yl)-6-quinolinemethanol,
(±)-4-(3-chlorophenyl)-α-(4-chlorophenyl)-α-(1-methyl-1H-imidazol-5-yl)-2-[[[2-(1-pyrrolidinyl)ethyl]amino] methyl]-6-quinolinemethanol,
(±)-4-(3-chlorophenyl)-6-[(4-chlorophenyl)(1-methyl-1H-imidazol-5-yl)methyl]-N-(2-propenyl)-2-quinolinecarboxamide,*
(±)-4-(3-chlorophenyl)-6-[(4-chlorophenyl)(1-methyl-1H-imidazol-5-yl)methyl]-N-[2-(dimethylamino)ethyl]-2-quinolinecarboxamide,*
(±)-4-(3-chlorophenyl)-6-[(4-chlorophenyl)(1-methyl-1H-imidazol-5-yl)methyl]-N-[2-(4-morpholinyl)ethyl]-2-quinolinecarboxamide,*
(±)-ethyl 4-[[[4-(3-chlorophenyl)-6-[(4-chlorophenyl)(1-methyl-1H-imidazol-5-yl)methyl]-2-quinolinyl]carbonyl]amino]-1-piperidinecarboxylate,
(±)-1-[4-(3-chlorophenyl)-6-[(4-chlorophenyl)(1-methyl-1H-imidazol-5-yl)methyl]-2-quinolinylcarbonyl]piperidine,*
(±)-1-[4-(3-chlorophenyl)-6-[(4-chlorophenyl)(1-methyl-1H-imidazol-5-yl)methyl]-2-quinolinecarbonyl]-4-methylpiperazine,*
(±)-4-(3-chlorophenyl)-6-[(4-chlorophenyl)(1-methyl-1H-imidazol-5-yl)methyl]-N-(2-furanylmethyl)-2-quinolinecarboxamide,
(±)-4-(3-chlorophenyl)-6-[(4-chlorophenyl)(1-methyl-1H-imidazol-5-yl)methyl]-N-cyclopropyl-2-quinolinecarboxamide,*
(±)-4-(3-chlorophenyl)-6-[(4-chlorophenyl)(1-methyl-1H-imidazol-5-yl)methyl]-N-[2-(1-pyrrolidinyl)ethyl]-2-quinolinecarboxamide,*
(±)-4-(3-chlorophenyl)-6-[(4-chlorophenyl)(1-methyl-1H-imidazol-5-yl)methyl]-N-(4-pyridinylmethyl)-2-quinolinecarboxamide,
(±)-4-(3-chlorophenyl)-α-(4-chlorophenyl)-2-methyl-α-(4-methyl-4H-1,2,4-triazol-3-yl)-6-quinolinemethanamine,
(±)-4-(3-chlorophenyl)-α-(4chlorophenyl)-2-methyl-α-(1-methyl-1H-imidazol-5-yl)-6-quinazolinemethanol,
(±)-4-(3-chlorophenyl)-α-(4-chlorophenyl)-2-methyl-α-(4-methyl-4H-1,2,4-triazol-3-yl)-6-quinolinemethanol, and
(±)-2-amino-4-(3-chlorophenyl)-α-(4-chlorophenyl)-α-(1-methyl-1H-imidazol-5-yl)-6-quinazolinemethanol, and their pharmaceutically acceptable salts.

Those compounds identified by an asterisk are particularly preferred.

The compounds of formula (I) and their pharmaceutically acceptable salts or N-oxides or stereochemically isomeric forms may be prepared in conventional manner, for example, by a process which comprises:

a) cyclising a compound of formula (II):

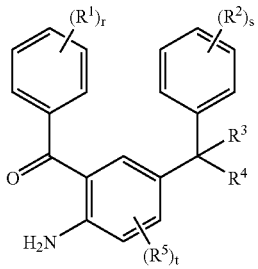

with (i) a compound of formula (III):

$R^7$—CO—$CH_3$  (III)

or (ii) a compound of formula $R^9CH_2CN$ to form a compound of formula (I) in which $R^7$ is amino and $R^9$ is hydrogen, $C_{1-6}$alkyl or aryl; or b) reacting a compound of formula (IV):

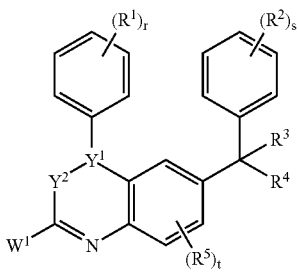

in which $W^1$ represents a replaceable or reactive group, with a reagent serving either to replace the $W^1$ group in compound (IV) with an $R^7$ group or to react with the $W^1$ group to form an $R^7$ group; or c) reacting a compound of formula (V):

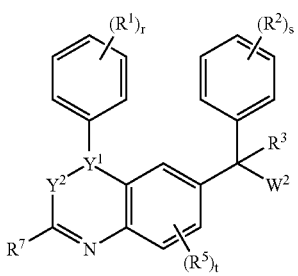

in which $W^2$ is a replaceable group, with an imidazole reagent serving to replace the group $W^2$ with an $R^4$ group of formula (c-1); or d) reacting a compound of formula (VI):

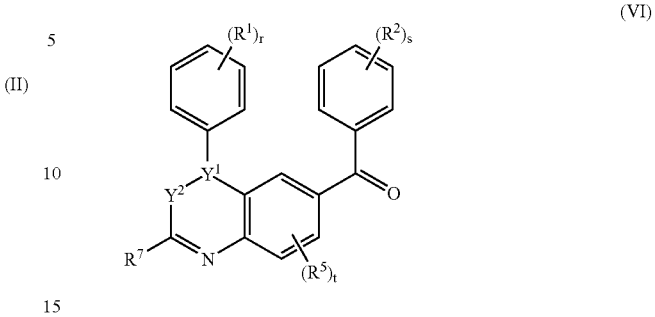

with an imidazole reagent to form a compound of formula (I) in which $R^4$ is a group of formula (c-2), or with a 3-mercapto-4-methyl-1,2,4-triazole reagent to form a compound of formula (I) in which $R^4$ is a group of formula (c-3), or with a 3-bromopyridyl group to form a compound of formula (I) wherein $R^4$ is a group of formula (c-4).

e) reacting a compound of formula (VII):

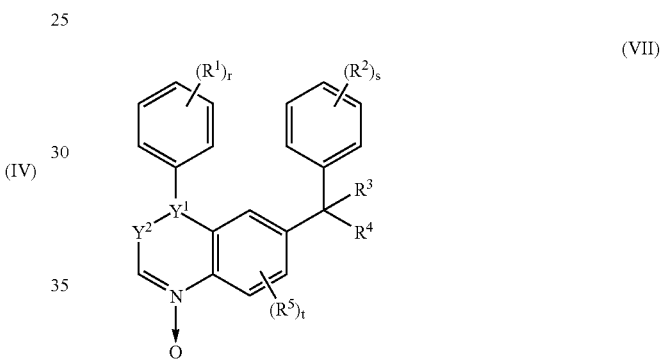

with a cyano compound to form a compound of formula (I) in which $R^7$ is a cyano group;

and optionally effecting one or more of the following conversions in any desired order:
i) converting a compound of formula (I) into a different compound of formula (I);
ii) converting a compound of formula (I) in to a pharmaceutically acceptable salt or N-oxide thereof;
iii) converting a pharmaceutically acceptable salt or N-oxide of a compound of formula (I) into the parent compound of formula (I);
iv) preparing a stereochemical isomeric form of a compound of formula (I) or a pharmaceutically acceptable salt or N-oxide thereof.

With regard to process a)(i), the cyclisation may be effected for example by reaction of the compounds of formulae (II) and (III) in the presence of an acid such as sulphuric acid, and in an acidic solvent such as acetic acid or trifluoroacetic acid. With regard to process a)(ii), the reaction of the compound of formula (I) and acetonitrile is advantageously effected in the presence of sodium hydride.

With regard to process b), for example for the preparation of compounds of formula (I) in which $R^7$ comprises (a) an alkyl, alkenyl, alkynyl, aryl or heterocycle group, this may be carried out for example by reaction of a compound of formula (IV) in which $W^1$ is halo, preferably chloro, with an organometallic compound, e.g. a boron or tin compound of formula $R^7$—$B(OH)_2$ or R⁷—Sn(R′′′)₃ in which R′′′ is $C_{1-4}$ alkyl, the reaction being conducted in an organic solvent such as dioxan or dimethylformamide, and at a temperature of 60–140° C. and in the presence of a palladium-triphenylphosphine catalyst.

For the preparation of compounds of formula (I) in which $R^7$ is a hydroxycarbonyl group, a compound of formula (IV) in which $W^1$ is halo may be reacted with carbon monoxide under super-atmospheric pressure in the presence of a $Pd(OAc)_2$—$PPh_3$ catalyst, with an $C_{1-6}$alkanol to form the corresponding compound of formula (I) in which $R^7$ is a $C_{1-6}$alkyloxycarbonyl group which can be converted into the corresponding hydroxycarbonyl group for example by hydrolysis with lithium hydroxide. For the preparation of compounds of formula (I) in which $R^7$ is an amino group, a compound of formula (IV) in which $W^1$ is halo may be reacted with hydrazine and then be reduced by the Ni-Raney catalyst.

Compounds of formula (IV) in which $W^1$ is a halocarbonyl group for example —COCl, can be reacted for example with an amine of formula $HNR^{22}R^{23}$ to form a compound of formula (I) in which $R^7$ is a group of formula —$CONR^{22}R^{23}$.

Compounds of formula (IV) in which $W^1$ is an aldehyde group can be subjected to the following reactions in accordance with process b):

i) treatment with a reducing agent such as sodium borohydride, e.g. in a solvent such as tetrahydrofuran, to form a compound of formula (I) in which $R^7$ is a hydroxymethyl group;

ii) treatment with hydroxylamine, e.g. in an ethanol solvent and at an elevated temperature to form a compound of formula (I) in which $R^7$ is a group of formula —CH=NOH;

iii) treatment with a $(EtO)_2P(O)CH_2CO_2Et$ reagent in the presence of potassium tert-butoxide and in a tetrahydrofuran solvent to form a compound of formula (I) in which $R^7$ is a group of formula —CH=CHCO₂Et;

iv) treatment with $(EtO)_2P(O)CH2CN$ in the presence of potassium tert-butoxide and in a tetrahydrofuran solvent to form a compound of formula (I) in which $R^7$ is a group of formula —CH=CH—CN.

With regard to process c), this can be effected for example by N-alkylating an intermediate of formula (V), wherein $W^2$ is an appropriate leaving group such as, for example, chloro, bromo, methanesulfonyloxy or benzenesulfonyloxy, with an intermediate of formula (IX) to form a compound of formula (I) in which $R^4$ is a group of formula (c-1) represented by compounds of formula (I-a):

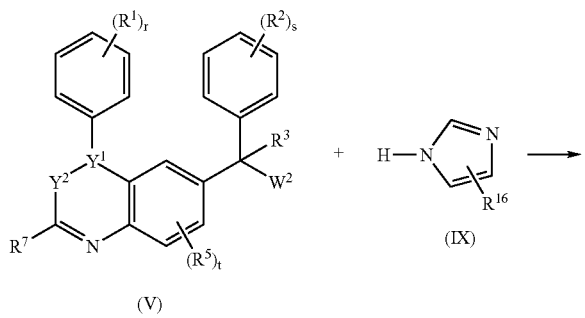

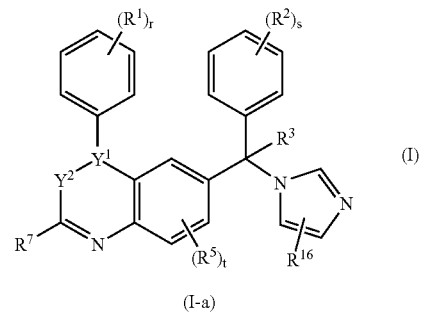

The reaction can be performed in a reaction-inert solvent such as, for example, acetonitrile, and optionally in the presence of a suitable base such as, for example, sodium carbonate, potassium carbonate or triethylamine. Stirring may enhance the rate of the reaction. The reaction may conveniently be carried out at a temperature ranging between room temperature and reflux temperature.

Also, compounds of formula (I-a) can be prepared by reacting an intermediate of formula (V) in which $W^2$ is hydroxy with an intermediate of formula (X), wherein Y is oxygen or sulfur, such as, for example, a 1,1'-carbonyldiimidazole.

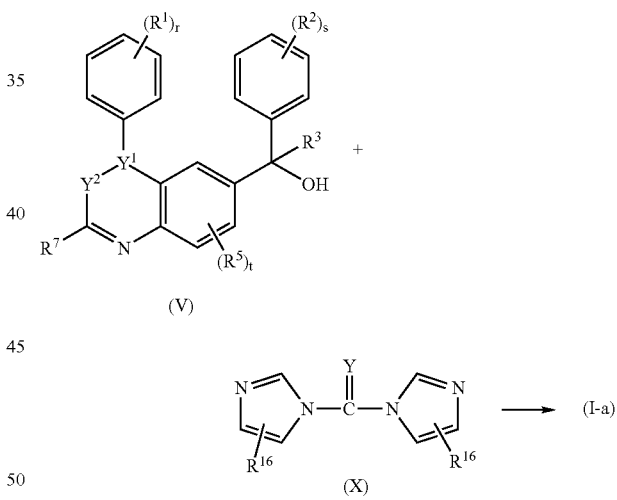

Said reaction may conveniently be conducted in a reaction-inert solvent, such as, e.g. tetrahydrofuran, optionally in the presence of a base, such as sodium hydride, and at a temperature ranging between room temperature and the reflux temperature of the reaction mixture.

With regard to process d), this can be used to introduce the $R^4$ group, for example by reacting a compound of formula (VI) in which $R^x$ is $R^2$ with an imidazole reagent to form a compound of formula (I) in which $R^4$ is a group of formula (c-2), or with a 3-mercapto-4-$C_{1-6}$alkyl-1,2,4-triazole reagent to form the corresponding 3-mercapto-4-$C_{1-6}$alkyl-1,2,4-triazole derivative, which is optionally methylated to form the corresponding 3-methylmercapto derivative, and subsequently removing the 3-mercapto or 3-methylmercapto group to form a compound of formula (I) in which $R^4$ is a group of formula (c-3) in which $R^{18}$ is a $C_{1-6}$alkyl group; or with a 3-bromopyridyl group to form a compound of formula (I) in which $R^4$ is a group of formula (c-4). In more detail, the compounds of formula (I) wherein $R^4$ represents a radical of formula (c-2), $R^3$ is hydroxy and $R^{17}$ is $C_{1-6}$alkyl, said compounds being referred to as compounds of formula (I-b-1), may be prepared by reacting an intermediate ketone of formula (VI) with an intermediate of formula (III-1). Said reaction requires the presence of a suitable strong base, such as, for example, butyl lithium in an appropriate solvent, such as, for example, tetrahydrofuran, and the presence of an appropriate silane derivative, such as, for example, triethylchlorosilane. During the work-up procedure an intermediate silane derivative is hydrolyzed. Other procedures with protective groups analogous to silane derivatives can also be applied.

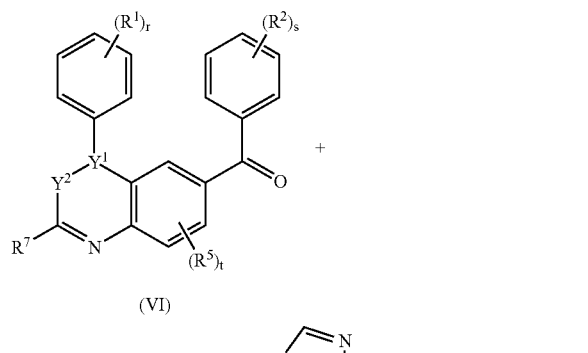

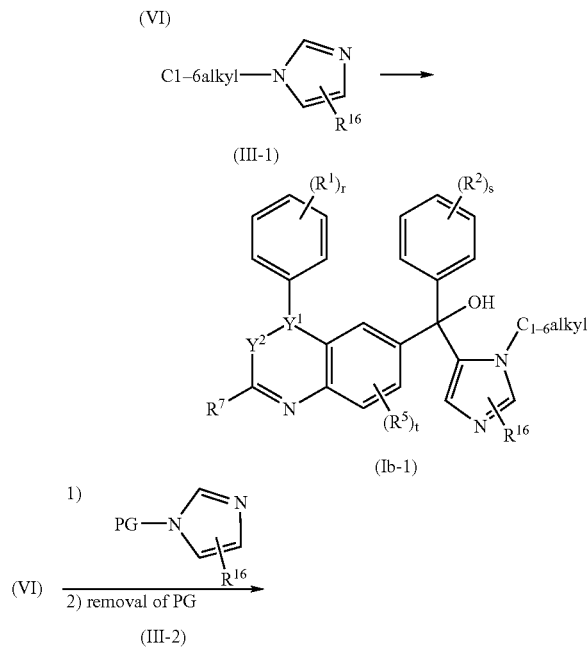

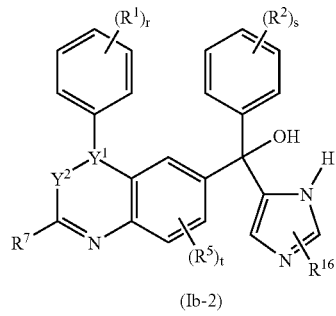

Also, the compounds of formula (I), wherein $R^4$ is a radical of formula (c-2), $R^3$ is hydroxy and $R^{17}$ is hydrogen, said compounds being referred to as compounds of formula (I-b-2) may be prepared by reacting an intermediate ketone of formula (VI) with a intermediate of formula (III-2), wherein PG is a protective group such as, for example, a sulfonyl group, e.g. a dimethylamino sulfonyl group, which can be removed after the addition reaction. Said reaction is conducted analogously as for the preparation of compounds of formula (I-b-1), followed by removal of the protecting group PG, yielding compounds of formula (I-b-2).

With regard to process e), the compound of formula (VII) may be reacted for example with trimethylsilyl cyanide in an organic solvent for example dichloromethane at room temperature and in the presence dimethylcarbamylchloride.

Examples of the interconversion of one compound of formula (I) into a different compound of formula (I) include the following reactions:

a) compounds of formula (I-b) can be converted to compounds of formula (I-e), defined as a compound of formula (I) wherein $R^4$ is a radical of formula (c-2) and $R^3$ is hydrogen, by submitting the compounds of formula (I-b) to appropriate reducing conditions, such as, e.g. stirring in acetic acid in the presence of formamide, or treatment with sodium borohydride/trifluoroacetic acid.

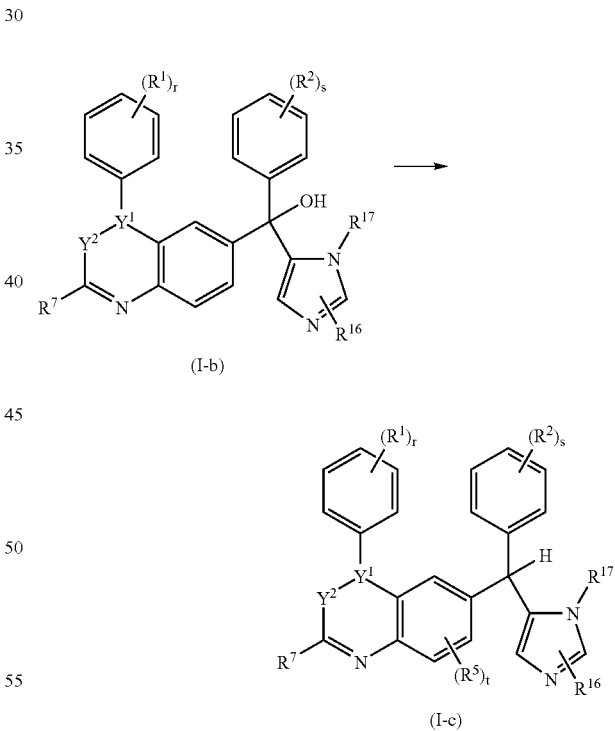

b) compounds of formula (I-b) can be converted to compounds of formula (I-f) wherein $R^3$ is halo, by reacting the compounds of formula (I-b) with a suitable halogenating agent, such as, e.g. thionyl chloride or phosphorus tribromide. Successively, the compounds of formula (I-f) can be treated with a reagent of formula H—$NR^{11}R^{12}$ in a reaction-inert solvent, thereby yielding compounds of formula (I-g).

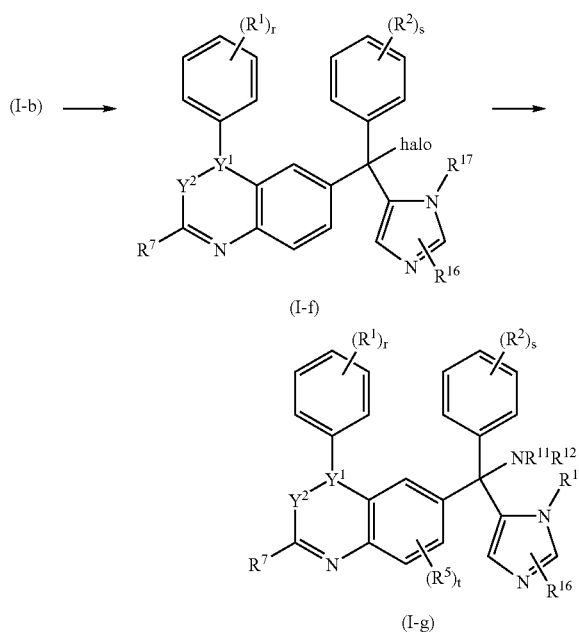

c) compounds of formula (I-b) can be converted into compounds of formula (I-g) for example by treatment with $SOCl_2$, and then $NH_3$/iPrOH, e.g. in a tetrahydrofuran solvent, or by treatment with acetic acid ammonium salt at a temperature ranging from 120 to 180° C., or by treatment with sulfamide at a temperature ranging from 120 to 180° C.;

d) compounds of formula (I-f) can be converted into compounds of formula (I-c) for example by treatment with $SnCl_2$ in the presence of concentrated HCl in acetic acid at reflux.

e) compounds of formula (I) in which $R^7$ is a group of formula —CH═NOH can be converted into a corresponding compound of formula (I) in which $R^7$ is cyano by treatment with CDI preferably in a tetrahydrofuran solvent;

f) compounds of formula (I) in which $R^7$ is a cyano group can be converted into a corresponding compound of formula (I) in which $R^7$ is an aminomethyl group for example by treatment with a reducing agent such as lithium aluminium hydride e.g. in a tetrahydrofuran solvent or by hydrogenation in the presence of a palladium catalyst;

g) compounds of formula (I) in which $R^7$ is a $C_{1-10}$ alkyl e.g. methyl group, can be converted into a corresponding compound of formula (I) in which $R^7$ is a hydroxycarbonyl group for example by treatment with $SeO_2$, e.g. in a dioxan solvent;

h) compounds of formula (I) in which $R^7$ is a hydroxycarbonyl group, can be converted into a corresponding compound of formula (I) in which $R^7$ is an aminocarbonyl group for example by treatment with $SOCl_2$, and then $NH_3$/iPrOH, e.g. in a tetrahydrofuran solvent;

i) compounds of formula (I) in which $R^7$ is an amino group, can be converted into a corresponding compound of formula (I) in which $R^7$ is a carbonylamino group for example by treatment with an appropriate acylating agent or into a compound of formula (I) in which $R^7$ is an aminocarbonyl group or an urea or thiourea group by treatment with an acid, an isocyanate or isothiocyanate respectively.

The compounds used a starting materials in the above-described processes for preparing compounds of formula (I) can be prepared in conventional manner using processes known in the art or which are analogous thereto. Thus, for example, compounds of formula (II) used as starting materials in process a) may be prepared using processes as described in International Patent Specification No. WO97/21701.

Compounds of formula (IV) used as starting materials in process b) may be prepared using processes as described in International Patent Specification WO 00/39082 referred to above. Examples of the group $W^1$ in such compounds include the halo and aldehyde groups. Such processes are especially useful for the preparation of starting materials in which $R^3$ is —$OR^{10}$ especially when $R^3$ is —OH. The resulting compounds of formula (I) can then be converted into other compounds of formula (I) by transformation of the —OH group in conventional manner, for example as described above.

Compounds of formulae (V) and (VI) used as starting materials in processes c) and d) respectively can be prepared by procedures described in International Patent Specification No. WO 98/49157 or by processes analogous thereto. The $R^7$ group in these compounds can be introduced during the formation of the ring containing the nitrogen heteroatom(s) for example using analogous procedures to those described for process b) above.

Compounds of formula (VII) used as starting materials in process e) may be prepared for example as described in International Patent Specification No. WO97/21701.

The compounds of formula (I) and some of the intermediates have at least one stereogenic center in their structure. This stereogenic center may be present in a R or a S configuration.

The compounds of formula (I) as prepared in the hereinabove described processes are generally racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the pharmaceutically acceptable acid addition salts and stereoisomeric forms thereof have valuable pharmacological properties in that they have a potent farnesyl protein transferase (FPTase) inhibitory effect.

This invention provides a method for inhibiting the abnormal growth of cells, including transformed cells, by administering an effective amount of a compound of the invention. Abnormal growth of cells refers to cell growth independent of normal regulatory mechanisms (e.g. loss of contact inhibition). This includes the abnormal growth of: (1) tumor cells (tumors) expressing an activated ras oncogene; (2) tumor cells in which the ras protein is activated as a result of oncogenic mutation of another gene; (3) benign and malignant cells of other proliferative diseases in which aberrant ras activation occurs. Furthermore, it has been suggested in literature that ras oncogenes not only contribute to the growth of tumors in vivo by a direct effect on tumor cell growth but also indirectly, i.e. by facilitating tumor-induced angiogenesis (Rak. J. et al, *Cancer Research*, 55, 4575–4580, 1995). Hence, pharmacologically targeting mutant ras oncogenes could conceivably suppress solid tumor growth in vivo, in part, by inhibiting tumor-induced angiogenesis.

This invention also provides a method for inhibiting tumor growth by administering an effective amount of a compound of the present invention, to a subject, e.g. a mammal (and more particularly a human) in need of such treatment. In particular, this invention provides a method for inhibiting the growth of tumors expressing an activated ras oncogene by the administration of an effective amount of the compounds of the present invention. Examples of tumors which may be inhibited, but are not limited to, lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), prostate cancer including the advanced disease, hematopoietic tumors of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MES), tumors of mesenchymal origin (e.g. fibrosarcomas and rhabdomyosarcomas), melanomas, teratocarcinomas, neuroblastomas, gliomas, benign tumor of the skin (e.g. keratoacanthomas), breast carcinoma (e.g. advanced breast cancer), kidney carcinoma, ovary carcinoma, bladder carcinoma and epidermal carcinoma.

This invention may also provide a method for inhibiting proliferative diseases, both benign and malignant, wherein ras proteins are aberrantly activated as a result of oncogenic mutation in genes. With said inhibition being accomplished by the administration of an effective amount of the compounds described herein, to a subject in need of such a treatment. For example, the benign proliferative disorder neuro-fibromatosis, or tumors in which ras is activated due to mutation or overexpression of tyrosine kinase oncogenes, may be inhibited by the compounds of this invention.

The compound according to the invention can be used for other therapeutic purposes, for example:

a) the sensitisation of tumors to radiotherapy by administering the compound according to the invention before, during or after irradiation of the tumor for treating cancer, for example as described in WO 00/01411;

b) treating athropathies such as rheumatoid arthritis, osteoarthritis, juvenile arthritis, gout, polyarthritis, psoriatic arthritis, ankylosing spondylitis and systemic lupus erythematosus, for example as described in WO 00/01386;

c) inhibiting smooth muscle cell proliferation including vascular proliferative disorders, atherosclerosis and restenosis, for example as described in WO 98/55124;

d) treating inflammatory conditions such as ulcerative colitis, Crohn's disease, allergic rhinitis, graft vs host disease, conjunctivitis, asthma, ARDS, Behcets disease, transplant rejection, uticaria, allergic dermatitis, alopecia areata, scleroderma, exanthem, eczema, dermatomyositis, acne, diabetes, systemic lupus erythematosis, Kawasaki's disease, multiple sclerosis, emphysema, cystic fibrosis and chronic bronchitis;

e) treating endometriosis, uterine fibroids, dysfunctional uterine bleeding and endometrial hyperplasia;

f) treating ocular vascularisation including vasculopathy affecting retinal and choroidal vessels;

g) treating pathologies resulting from heterotrimeric G protein membrane fixation including diseases related to following biological functions or disorders; smell, taste, light, perception, neurotransmission, neurodegeneration, endocrine and exocrine gland functioning, autocrine and paracrine regulation, blood pressure, embryogenesis, viral infections, immunological functions, diabetes, obesity;

h) inhibiting viral morphogenesis for example by inhibiting the prenylation or the post-prenylation reactions of a viral protein such as the large delta antigen of hepatitis D virus; and the treatment of HIV infections;

i) treating polycystic kidney disease;

j) suppressing induction of inducible nitric oxide including nitric oxide or cytokine mediated disorders, septic shock, inhibiting apoptosis and inhibiting nitric oxide cytotoxicity;

k) treating malaria.

The compounds of present invention are particularly useful for the treatment of proliferative diseases, both benign and malignant, wherein the K-ras B isoform is activated as a result of oncogenic mutation.

Hence, the present invention discloses the compounds of formula (I) for use as a medicine as well as the use of these compounds of formula (I) for the manufacture of a medicament for treating one or more of the above mentioned conditions.

For the treatment of the above conditions, the compound of the invention may be advantageously employed in combination with one or more other medicinal agents such as anti-cancer agents for example selected from platinum coordination compounds for example cisplatin or carboplatin, taxane compounds for example paclitaxel or docetaxel, camptothecin compounds for example irinotecan or topotecan, anti-tumor vinca alkaloids for example vinblastine, vincristine or vinorelbine, anti-tumor nucleoside derivatives for example 5-fluorouracil, gemcitabine or capecitabine, nitrogen mustard or nitrosourea alkylating agents for example cyclophosphamide, chlorambucil, carmustine or lomustine, anti-tumor anthracycline derivatives for example daunorubicin, doxorubicin or idarubicin; HER2 antibodies for example trastzumab; and anti-tumor podophyllotoxin derivatives for example etoposide or teniposide; and anti-estrogen agents including estrogen receptor antagonists or selective estrogen receptor modulators preferably tamoxifen, or alternatively toremifene, droloxifene, faslodex and raloxifene, or aromatase inhibitors such as exemestane, anastrozole, letrazole and vorozole.

For the treatment of cancer the compounds according to the present invention can administered to a patient as described above in conjunction with irradiation; such treatment is may be especially beneficial as farnesyl transferase inhibitors can act as radiosensitisers for example as described in International Patent Specification WO 00/01411, enhancing the therapeutic effect of such irradiation.

Irradiation means ionizing radiation and in particular gamma radiation, especially that emitted by linear accelerators or by radionuclides that are in common use today. The irradiation of the tumor by radionuclides can be external or internal.

Preferably, the administration of the farnesyl transferase inhibitor commences up to one month, in particular up to 10 days or a week, before the irradiation of the tumor. Additionally, it is advantageous to fractionate the irradiation of the tumor and maintain the administration of the farnesyl transferase inhibitor in the interval between the first and the last irradiation session.

The amount of farnesyl protein transferase inhibitor, the dose of irradiation and the intermittence of the irradiation doses will depend on a series of parameters such as the type of tumor, its location, the patients' reaction to chemo- or radiotherapy and ultimately is for the physician and radiologists to determine in each individual case.

The present invention also concerns a method of cancer therapy for a host harboring a tumor comprising the steps of
administering a radiation-sensitizing effective amount of a farnesyl protein transferase inhibitor according to the invention before, during or after
administering radiation to said host in the proximity to the tumor.

In view of their useful pharmacological properties, the subject compounds may be formulated into various pharmaceutical forms for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that an effective amount would be from 0.01 mg/kg to 100 mg/kg body weight, and in particular from 0.05 mg/kg to 10 mg/kg body weight. It may be appropriate to administer the required dose as two, three, four or more sub-doses at appropriate intervals throughout the day. Said sub-doses may be formulated as unit dosage forms, for example, containing 0.5 to 500 mg, and in particular 1 mg to 200 mg of active ingredient per unit dosage form.

The following examples are provided for purposes of illustration.

EXPERIMENTAL PART

Hereinafter "THF" means tetrahydrofuran, "DIPE" meane diisopropylether, "DME" means 1,2-dimethoxyethane, "EtOAc" means ethyl acetate, "Et$_3$N" means triethylamine, "DCM" means dichloromethane and "BuLi" means n-butyl lithium.

A. Preparation of the Intermediate

Example A1 a) A mixture of (±)-4-(3-chlorophenyl)-α-(4chlorophenyl)-2-methyl-α-(1-methyl-1H-imidazol-5-yl)-6-quinolinemethanol (0.0316 mol), described in International Patent Specification WO 00/39082, in NH$_2$CHO (60 ml) and acetic acid (120 ml) was stirred at 160° C. for 6 hours, poured out on ice, basified with NH$_4$OH and extracted with CH$_2$Cl$_2$. The organic layer was separated, dried, filtered and the solvent was evaporated till dryness, yielding 14.6 g of (±)-4-(3-chlorophenyl)-6-[(4-chlorophenyl)(1-methyl-1H-imidazol-5-yl)methyl]-2-methylquinoline (intermediate 1).

b) A mixture of intermediate (1) and SeO$_2$ (0.0436 mol) in dioxane (74 ml) and water (5 ml) was stirred at 110° C. for 24 hours, then brought to room temperature, filtered over celite and rinsed with CH$_2$Cl$_2$/CH$_3$OH. The solvent was evaporated till dryness. The residue was purified by column chromatography over silica gel (eluent: CH$_2$Cl$_2$/CH$_3$OH/NH$_4$OH 80/20/3; 70–200 μm). The pure fractions were collected and the solvent was evaporated, yielding 4.1 g of (±)-4-(3-chlorophenyl)-6-[(4-chlorophenyl)(1-methyl-1H-imidazol-5-yl)methyl]-2-quinolinecarboxylic acid (intermediate 2).

c) A mixture of intermediate (2) in thionyl chloride (5 ml) was stirred and refluxed for 4 hours and the solvent was evaporated. The mixture was taken up in DCM and evaporated till dryness, yielding 0.54 g (100%) of (±)-4-(3-chlorophenyl)-6-[(4-chlorophenyl)(1-methyl-1H-imidazol-5-yl)methyl]-2-quinolinecarbonyl chloride monohydrochloride (intermediate 3).

The product was used without further purification in the next reaction step.

Example A2

A mixture of N-[2-(3-chlorobenzoyl)-4-(4-chlorobenzoyl)phenyl]acetamide (0.008 mol), described in International Patent Specification WO97/16443, in NH$_3$/iPrOH (4.5M) (17 ml) was stirred at 160° C. for 6 hours in a small bomb, cooled, poured out into ice water and extracted with DCM. The organic layer was separated, dried (MgSO$_4$), filtered and the solvent was evaporated. The residue was purified by column chromatography over silica gel (eluent: cyclohexane/EtOAc 80/20; 15–40 μm). The pure fractions were collected and the solvent was evaporated. The residue (1.2 g) was crystallized from diethyl ether. The precipitate was filtered off and dried, yielding 1.13 g (36%) of (4-chlorophenyl)[4-(3-chlorophenyl)-2-methyl-6-quinazolinyl]-methanone, mp. 182° C. (intermediate 4).

Example A3 a) A mixture of 2-(4-chlorophenyl)-2-(4-nitrophenyl)-1,3-dioxolane (0.082 mol), described in International Patent Specification WO97/16443, 3-methyl-benzeneacetonitrile (0.147 mol) and sodium hydroxide (0.41 mol) in methanol (75 ml) was stirred at room temperature overnight. Water was added, the precipitate was filtered off, washed with water and cold methanol and dried, yielding 29.6 g (92%) of 5-[ 2-(4-chlorophenyl)-1,3-dioxolan-2-yl]-3-(3-methylphenyl)-2,1-benzisoxazole (intermediate 5).

b) Intermediate (5) (0.074 mol) in THF (300 ml) was hydrogenated with Pd/C (4 g) as a catalyst at room temperature for 3 h under a 2 bar pressure in a Parr apparatus. After uptake of H$_2$ (1eq), the catalyst was filtered through celite, washed with DCM and the filtrate was evaporated till dryness. The product was used without further purification, yielding 29 g (100%) of [2-amino-5-[2-(4-chlorophenyl)-1,3-dioxolan-2-yl]phenyl](3-methylphenyl)-methanone (intermediate 6).

c) Acetic acid anhydride (0.148 mol) was added to a solution of intermediate (6) (0.074 mol) in toluene (350 ml) and the mixture was stirred and refluxed for 2 h. The mixture was evaporated till dryness, the residue was taken up in diethylether and evaporated till dryness. The product was used without further purification, yielding 32 g (100%) of N-[4-[2-(4-chlorophenyl)-1,3-dioxolan-2-yl]-2-(3-methylbenzoyl)phenyl]-acetamide (intermediate 7).

d) 2-Methyl-2-propanol, potassium salt (0.296 mol) was added portionwise at room temperature to a solution of intermediate (7) (0.074 mol) in DME (400 ml) and the mixture was stirred at room temperature for 5 days. Water was added and the mixture was extracted with DCM and a little methanol. The organic layer was dried (MgSO$_4$), filtered off and evaporated till dryness. The product was used without further purification, yielding 32 g (100%) of 6-[2-(4-chlorophenyl)-1,3-dioxolan-2-yl]-4-(3-methylphenyl)-2(1H)-quinolinone (intermediate 8).

e) A mixture of intermediate (8) (0.074 mol) in HCl 3N (400 ml) and methanol (20 ml) was stirred and refluxed for 2 h. The mixture was filtered, the precipitate was washed with water and diethylether and dried. The product was used without further purification, yielding 26 g (94%) of 6-(4-chlorobenzoyl)4-(3-methylphenyl)-2(1H)-quinolinone (intermediate 9).

f) A mixture of intermediate (9) (0.0535 mol) in phosphoryl chloride (200 ml) was stirred at 100° C. for 4 hours. The solvent was evaporated till dryness. The residue was taken up in ice water. The precipitate was filtered off, pasted up with water and taken up in DCM. The organic solution was dried (MgSO$_4$), filtered and the solvent was evaporated till dryness, yielding 21 g (100%) of [2-chloro-4-(3-methylphenyl)-6-quinolinyl](4-chlorophenyl)-methanone, mp.199° C. (intermediate 10).

Example A4

A mixture of 2-chloro-4-(3-chlorophenyl)-α-(4-chlorophenyl)-α-(1-methyl-1H-imidazol-5-yl)-6-quinazolinemethanol (0.0040 mol), described in International Patent Specification WO 00/39082, in hydrazine (20 ml) and dioxane (40 ml) was stirred at 70° C. for 20 minutes. Saturated sodium chloride solution was added. The mixture was extracted with DCM. The organic layer was separated, dried (MgSO$_4$), filtered, and the solvent was evaporated till dryness. The residue (2.15 g) was purified by column chromatography over silica gel (eluent: CH$_2$Cl$_2$/CH$_3$OH; 95/5 to 90/10; 70–200 μm). The pure fractions were collected and the solvent was evaporated, yielding 1.5 g (76%) of 4-(3-chlorophenyl)-α-(4-chlorophenyl)-2-hydrazino-α-(1-methyl-1H-imidazol-5-yl)-6-quinazolinemethanol, mp.186° C. (intermediate 11).

Example A5 a) BuLi 1.6M in hexane (0.0814 mol) was added dropwise at –70° C. under N$_2$ flow to a mixture of 3-bromo-pyridine (0.0814 mol) in diethyl ether (150 ml). The mixture was stirred at –70° C. for 1 hour. A mixture of (4-chlorophenyl)[3-(3-chlorophenyl)-2,1-benzisoxazol-5-yl]methanone (0.0543 mol), described in International Patent Specification WO97/21701, in THF (200 ml) was added dropwise. The mixture was stirred at –70° C. for 1 hour, allowed to warm to –30° C. and hydrolysed. EtOAc was added. The organic layer was separated, dried (MgSO$_4$), filtered and the solvent was evaporated till dryness. The residue (27 g) was purified by column chromatography over silica gel (eluent: CH$_2$Cl$_2$/CH$_3$OH/NH$_4$OH 97.5/2.5/0.1; 20–45 μm). The pure fractions were collected and the solvent was evaporated, yielding 9.1 g (37.6%) of a fraction which was crystallized from EtOAc and DIPE. The precipitate was filtered off and dried, yielding 1.5 g (6.2%) of 3-(3-chlorophenyl)-α-(4-chlorophenyl)-α-(3-pyridinyl)-2,1-benzisoxazole-5-methanol, mp.199° C. (intermediate 12).

b) TiCl$_3$ 15% in H$_2$O (0.163 mol) was added dropwise at room temperature to a mixture of intermediate (12) (0.031 mol) in THF (100 ml). The mixture was stirred at room temperature for 3 hours, poured out into ice water, extracted with DCM and basified with potassium carbonate. The organic layer was separated, dried (MgSO$_4$), filtered and the solvent was evaporated till dryness, yielding 13.5 g (100%) of [2-amino-5-[(4-chlorophenyl)-3-pyridinylmethyl]phenyl](3-chlorophenyl)-methanone (intermediate 13).

c) A mixture of 2-propanone (0.09 mol) in H$_2$SO$_4$ (0.45 ml) was added to a mixture of intermediate (13) (0.03 mol) in acetic acid (110 ml). The mixture was stirred and refluxed overnight, poured out into ice water, basified with a diluted solution of NH$_4$OH and extracted with DCM. The organic layer was separated, dried (MgSO$_4$), filtered and the solvent was evaporated till dryness. This product was used without further purification, yielding (85%) of 4-(3-chlorophenyl)-6[(4-chlorophenyl)-3-pyridinylmethyl]-2-methyl-quinoline (intermediate 14).

d) SeO$_2$ (0.019 mol) was added to a mixture of intermediate (14) (0.019 mol) in dioxane (90 ml) and water (8.78 ml). The mixture was stirred and refluxed for 3 hours, filtered over celite and rinsed with DCM. The organic layer was separated, dried (MgSO$_4$), filtered and the solvent was evaporated till dryness. The residue was purified by column chromatography over silica gel (eluent: CH$_2$Cl$_2$/CH$_3$OH 98.5/1.5; 15–35 μm). The pure fractions F1 and F2 were collected and the solvent was evaporated, yielding 1.8 g (26%) of F1 and 0.5 g F2. F2 was crystallized from CH$_3$CN. The precipitate was filtered off and dried, yielding 0.25 g (26%) of 4-(3-chlorophenyl)-6-[(4-chlorophenyl)-3-pyridinylmethyl]-2-quinolinecarboxaldehyde, mp.168° C. (intermediate 15).

B. Preparation of the Final Compounds

Example B1

NH$_2$OH.HCl (0.00246 mol) was added to a solution of (±)-4-(3-chlorophenyl)-6-[(4-chlorophenyl)hydroxy(1-methyl-1H-imidazol-5-yl)methyl]-2-quinolinecarboxaldehyde (0.00164 mol), described in International Patent Specification WO 00/39082, in ethanol (8 ml). The mixture was stirred at room temperature for 2 hours, poured out into K$_2$CO$_3$ (10%) and extracted with EtOAc. The organic layer was separated, dried, filtered and the solvent was evaporated. The residue was purified by column chromatography over silica gel (eluent: toluene/iPrOH/NH$_4$OH 85/15/1; 15–40 μm). The pure fractions were collected and the solvent was evaporated, yielding 0.29 g (35%) of (±)-4-(3-chlorophenyl)-6-[(4-chlorophenyl)hydroxy(1-methyl-1H-imidazol-5-yl)methyl]-2-quinolinecarboxaldehyde, oxime of indeterminate E/Z configuration, mp. 205° C.

Example B2

2-Methyl-2-propanol, potassium salt (0.005 mol) was added at room temperature to a solution of ethyl (diethylphosphono)acetate (0.005 mol) in THF (10 ml) under N$_2$ flow. A solution of (±)-4-(3-chlorophenyl)-6-[(4-chlorophenyl)hydroxy(1-methyl-1H-imidazol-5-yl)methyl]-2-quinolinecarboxaldehyde (0.0039 mol) (see Example B1) in THF (20 ml) was added. The mixture was stirred at room temperature for 7 hours, poured out into ice water and extracted with EtOAc. The organic layer was separated, dried, filtered and the solvent was evaporated. The residue was purified by column chromatography over silica gel (eluent: CH$_2$Cl$_2$/CH$_3$OH/NH$_4$OH 96.5/3.5/0.2; 15–40 μm). The pure fractions were collected and the solvent was evaporated, yielding 0.84 g of (±)-ethyl (E)-3-[4-(3-chlorophenyl)-6-[(4-chlorophenyl)hydroxy(1-methyl-1H-imidazol-5-yl)methyl]-2-quinolinylpropenoate, mp. 80° C.

Example B3

2-Methyl-2-propanol, potassium salt (0.0045 mol) was added portionwise at 5° C. to a solution of diethyl (cyanomethyl)phosphonate (0.0045 mol) in THF (15 ml) under N$_2$ flow. The mixture was stirred at room temperature for 30 minutes. A solution of (±)-4-( 3-chlorophenyl)-6-[(4-chlorophenyl)hydroxy(1-methyl-1H-imidazol-5-yl)methyl]-2-quinolinecarboxaldehyde (0.0041 mol) (see Example B1) in THF (20 ml) was added dropwise. The mixture was stirred at room temperature for 4 hours, poured out into H$_2$O and extracted with EtOAc. The organic layer was separated, dried, filtered, and the solvent was evaporated. The residue was purified by column chromatography over silica gel (eluent: CH$_2$Cl$_2$/CH$_3$OH/NH$_4$OH; 96/4/0.2; 15–40 μm). The pure fractions were collected and the solvent was evaporated. The residue was crystallized from 2-propanone/diethyl ether. The precipitate was filtered off and dried, yielding 0.5 g of (±)-(E)-3-[4-(3-chlorophenyl)-6-[(4-chlorophenyl)hydroxy(1-methyl-1H-midazol-5-yl)methyl]-2-quinolinyl]-2-propenenitrile, mp. 200° C.

Example B4

A mixture of (±)-4-(3-chlorophenyl)-6-[(4-chlorophenyl)hydroxy(1-methyl-1H-imidazol-5-yl)methyl]-2-quinolinecarboxaldehyde (0.000205 mol) (see Example B1), N,N-diethylethanediamine (0.000512 mol) and acetic acid (0.1 ml) in acetonitrile (2 ml) was stirred for 2 hours at room temperature. NaBH$_3$CN (0.03 g) was added and the resulting mixture was stirred overnight at room temperature. Water (1 ml) was added and the solvent was evaporated. The residue was HPLC purified, yielding (±)-4-(3-chlorophenyl)-α-(4-chlorophenyl)-2-[[[2-(diethylano)ethyl]amino]methyl]-α-(1-methyl-1H-imidazol-5-yl)-6-quinolinemethanol, MS (ESI) m/z:588 590 592 (MH$^+$).

Example B5

A mixture of (±)-2-chloro-4-(3-chlorophenyl)-α-(4-chlorophenyl)-α-(1-methyl-1H-imidazol-5-yl)-6-quinolinemethanol (0.0061 mol), described in International Patent Specification WO 00/39082, tributyl (1-ethoxyethenyl)-stannane (0.0091 mol) and Pd(PPh$_3$)$_4$ (0.0007 mol) in dioxane(30 ml) was stirred at 80° C. for 24 hours, cooled and poured out into ice water. EtOAc was added and the mixture was filtered over celite. The organic layer was separated, dried, filtered and the solvent was evaporated, yielding 3.8 g of (±)-4-(3-chlorophenyl)-α-(4-chlorophenyl)-2-(1-ethoxyethenyl)-α-(1-methyl-1H-imidazol-5-yl)-6-quinolinemethanol.

Example B6

A mixture of 2-chloro-4-(3-chlorophenyl)-α-(4-chlorophenyl)-α-(1-methyl-1H-imidazol-5-yl)-6-quinazolinemethanol (0.004 mol), described in International Patent Specification WO 00/39082, 1-methyl-5-(tributylstannyl)-1H-midazole (0.02 mol), Pd(PPh$_3$)$_4$ (0.0008 mol) and triethylamine (0.006 mol) in toluene (30 ml) was stirred at 100° C. for 6 hours, then brought to room temperature and poured out into ice water. EtOAc was added. The mixture was basified with potassium carbonate 10%. The precipitate was filtered over celite and the celite was then washed with EtOAc. The filtrate was extracted with EtOAc. The organic layer was separated, washed with water, dried (MgSO$_4$), filtered, and the solvent was evaporated. The residue was purified by column chromatography over silica gel (eluent: CH$_2$Cl$_2$/CH$_3$OH/NH$_4$OH 95/5/0.5; 15–40 μm). One fraction was collected and the solvent was evaporated. This fraction was washed with diethyl ether. The precipitate was filtered off and dried under a vacuum, yielding 0.5 g (23%) of 4-(3-chlorophenyl)-α-(4-chlorophenyl)-α,2-bis(1-methyl-1H-imidazol-5-yl)-6-quinazolinemethanol, mp.160° C.

Example B7

A mixture of (±)-4-(3-chlorophenyl)-6-[(4-chlorophenyl)(1-methyl-1H-imidazol-5-yl)methyl]-2-quinolinecarbonyl chloride monohydrochloride (0.00564 mol) intermediate (3), obtained in Example A1c, and N,N dimethyl-1,2-ethanediamine, (0.0282 mol) in THF (50 ml) was stirred for one hour at 5° C. and at room temperature for 18 hours. Water was added and the mixture was extracted with EtOAc. The separated organic layer was evaporated and the residue was purified by column chromatography over silica gel (eluent: $CH_2Cl_2/CH_3OH$ 93/7/0.5; 15–40 µm). The pure fractions were collected and the solvent was evaporated, yielding after crystallisation from acetonitrile 0.7 g (22%) of (±)-4-(3-chlorophenyl)-6-[(4-chlorophenyl)(1-methyl-1H-imidazol-5-yl)methyl]-N-[2-(dimethylamino)ethyl]-2-quinolinecarboxamide, mp. 184° C.

Example B8

A mixture of (±)-2-amino-4-(3-chlorophenyl)-α-(4-chlorophenyl)-α-(1-methyl-1H-imidazol-5-yl)-6-quinolinemethanol (0.00021 mol), described in International Patent Specification WO 00/39082, and 2-furancarbonyl chloride (0.00063 mol) in THF (1 ml) was heated for 5 hours at 60° C. The solvent was evaporated and the residue was purified by HPLC. The product fractions were collected and the solvent was evaporated, yielding (±)-N-[4-(3-chlorophenyl)-6-[(4-chlorophenyl)hydroxy(1-methyl-1H-imidazol-5-yl)methyl]-2-quinolinyl]-2-furancarboxamide, MS (ESI) m/z: 569 571 573.

Example B9

A mixture of (±)-2-amino-4-(3-chlorophenyl)-α-(4-chlorophenyl)-α-(1-methyl-1H-imidazol-5-yl)-6-quinolinemethanol (0.000210 mol) (see Example B8) and isocyanato-benzene (0.000630 mol; 3 equiv) in THF (1 ml) was stirred for 5 hours at 60° C. Water (a few drops) was added. The solvent was evaporated. The residue was HPLC purified. The product fractions were collected and the solvent was evaporated, yielding 0.071 g (56.77%) of (±)-N-[4-(3-chlorophenyl)-6-[(4-chlorophenyl)hydroxy(1-methyl-1H-imidazol-5-yl)methyl]-2-quinolinyl]-N'-phenylurea, MS (ESI) m/z: 594 596 598.

Example B10

A mixture of (±)-2-amino-4-(3-chlorophenyl)-α-(4-chlorophenyl)-α-(1-methyl-1H-imidazol-5-yl)-6-quinolinemethanol (0.000210 mol) (see Example B8), 4-bromobenzoic acid (0.000252 mol), N'-(ethylcarbonimidoyl)-N,N-dimethyl-1,3-propanediamine monohydrochloride (0.000315 mol), 1-hydroxy-1H-benzotriazole (0.000315 mol; 1.5 equiv) and $Et_3N$ (0.000315 mol) in THF (2 ml) was stirred for 18 hours at room temperature, then taken up into EtOAc and $H_2O$. The organic layer was separated and the solvent evaporated. The residue was purified by HPLC. The product fractions were collected and the solvent was evaporated, yielding 0.065 g (41%) of (±)-4-bromo-N-[4-(3-chlorophenyl)-6-[(4-chlorophenyl)hydroxy(1-methyl-1H-imidazol-5-yl)methyl]-2-quinolinyl]benzamide, MS (ESI) m/z: 657 659 661 663.

Example B11

A mixture of (±)-(E)-3-[4-(3-chlorophenyl)-6-[(4-chlorophenyl)hydroxy(1-methyl-1H-imidazol-5-yl)methyl]-2-quinolinyl]-2-propenenitrile (0.0008 mol), obtained in Example B3, and $MnO_2$ (0.02 mol) in 1,4-dioxane (15 ml) and water (0.8 ml) was stirred at 100° C. for 24 hours then cooled, filtered over celite and rinsed with EtOAc. The organic layer was separated, dried ($MgSO_4$), filtered, and the solvent was evaporated. The residue (0.205 g) was purified by column chromatography over silica gel (eluent: toluene/iPrOH/$NH_4OH$; 80/20/0.5; 15–40 µm). The pure fractions were collected and the solvent was evaporated. The residue (0.044 g) was taken up in $CH_2Cl_2$. The organic layer was separated, washed with $K_2CO_3$ (10%), dried ($MgSO_4$), filtered and the solvent was evaporated, to give 0.024 g of (±)-(E)-3-[4-(3-chlorophenyl)-6-[(4-chlorophenyl)hydroxy (1-methyl-1H-imidazol-5-yl)methyl]-2-quinolinyl]-2-propenamide (6%), mp. 80° C.

Example B12

A mixture of 2-chloro-4-(3-chlorophenyl)-α-(4-chlorophenyl)-α-(1-methyl-1H-imidazol-5-yl)-6-quinazolinemethanol (0.001 mol), described in International Patent Specification WO 00/39082, palladium(II) acetate (0.0001 mol), $PPh_3$ (0.0015 mol) and $K_2CO_3$ (0.002 mol) in 2-propanol (5 ml) and DMF (5mi) was stirred at 90° C. for 18 hours under a 5 bar pressure, filtered over celite and washed with EtOAc. Water was added. The mixture was extracted with EtOAc. The organic layer was separated, dried ($MgSO_4$), filtered and the solvent was evaporated. The residue (0.77 g) was purified by column chromatography over silica gel (eluent: $CH_2Cl_2/CH_3OH$ 96/4/0.2; 15–40 µm). The pure fractions were collected and the solvent was evaporated, yielding 0.125 g (23%) of 1-methylethyl-4-(3-chlorophenyl)-6-[(4-chlorophenyl)hydroxy(1-methyl-1H-imidazol-5-yl)methyl]-, 2-quinazolinecarboxylate,mp. 80° C.

Example B13

BuLi (2.9 ml;0.0046 mol) was added dropwise at −70° C. to a solution of 1-methyl-1H-imidazole (0.0046 mol) in THF (7 ml) under $N_2$ flow. The mixture was stirred at −70° C. for 15 min. Chlorotriethyl-silane (0.0048 mol) was added. The mixture was stirred at −70° C. for 15 min. n BuLi (2.6 ml;0.0041 mol) was added dropwise. The mixture was stirred at −70° C. for 15 min. A solution of intermediate (4) (0.00264 mol) obtained in Example A2, in THF (20 ml) was added dropwise at −70° C. The mixture was stirred at −70° C. for 1 hour, poured out into ice water and extracted with EtOAc. The organic layer was separated, dried ($MgSO_4$), filtered, and the solvent was evaporated. The residue (2.1 g) was purified by column chromatography over silica gel (eluent: $CH_2Cl_2/CH_3OH/NH_4OH$; 95/5/0.2; 15–40 µm). The pure fractions were collected and the solvent was evaporated. The residue (0.59 g) was crystallized from diethyl-ether. The precipitate was filtered off and dried, yielding 0.49 g (40%) of 4-(3-chlorophenyl)-α-(4-chlorophenyl)-2-methyl-α-(1-methyl-1H-imidazol-5-yl)-6-quinazolinemethanol, mp. 223° C.

Example B14 a) 4-Methyl-4H-1,2,4-triazole-3-thiol (0.0484 mol) was added at −70° C. to THF (230 ml) under $N_2$ flow. n BuLi (0.0969 mol) was added dropwise at −70° C. The mixture was stirred at −70° C. for 1 hour then at 0° C. for 1 hour and cooled to −70° C. (4-chlorophenyl)[4-(3-chlorophenyl)-2-methyl-6-quinolinyl]-methanone (0.0255 mol) described in International Patent Specification WO00/39082 was added portionwise. The mixture was stirred at room temperature for 20 hours, poured out into water and extracted with EtOAc. The organic layer was separated, dried (MgSO$_4$), filtered, and the solvent was evaporated. The residue (13 g, 100%) was purified by column chromatography over silica gel (eluent: CH$_2$Cl$_2$/CH$_3$OH/ NH$_4$OH; 92/8/0.2; 15–35 µm). The pure fractions were collected and the solvent was evaporated, yielding: 8 g (62%) of 4-(3-chlorophenyl)-α-(4-chlorophenyl)-α-(5-mercapto-4-methyl-4H-1,2,4-triazol-3-yl)-2-methyl-6-quinolinemethanol, mp.166° C.

b) Iodomethane (0.0074 mol) was added to a mixture of 4-(3-chlorophenyl)-α-(4-chlorophenyl)-α-(5-mercapto-4methyl-4H-1,2,4-triazol-3-yl)-2-methyl-6-quinolinemethanol (0.0049 mol), obtained in Example B14a, in sodium hydroxide (12.5 ml) and THF (25 ml). the mixture was stirred at room temperature for 2 hours, poured out into water and extracted with EtOAc. The organic layer was separated, dried (MgSO$_4$), filtered, and the solvent was evaporated. The residue (2.5 g, 97%) was purified by column chromatography over silica gel (eluent: CH$_2$Cl$_2$/ CH$_3$OH/NH$_4$OH; 97/3/0.1; 15–40 µm). The pure fractions were collected and the solvent was evaporated. The residue (2.2 g, 86%) was crystallized from 2-propanone/ diethyl ether. The precipitate was filtered off and dried, yielding 2 g (78%) of 4-(3-chlorophenyl)-α-(4-chlorophenyl)-2-methyl-α-[4-methyl-5-(methylthio)-4H-1,2, 4-triazol-3-yl]-6-quinolinemethanol, mp. 142° C.

Example B15

A mixture of 4-(3-chlorophenyl)-α-(4-chlorophenyl)-α- (5-mercapto-4-methyl-4H-1,2,4-triazol-3-yl)-2-methyl-6-quinolinemethanol (0.0020 mol), obtained in Example B14a, in THF (5 ml) was added dropwise at 5° C. to a mixture of sodium nitrite (0.0020 mol) in nitric acid (2 ml) and water (2 ml). The mixture was stirred at 5° C. for 5 minutes, poured out into potassium carbonate 10% and extracted with EtOAc. The organic layer was separated, dried (MgSO$_4$), filtered, and the solvent was evaporated. The residue was purified by column chromatography over kromasil 10 µm (eluent: CH$_2$Cl$_2$/CH$_3$OH; 90/10). The pure fractions were collected and the solvent was evaporated. The residue was crystallized from CH$_3$CN. The precipitate was filtered off and dried, yielding 0.5 g (53%) of 4-(3-chlorophenyl)-α-(4-chlorophenyl)-2-methyl-α-(4-methyl-4H-1, 2,4-triazol-3-yl)-6-quinolinemethanol monohydrate, mp. 150° C.

Example B16 a) A mixture of 4-(3-chorophenyl)-α-(4-chlorophenyl)-2-methyl-α-[4-methyl-5-(methylthio)-4H-1,2,4-triazol-3-yl]-6-quinolinemethanol (0.0019 mol), obtained in Example B14, in thionyl chloride (20 ml) was stirred at 60° C. for 4 hours and then cooled. The solvent was evaporated. The residue was taken up in DCM. The solvent was evaporated till dryness, yielding 6-[chloro(4-chlorophenyl)[4-methyl-5-(methylthio)-4H-1,2,4-triazol-3-yl]methyl]-4-(3-chlorophenyl)-2-methyl-quinoline, monochloride. This product was used without further purification.

b) N$_3$/isopropanol saturated solution (12 ml) was added dropwise at 0° C. to a mixture of 6-[chloro(4-chlorophenyl)[4methyl-5-(methylthio)-4H-1,2,4-triazol-3-yl]methyl]4-(3-chlorophenyl)-2-methyl-quinoline (0.0019 mol) in THF (12 ml). The mixture was stirred at room temperature for 18 hours, poured out into water and extracted with EtOAc. The organic layer was separated, dried (MgSO$_4$), filtered, and the solvent was evaporated. The residue (1.2 g, 100%) was purified by column chromatography over silica gel (eluent: CH$_2$Cl$_2$/CH$_3$OH/N$_4$OH 96/4/0.5). The pure fractions were collected and the solvent was evaporated, yielding 0.78 g (78%) of 4-(3-chlorophenyl)-α-(4-chlorophenyl)-2-methyl-α-[4-methyl-5-(methylthio)-4H-1,2,4-triazol-3-yl]-6-quinolinemethanamine, mp. 128° C.

Example B17

Raney Nickel was added at room temperature to a mixture of 4-(3-chlorophenyl)-α-(4-chlorophenyl)-2-methyl-α-[4-methyl-5-(methylthio)-4H-1,2,4-triazol-3-yl]-6-quinolinemethanamine (0.0012 mol), obtained in Example B16, in 2-propanone (40 ml) under N$_2$ flow. The mixture was stirred at room temperature for 3 hours, filtered over celite, rinsed with DCM and the solvent was evaporated till dryness. The residue was crystallized from diethyl ether. The precipitate was filtered off and dried. The residue (0.31 g, 52%) was purified twice by column chromatography over kromasil (eluent: CH$_3$OH/H$_2$O 80/20 then CH$_3$CN/H$_2$O 35/65; 10 µm). The pure fractions were collected and the solvent was evaporated, yielding 0.13 g (22%) of 4-(3-chlorophenyl)-α- (4-chlorophenyl)-2-methyl-α-(4-methyl-4H-1,2,4-triazol-3-yl)-6-quinolinemethanamine, MS (ESI) m/z: 474 476 478.

Example B18 a) BuLi 1.6M (40 ml) was added dropwise at –70° C. under N$_2$ flow to a mixture of 1-methyl-1H-imidazole (0.0642 mol) in THF (100 ml). The mixture was stirred at –70° C. for 30 min. ClSiEt$_3$ (0.0642 mol) was added. The mixture was brought slowly to 10° C. and cooled again to –70° C. BuLi 1.6M (40 ml) was added dropwise. The mixture was stirred at –70° C. for 1 hour, brought to 40° C. and cooled again to –70° C. A mixture of intermediate (10) (0.0535 mol), obtained in Example A3f, in THF (200 ml) was added. The mixture was stirred at –70° C. for 1 hour, hydrolysed and extracted with EtOAc. The organic layer was separated, dried (MgSO$_4$), filtered and the solvent was evaporated till dryness. The residue (36 g) was purified by column chromatography over silica gel (eluent: CH$_2$Cl$_2$/CH$_3$OH/NH$_4$OH 95.5/4.5/0.2; 20–45 µm). The pure fractions were collected and the solvent was evaporated, yielding 17.6 g (69.5%) of 2-chloro-α-(4-chlorophenyl)-α-(1-methyl-1H-imidazol-5-yl)-4-(3-methylphenyl)-6-quinolinemethanol.

b) A mixture of 2-chloro-α-(4-chlorophenyl)-α-(1-methyl-1H-imidazol-5-yl)-4-(3-methylphenyl)-6-quinolinemethanol, (obtained in stage a) (0.000211 mol) in 2-amino ethanol (1 ml) was heated at 100° C. for 5 hours, then purified by HPLC. The product fractions were collected and the solvent was evaporated, yielding 0.039 g (37%) of α-(4chlorophenyl)-2-[(2-hydroxyethyl)amino]- α-(1-methyl-1H-imidazol-5-yl)-4-(3-methylphenyl)-6-quinolinemethanol, MS (ESI) m/z: 499 501.

Example B19

Raney Nickel (6 g) was added portionwise at room temperature to a mixture of intermediate (11) (0.004 mol) obtained in Example A4, in 2-methyl-2-propanol (20 ml) and water (20 ml). The mixture was stirred at 100° C. for 7 hours, then brought to room temperature and filtered over celite. Celite was washed with EtOAc. The filtrate was extracted with EtOAc. The organic layer was separated, dried (MgSO$_4$), filtered, and the solvent was evaporated. The residue was purified by column chromatography over silica gel (eluent: $CH_2Cl_2/CH_3OH/NH_4OH$ 95/5/0.5; 15–40 µm). The pure fractions were collected and the solvent was evaporated, yielding 1.1 g (57%) of fraction 1. Part of this fraction 1 (0.3 g) was crystallized from $CH_3CN/EtOH$. The precipitate was filtered off and dried under a vacuum, yielding 0.2 g of 2-amino-4-(3-chlorophenyl)-α-(4-chlorophenyl)-α-(1-methyl-1H-imidazol-5-yl)-6-quinazolinemethanol, mp. 235° C.

Example B20

A mixture of intermediate (11) (0.0131 mol), obtained in Example A4, and oxo-acetic acid, ethyl ester (0.0170 mol) in dioxane (65 ml) was stirred at 100° C. for 2 hours, poured out into water and extracted with DCM. The organic layer was separated, dried ($MgSO_4$), filtered, and the solvent was evaporated till dryness. Part of the residue (0.75 g) was purified by column chromatography over silica gel (eluent: $CH_2Cl_2/CH_3OH/NH_4OH$ 90/10/0.5; 15–40 µm). Two fractions F1 and F2 were collected and the solvent was evaporated. The first fraction was crystallized from CH3CN/DIPE. The precipitate was filtered off and dried, yielding 0.23 g (31%) of (A)-ethyl [[4-(3-chlorophenyl)-6-[(4-chlorophenyl)hydroxy(1-methyl-1H-imidazol-5-yl)methyl]-2-quinazolinyl]hydrazono]-(2E)-ethanoate, mp. 222° C. The second fraction was crystallized from DIPE. The precipitate was filtered off and dried, yielding 0.26 g (35%) of (B)-ethyl [[4-(3-chlorophenyl)-6-[(4-chlorophenyl)hydroxy(1-methyl-1H-imidazol-5-yl)methyl]-2-quinazolinyl]hydrazono]-(2E)-ethanoate, mp. 170° C.

Example B21

A mixture of 2-amino-4-(3-chlorophenyl)-α-(4-chlorophenyl)-α-(1-methyl-1H-imidazol-5-yl)-6-quinazolinemethanol (0.00021 mol), obtained in Example B19, and 1-isothiocyanato-2-methoxy-ethane (3 equiv, 0.00063 mol) in THF (1 ml) was heated at 60° C. for 5 hours. A few drops of water were added. The mixture was evaporated till dryness and purified by HPLC. The pure fractions were collected and the solvent was evaporated, yielding 0.003 g (2.4%) of N-[4-(3-chlorophenyl)-6-[(4-chlorophenyl)hydroxy(1-methyl-1H-imidazol-5-yl)methyl]-2-quinazolinyl]-N'-(2-methoxyethyl)-thiourea, MS(ESI) m/z: 593 595 597.

Example B22

A mixture of 2-amino-4-(3-chlorophenyl)-α-(4-chlorophenyl)-α-(1-methyl-1H-imidazol-5-yl)-6-quinazolinemethanol (0.00021 mol) obtained in Example B19, and 2-isocyanato-propane (3 equiv, 0.00063 mol) in THF (1 ml) was heated at 60° C. for 5 hours. A few drops of water were added. The mixture was evaporated till dryness and purified by HPLC. The product fractions were collected and the solvent was evaporated, yielding 0.024 g (20.3%) of N-[4-(3-chlorophenyl)-6-[(4-chlorophenyl)hydroxy(1-methyl-1H-imidazol-5-yl)methyl]-2-quinazolinyl]-N'-(1-methylethyl)-urea, MS (ESI) m/z: 561 563 565.

Example B23

A mixture of 2-amino-4-(3-chlorophenyl)-α-(4-chlorophenyl)-α-(1-methyl-1H-imidazol-5-yl)-6-quinazolinemethanol (0.00021 mol), obtained in Example B19, cyclohexanecarboxylic acid (1.2 equiv, 0.000252 mol), N'-(ethylcarbonimidoyl)-N,N-dimethyl-1,3-propanediamine, monohydrochloride (1.5 equiv, 0.000315 mol), 1-hydroxy-1H-benzotriazole (1.5 equiv, 0.000315 mol) and triethylamine (1.5 equiv, 0.000315 mol) in THF (2 ml) was stirred at room temperature for 18 hours, then taken up in water. The organic layer was separated and the solvent was evaporated. The residue was purified by HPLC. The product fractions were collected and the solvent was evaporated, yielding 0.006 g (4.8%) of N-[4-(3-chlorophenyl)-6-[(4-chlorophenyl)hydroxy(1-methyl-1H-imidazol-5-yl)methyl]-2-quinazolinyl]-cyclohexanecarboxamide, MS (ESI) m/z: 586 588 590.

Example B24

A mixture of intermediate (15) (0.000213 mol) obtained in Example A5d, 1-amine-2-propene (2.5 equiv, 0.000533 mol) and HOAc (1 drop) in acetonitrile (2 ml) was stirred at room temperature for 2 hours. Then $NaBH_3CN$ (2.5 equiv, 0.000533 mol) was added. The mixture was stirred overnight at room temperature. After addition of water and evaporation, the residue was purified by HPLC. The product fractions were collected and the solvent was evaporated yielding 0.006 g (5.5%) of 4-(3-chlorophenyl)-6-[(4-chlorophenyl)-3-pyridinylmethyl]-N-(2-propenyl)-2-quinolinemethanamine, MS (ESI) m/z: 510 512 514.

Example B25

A mixture of ethynyl-benzene (0.0021 mol), $Pd(PPh_3)_2Cl_2$ (0.0002 mol) and copper (I) iodide (0.0002 mol) was added at room temperature to a mixture of (±)-2-chloro-4-(3-chlorophenyl)-α-(4-chlorophenyl)-α-(1-methyl-1H-imidazol-5-yl)-6-quinolinemethanol (0.0014 mol), described in International Patent Specification WO 00/39082, in N-ethyl-ethanamine (7ml) and DMF (7 ml) under $N_2$ flow. The mixture was stirred at room temperature overnight, then at room temperature for 3 days, poured out into ice water and extracted with EtOAc. The organic layer was separated, washed three times with water, dried ($MgSO_4$), filtered and the solvent was evaporated. The residue (1.2 g) was purified by column chromatography over silica gel (eluent: $CH_2Cl_2$ 100 to $CH_2Cl_2/CH_3OH$ 98/2 98/2; 35–70 µm). The pure fractions were collected and the solvent was evaporated, yielding 0.5 g of a fraction which was taken up in diethyl ether. The precipitate was filtered off and dried. The residue (0.28 g) was purified by column chromatography over kromasil (eluent: $CH_3CN/CH_3COONH_4$ 1% 75/25; 10 µm). The pure fractions were collected and the solvent was evaporated, yielding: 0.279 g of a product which was dried at 90° C. in a vacuum for 4 hours, yielding 0.14 g (18%) of 4-(3-chlorophenyl)-α-(4-chlorophenyl)-α-(1-methyl-1H-imidazol-5-yl)-2-(phenylethynyl)-6-quinolinemethanol, mp. 154° C.

Example B26

A mixture of 2-chloro-4-(3-chlorophenyl)-α-(4-chlorophenyl)-α-(1-methyl-1H-imidazol-5-yl)-6-quinazolinemethanol (0.0051 mol), described in International Patent Specification WO 00/39082, 3-pyridinyl-boronic acid (0.0077 mol) and $Pd(PPh_3)_2Cl_2$ (0.001 mol) in sodium carbonate 2M (25 ml) and dioxane (25 ml) was stirred at 115° C. for 3 hours, then cooled, poured out into ice water and extracted with DCM. The organic layer was separated, dried ($MgSO_4$), filtered, and the solvent was evaporated. The residue was purified by column chromatography over silica gel (eluent: $CH_2Cl_2/CH_3OH/NH_4OH$ 97/3/0.1; 15–40 µm). The pure fractions were collected and the solvent was evaporated, yielding 1.02 g of a fraction which was crystallized from CH₃CN. The precipitate was filtered off and dried, yielding 0.7 g (36%) of 4-(3-chlorophenyl)-α-(4-chlorophenyl)-α-(1-methyl-1H-imidazol-5-yl)-2-(3-pyridinyl)-6-quinazolinemethanol, mp.178° C.

The following compounds were prepared analogous to one of the above examples (the example number analogous to which they were prepared is indicated between square brackets). Mass spectral data (ms) is given for MH+ peaks, determined by electron spray ionisation (ESI)

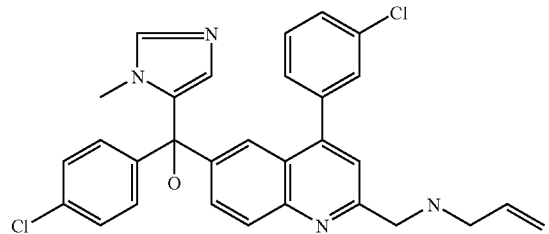

[Br] ms. 529 531 533

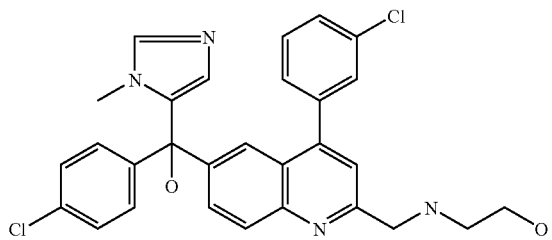

[B4] ms. 533 535 537

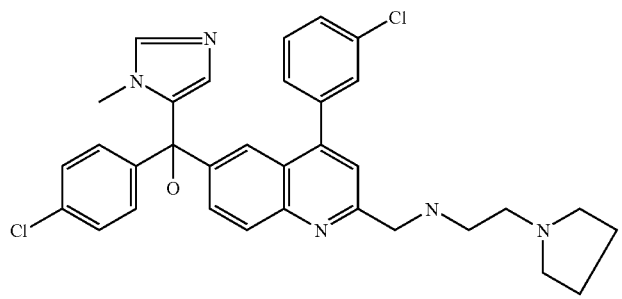

[B4] ms. 586 588 590

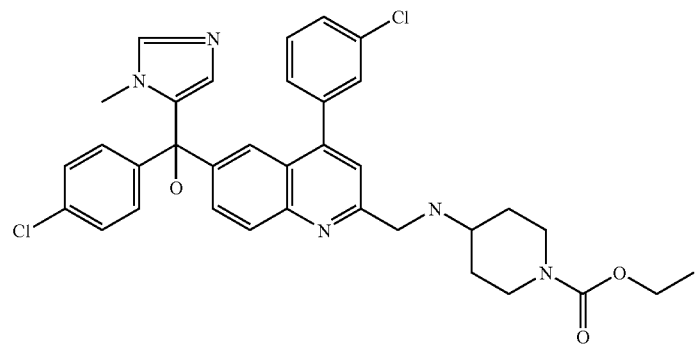

[B4] ms. 644 646 648

-continued
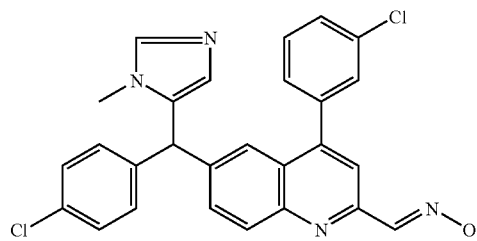
[B1]; mp. 191° C.
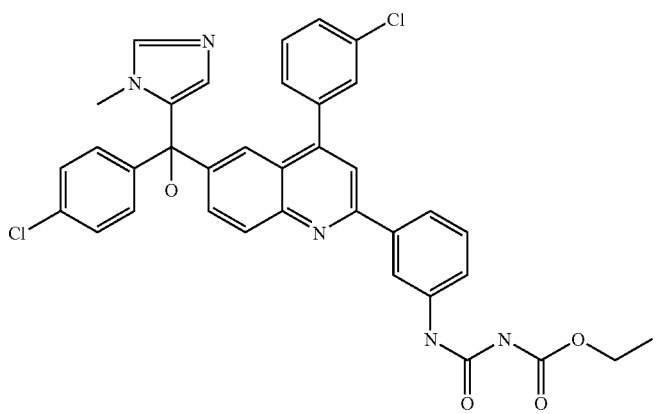
[B9]; mp. 80° C.
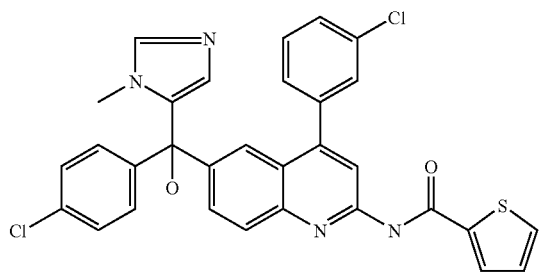
[B8] ms. 585 587 589
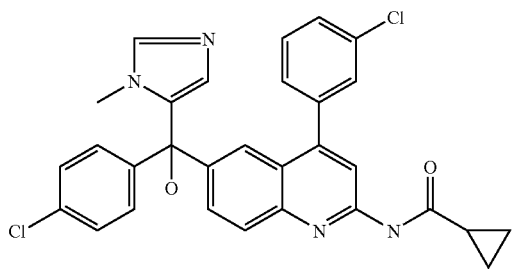
[B8] ms. 543 545 547

-continued
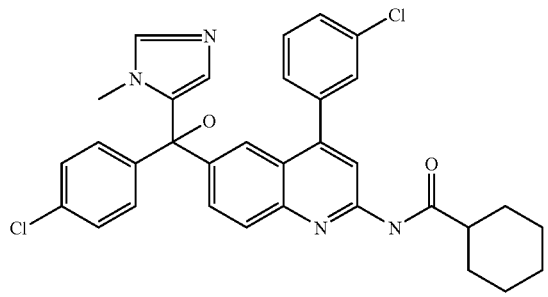
[B8] ms. 585 587 589
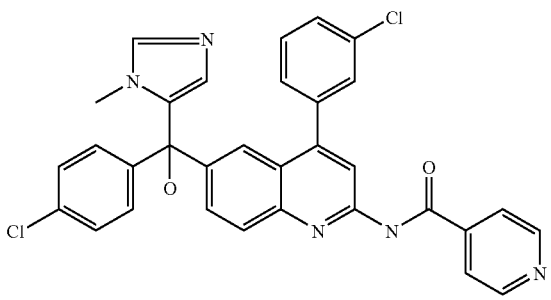
[B8] ms. 580 582 584
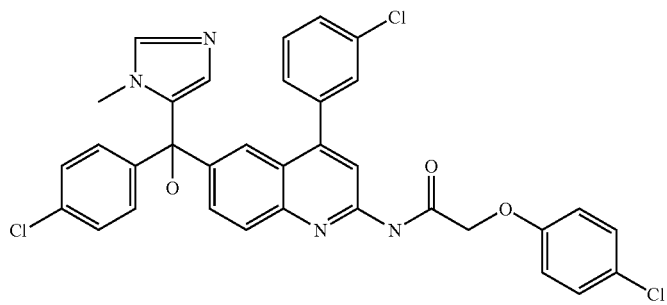
[B8] ms. 643 645 647 649
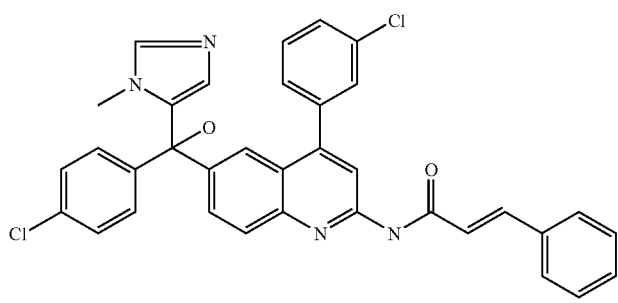
(E) [B8] ms. 605 607 609
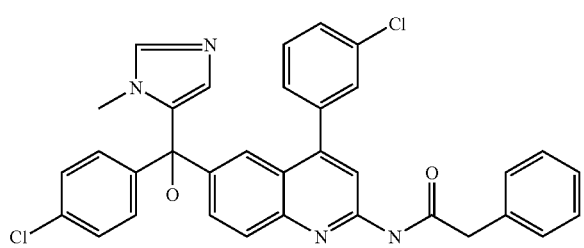
[B8] ms. 593 595 597

-continued
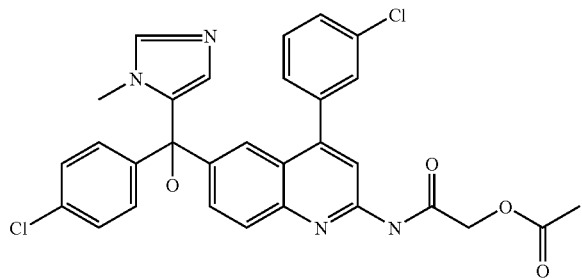
[B8] ms. 575 577 579
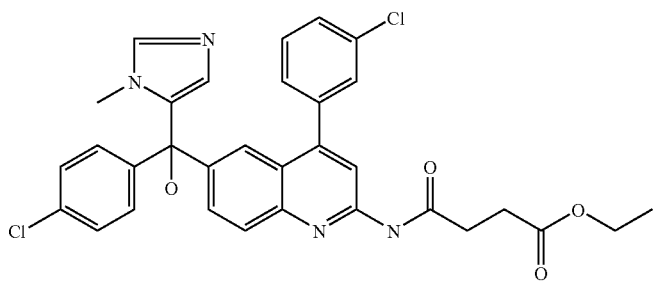
[B8] ms. 575 577 579
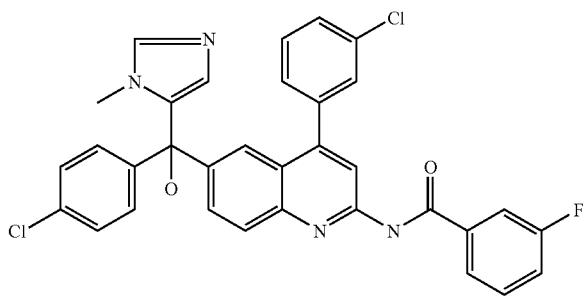
[B8] ms. 597 599 601
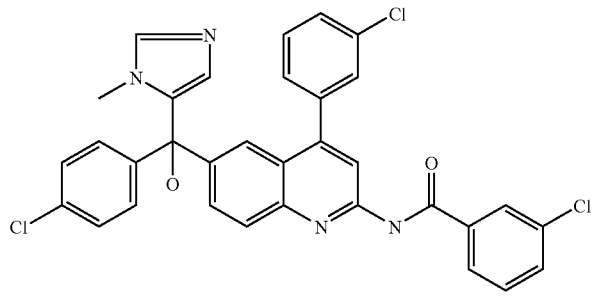
[B8] ms. 613 615 617 619

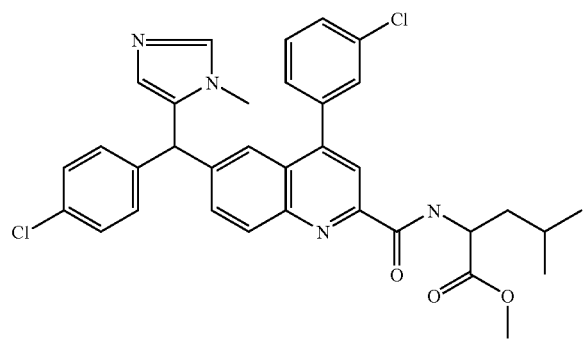
[B7] ms. 615 617 619
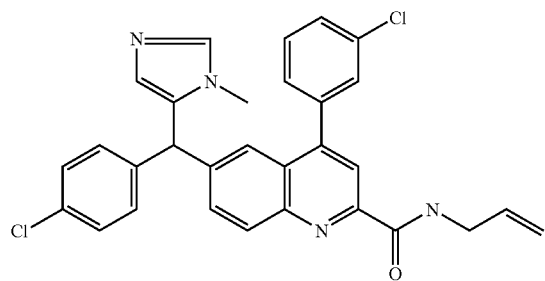
[B7] ms. 527 529 531
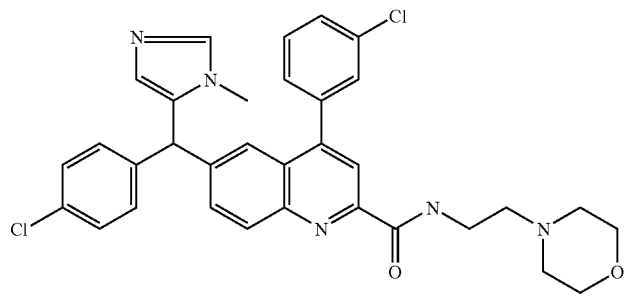
[B7] ms. 600 602 604
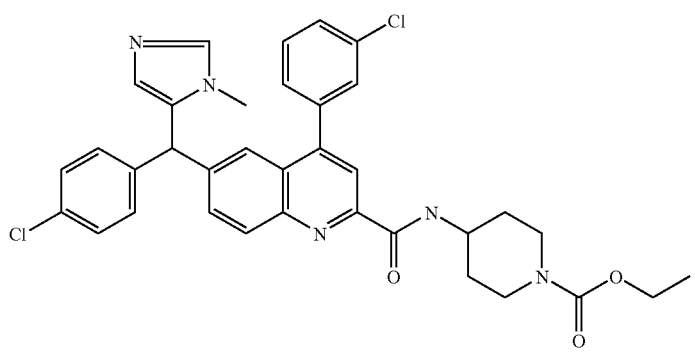
[B7] ms. 642 644 646

-continued
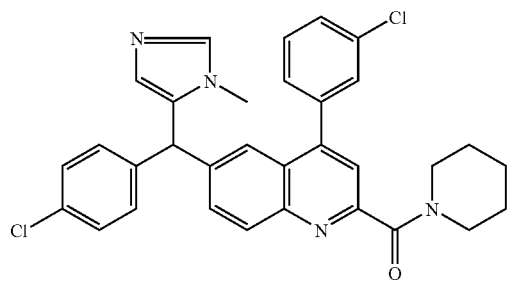
[B7] ms. 555 557 559
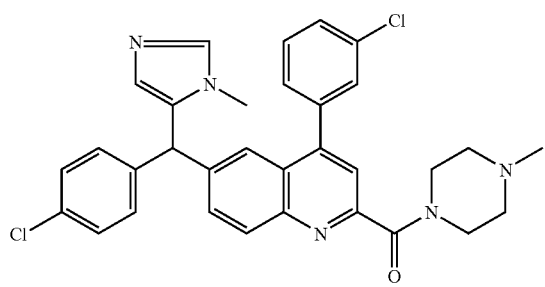
[B7] ms. 570 572 574
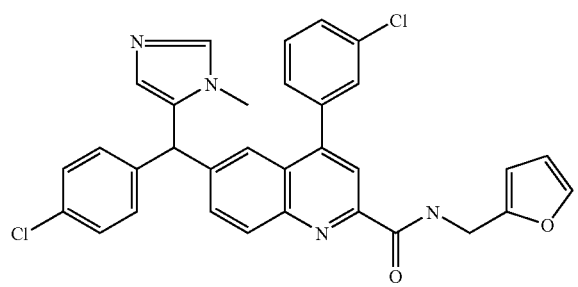
[B7] ms. 567 569 571
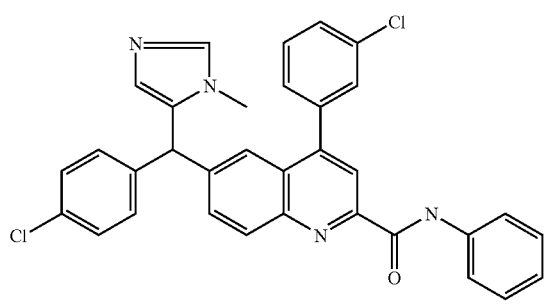
[B7] ms. 563 565 567

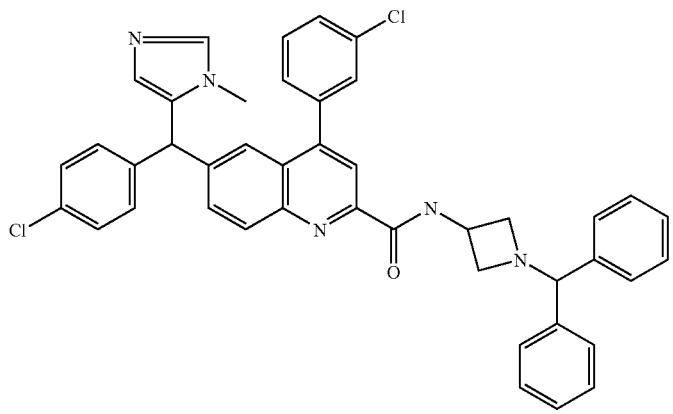
[B7] ms. 708 710 712
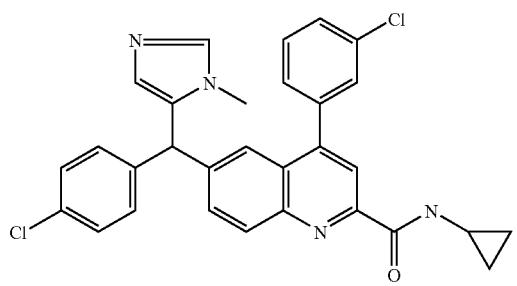
[B7] ms. 527 529 531
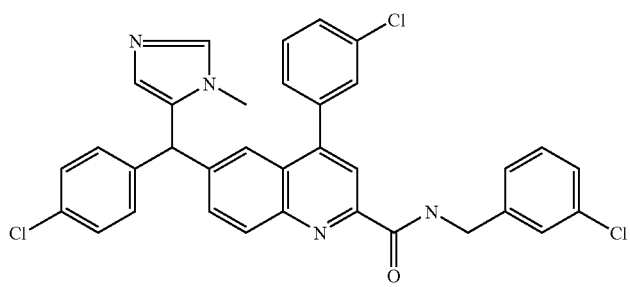
[B7] ms. 611 613 615 617
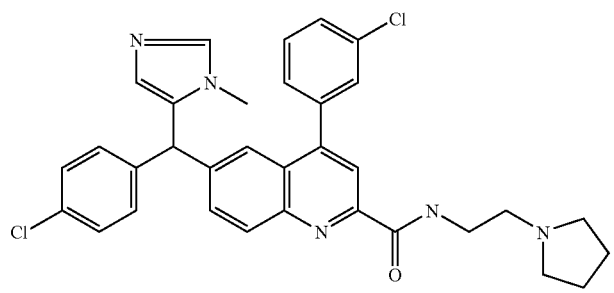
[B7] ms. 584 586 588

-continued
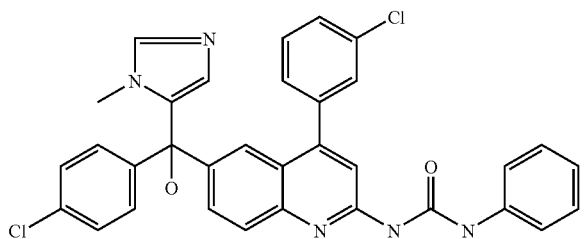
[B9] ms. 594 596 598
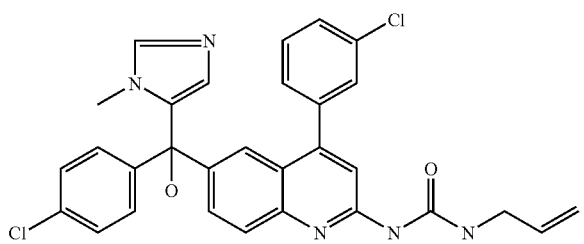
[B9] ms. 558 560 562
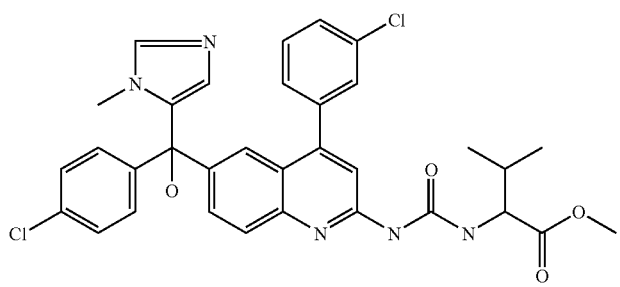
[B9] ms. 632 634 636
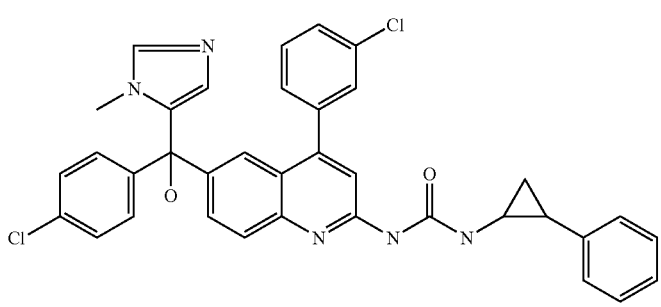
[B9] ms. 634 636 638
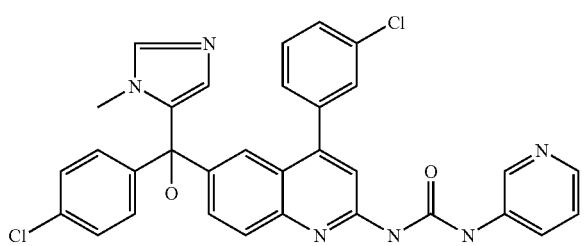
[B9] ms. 595 597 599

-continued
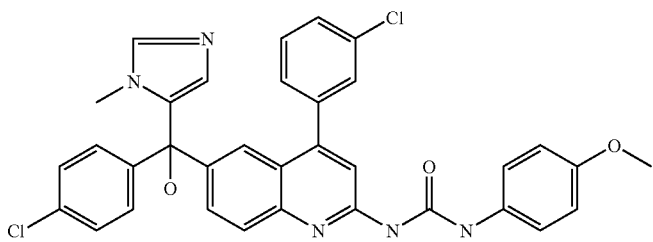
[B9] ms. 624 626 628
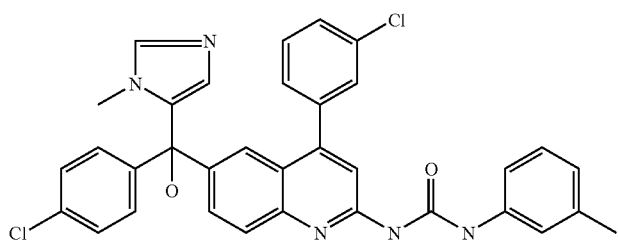
[B9] ms. 608 610 612
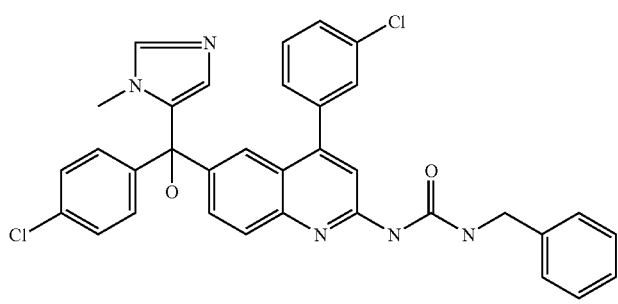
[B9] ms. 608 610 612
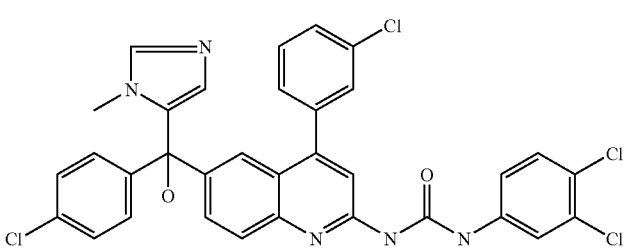
[B9] ms. 662 664 666 668 670
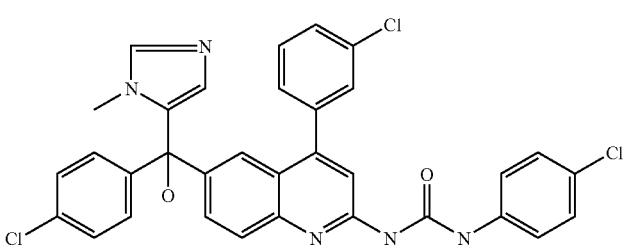
[B9] ms. 628 630 632 634

-continued
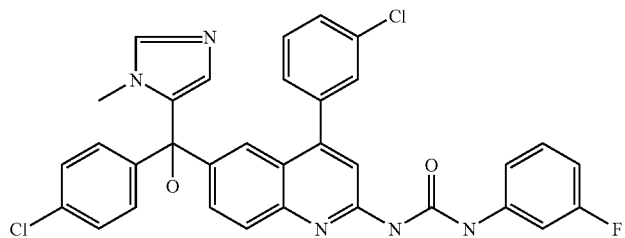
[B9] ms. 612 614 616 670
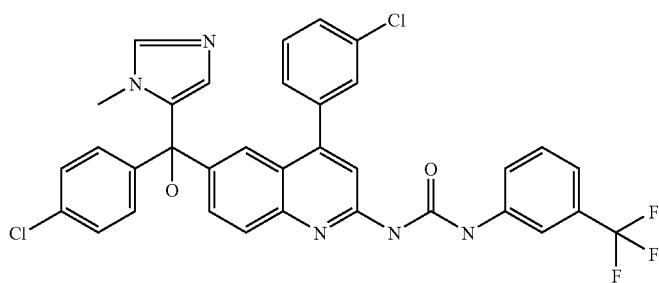
[B9] ms. 662 664 666
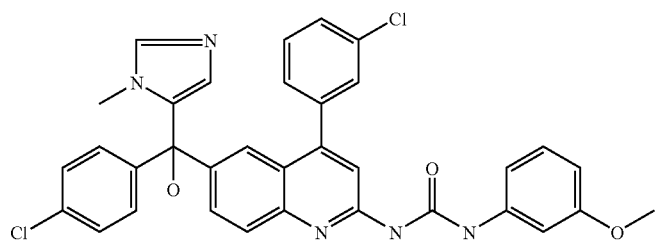
[B9] ms. 624 626 628
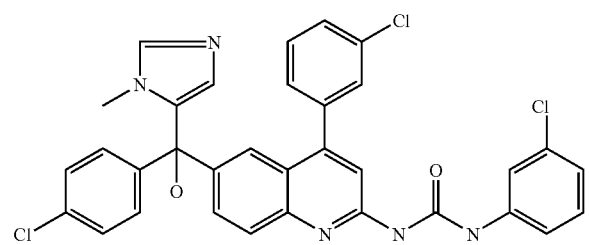
[B9] ms. 628 630 632 634
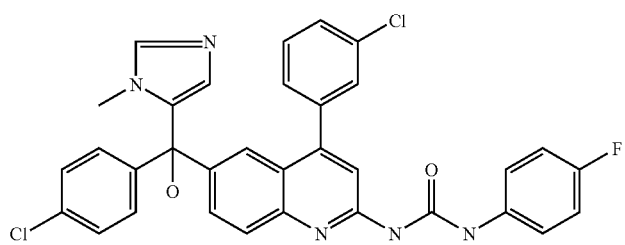
[B9] ms. 612 614 616

-continued
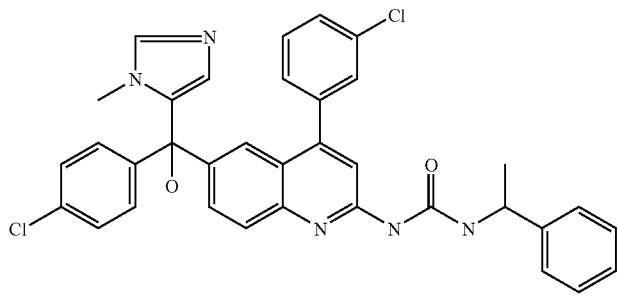
[B9] ms. 622 624 626
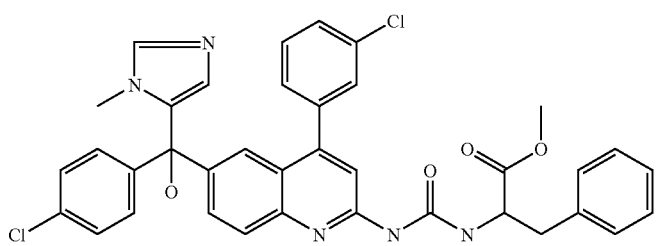
[B9] ms. 680 682 684
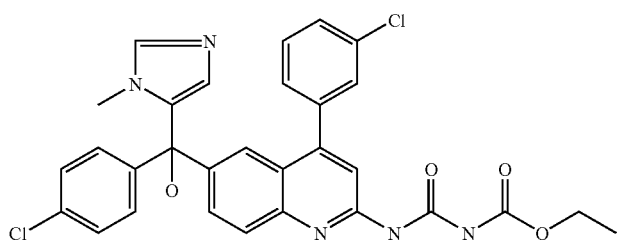
[B9] ms. 590 592 594
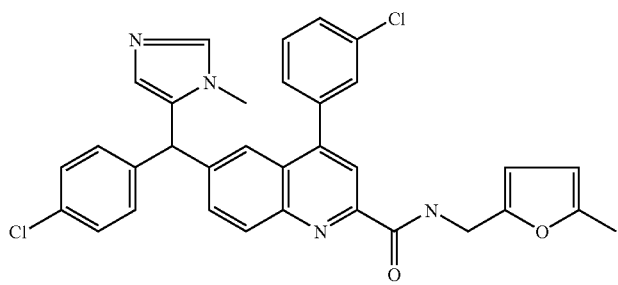
[B7] ms. 581 593 585
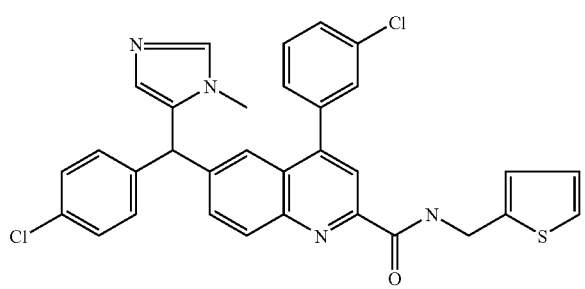
[B7] ms. 583 585 587

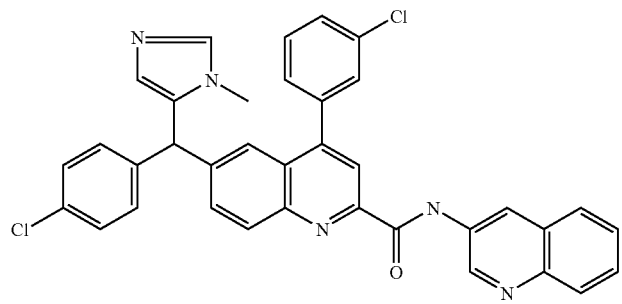
[B7] ms. 614 616 618
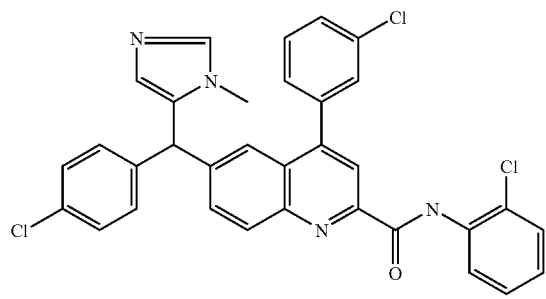
[B7] ms. 598 600 602 604
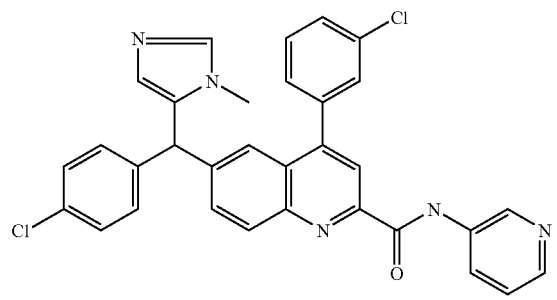
[B7] ms. 564 566 568
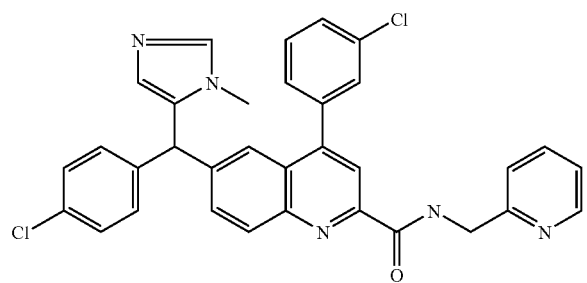
[B7] ms. 578 580 582

-continued
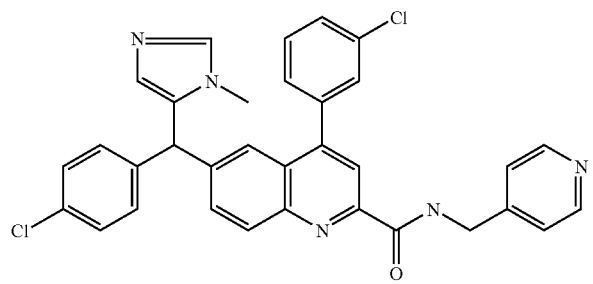
[B7] ms. 578 580 582
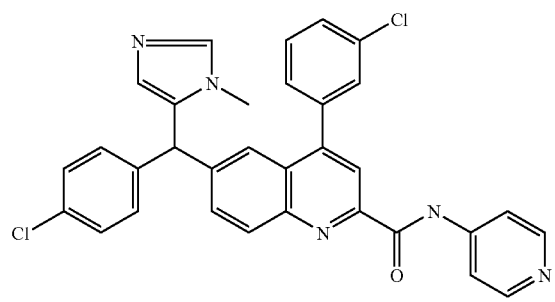
[B7] ms. 564 566 568
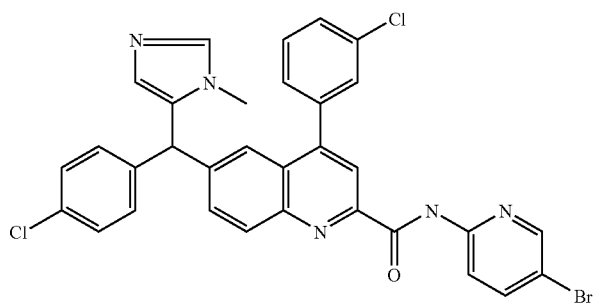
[B7] ms. 642 644 646 648
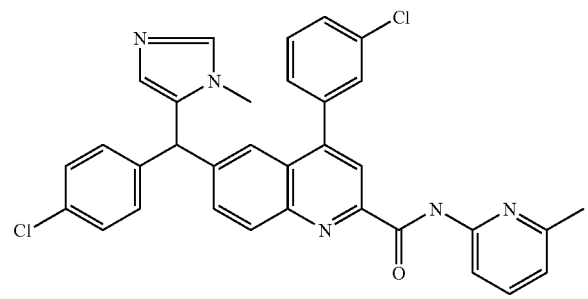
[B7] ms. 578 580 582

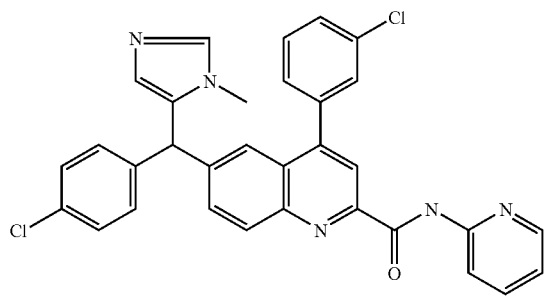
[B7] ms.n 564 566 568
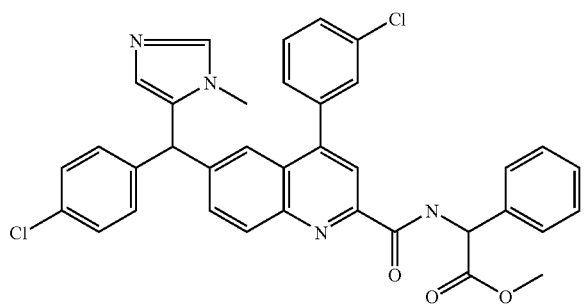
[S−(R*,R*)] + [S−(R*,S*)]
[B7] ms. 635 637 639
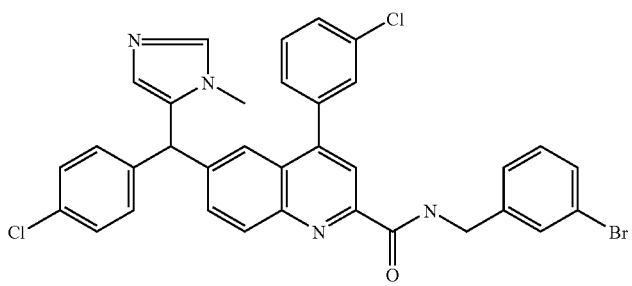
[B7] ms. 655 657 659 661
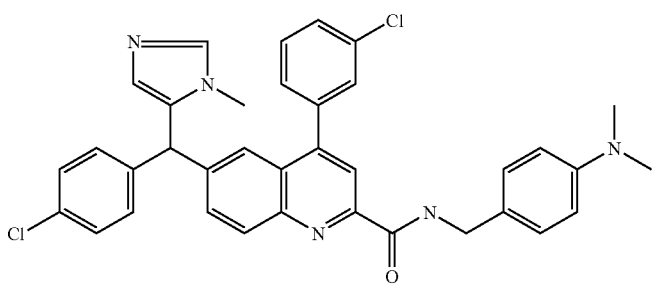
[B7] ms. 620 622 624

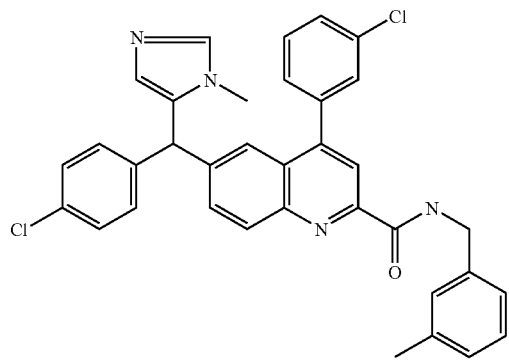
[B7] ms. 591 593 595
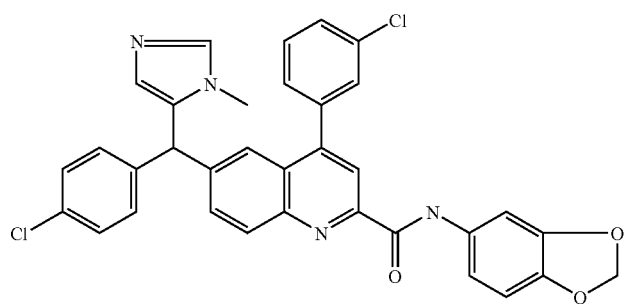
[B7] ms. 607 609 611
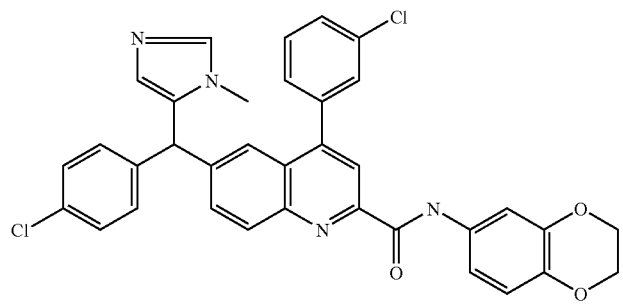
[B7] ms. 621 623 625
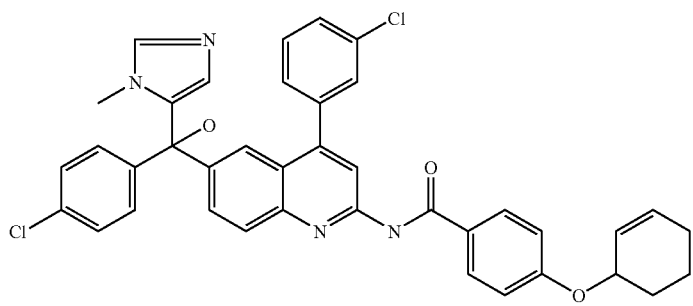
[B10] ms. 675 677 679

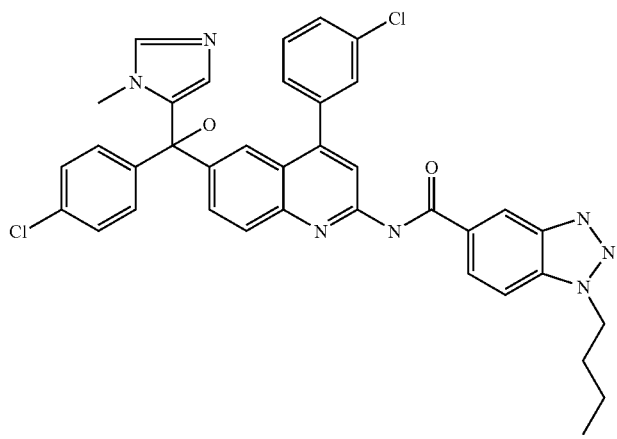
[B10] ms. 676 678 680
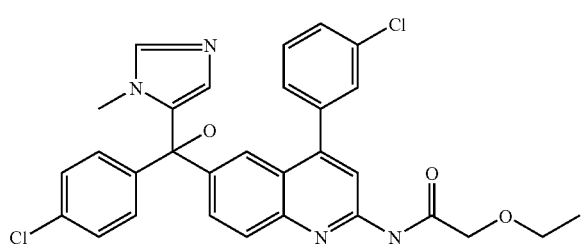
[B10] ms. 561 563 565
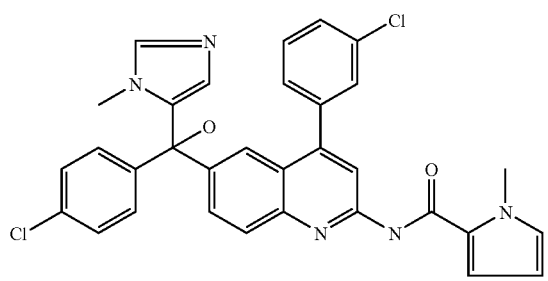
[B10] ms. 582 584 586
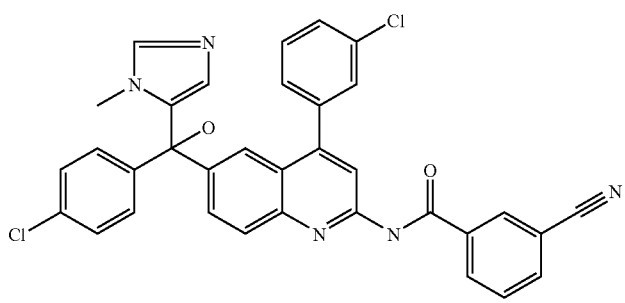
[B10] ms. 604 606 608

-continued
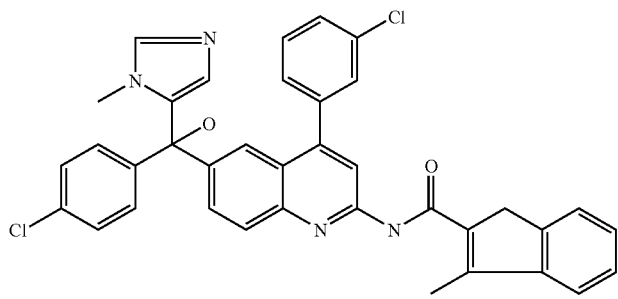
[B10] ms. 631 633 635
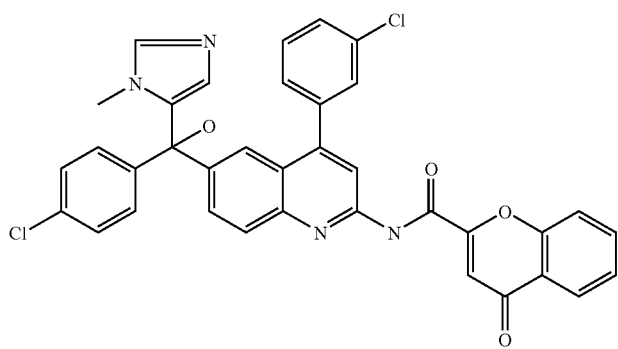
[B10] ms. 647 649 651
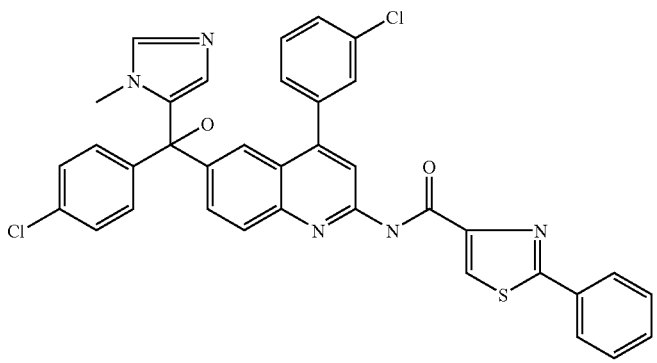
[B10] ms. 662 664 666
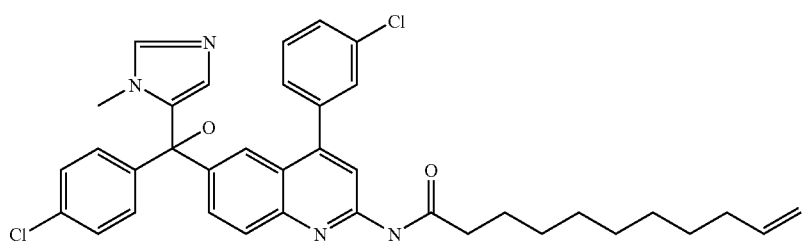
[B10] ms. 641 643 645

-continued
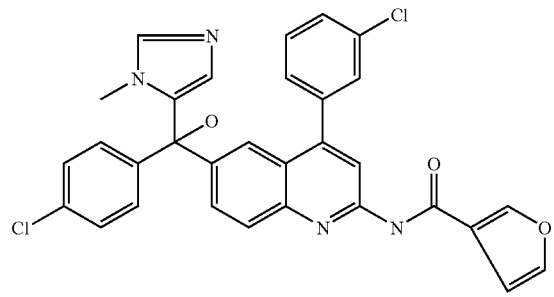
[B10] ms. 569 571 573
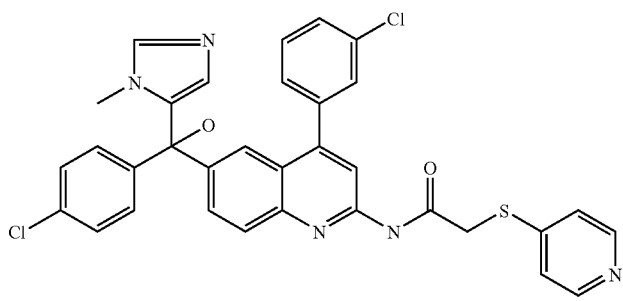
[B10] ms. 626 628 630
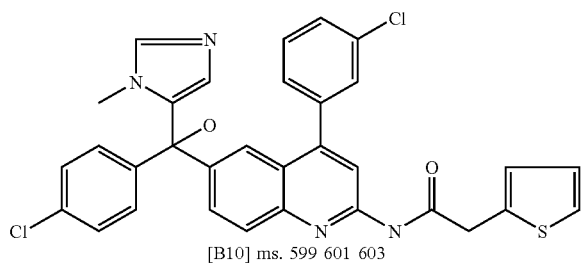
[B10] ms. 599 601 603
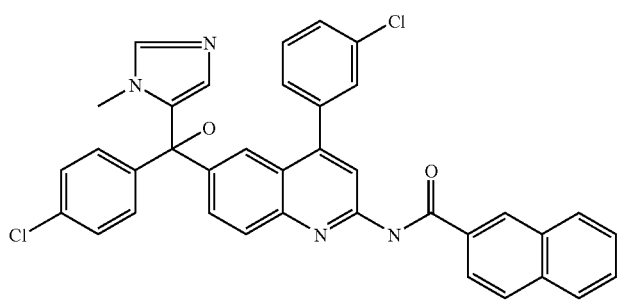
[B10] ms. 629 631 633
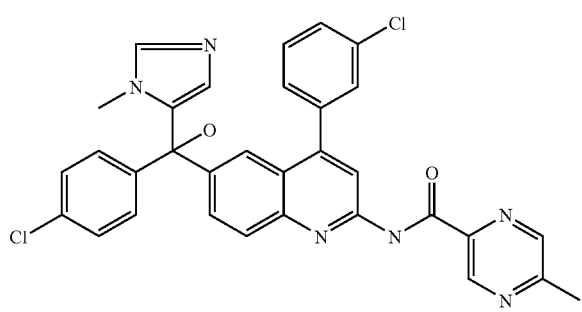
[B10] ms. 595 597 599

-continued
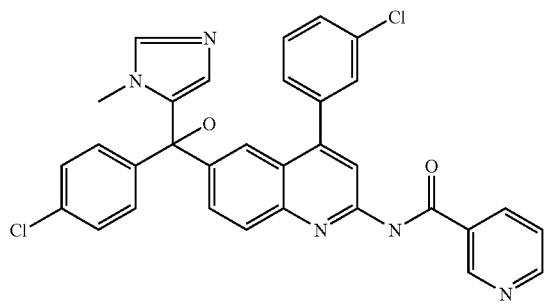
[B10] ms. 580 582 584
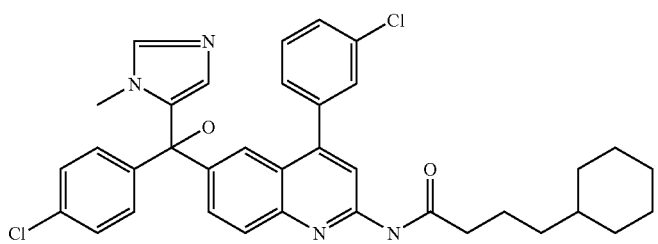
[B10] ms. 627 629 631
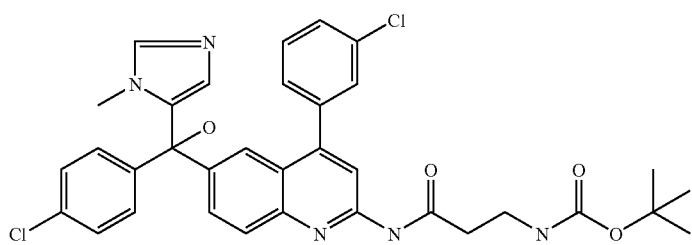
[B10] ms. 646 648 650
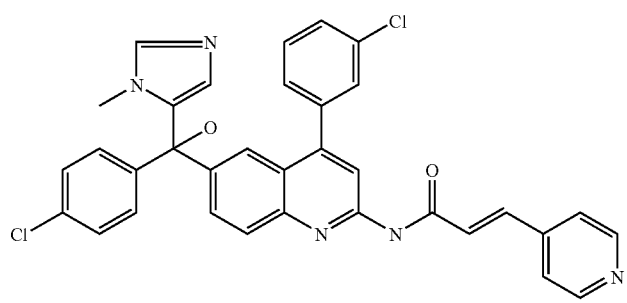
[B10] ms. 606 608 610
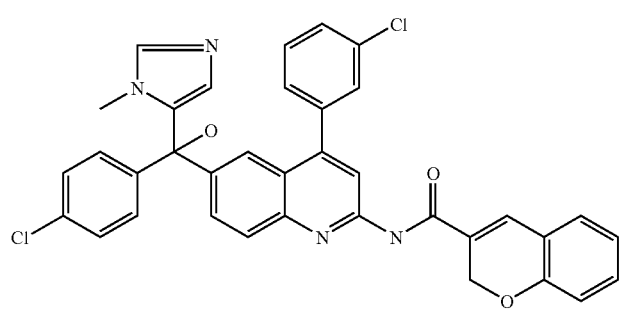
[B10] ms. 633 635 637

-continued
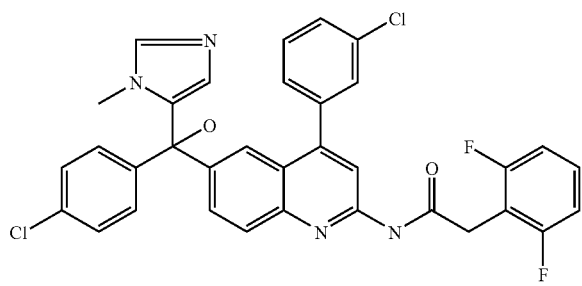
[B10] ms. 629 631 633
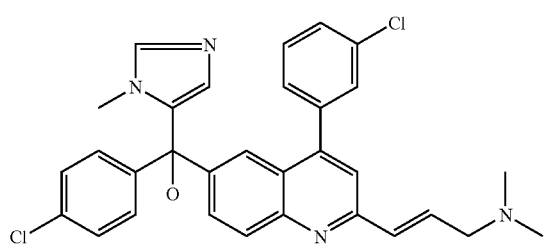
(E) [B2]; mp. 80° C.
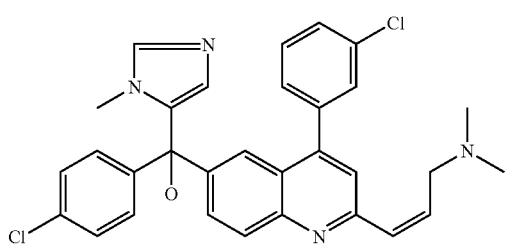
(Z) [B2]; mp. 80° C.
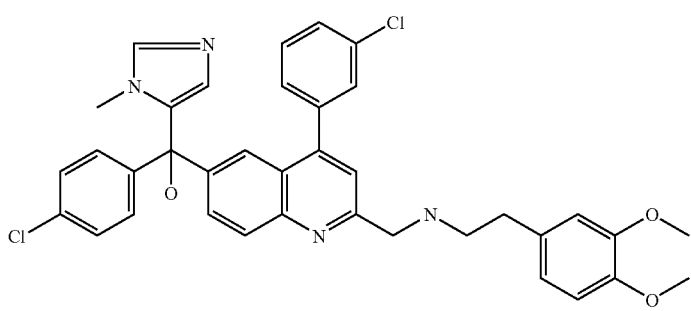
[B4] ms. 653 655 657
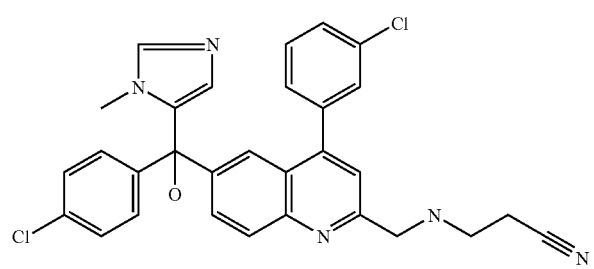
[B4] ms. 542 544 546

-continued
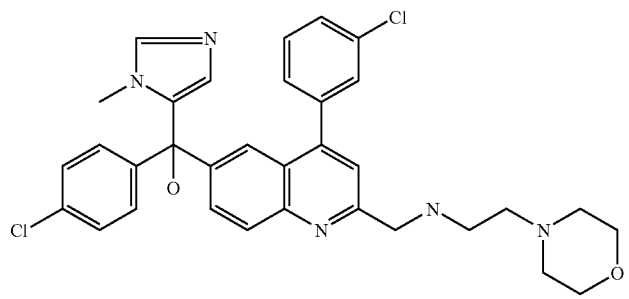
[B4] ms. 602 604 606
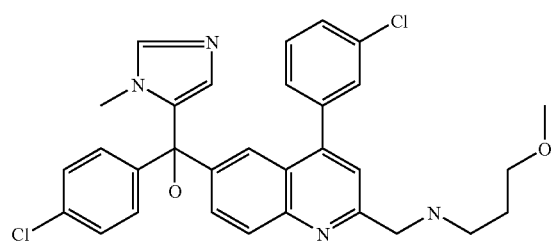
[B4] ms. 561 563 5654
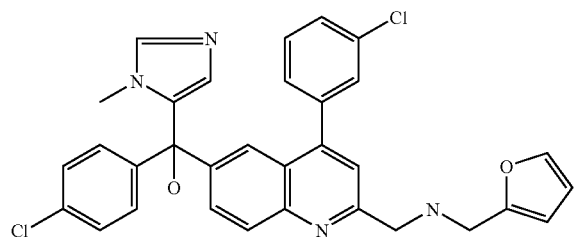
[B4] ms. 569 571 573
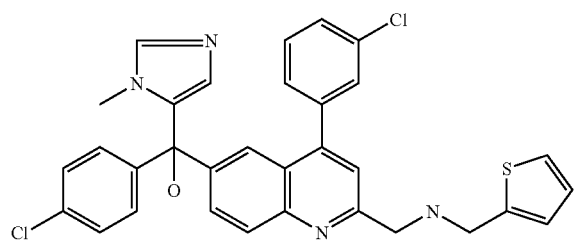
[B4] ms. 585 587 589
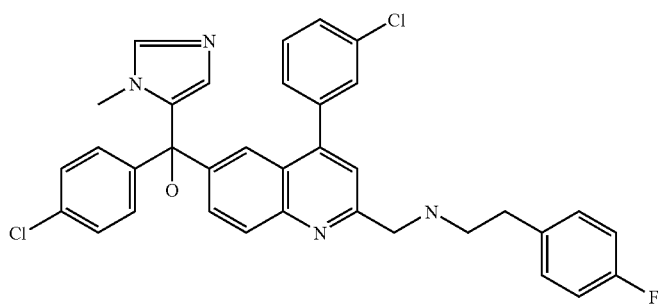
[B4] ms. 611 613 615

-continued
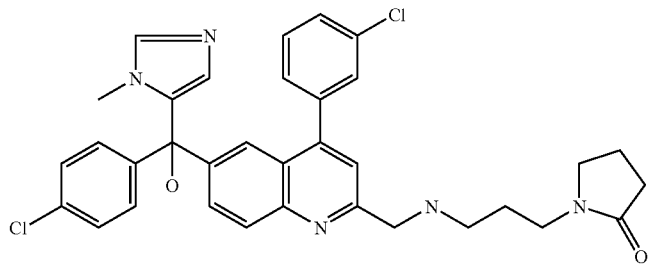
[B4] ms. 614 616 618
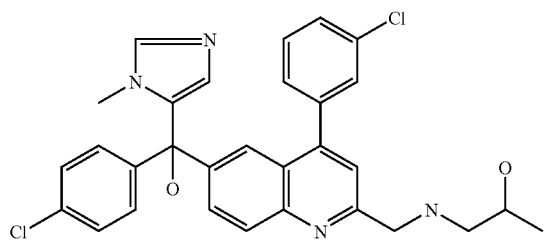
[B4] ms. 547 549 551
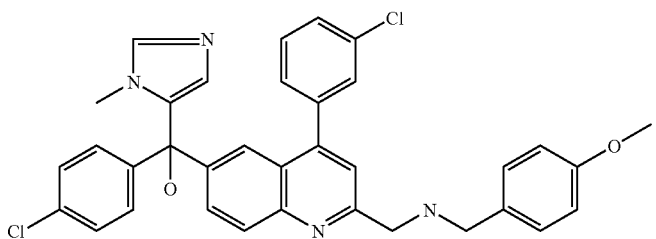
[B4] ms. 609 611 613
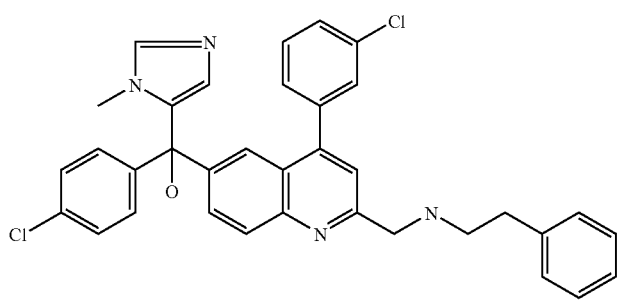
[B4] ms. 593 595 597
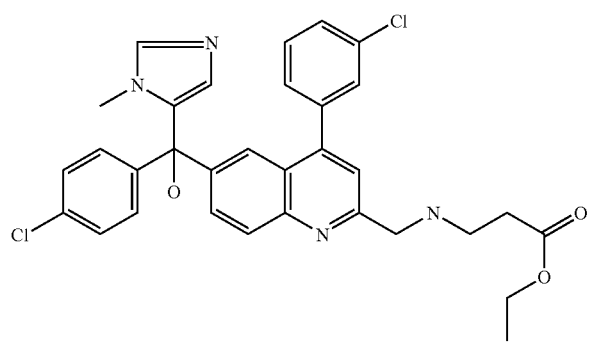
[B4] ms. 589 591 593

-continued
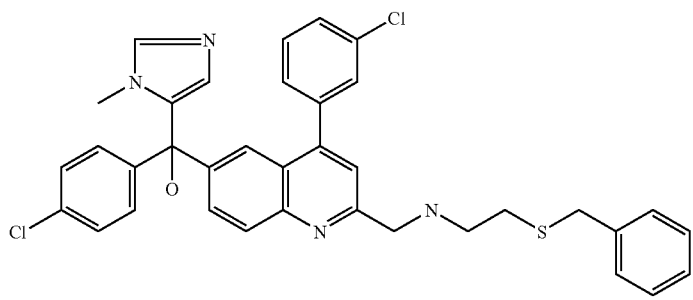
[B4] ms. 639 641 643
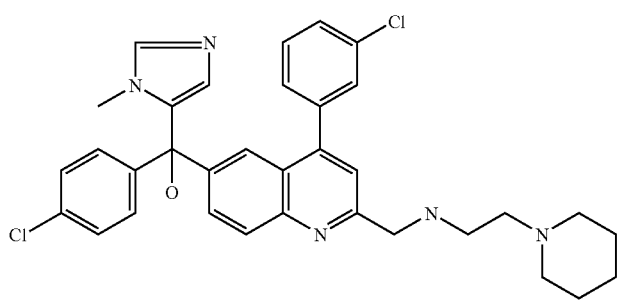
[B4] ms. 600 602 604
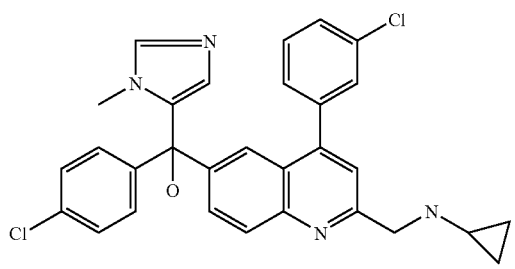
[B4] ms. 529 531 533
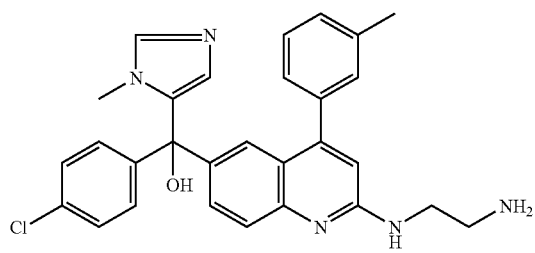
[B18] ms. 498 500
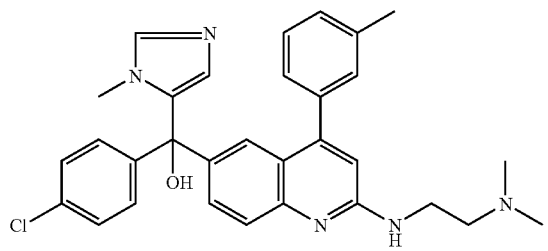
[B18] ms. 526 528

-continued
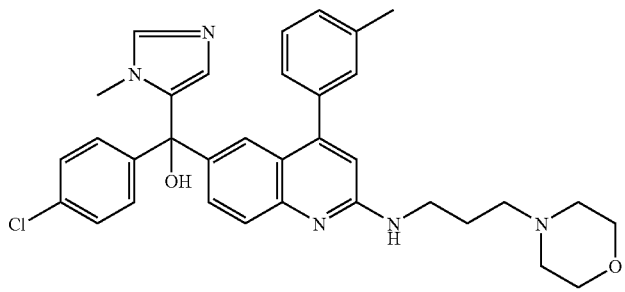
[B18] ms. 582 584
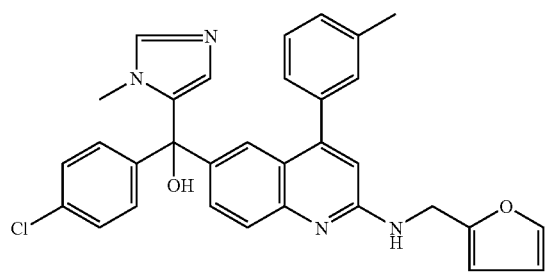
[B18] ms. 535 537
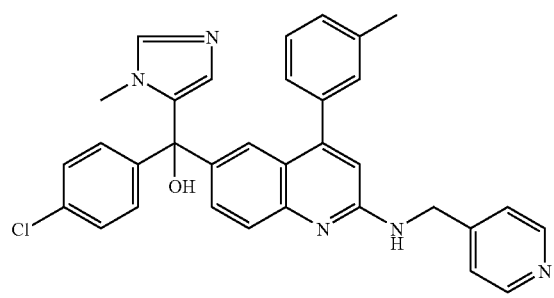
[B18] ms. 546 548
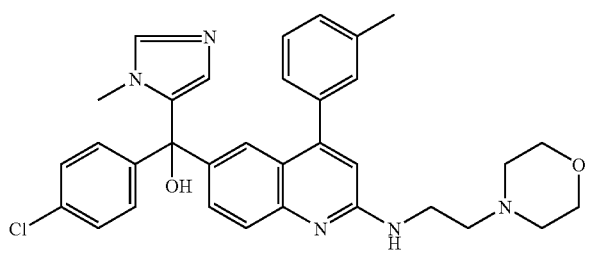
[B18] ms. 568 570
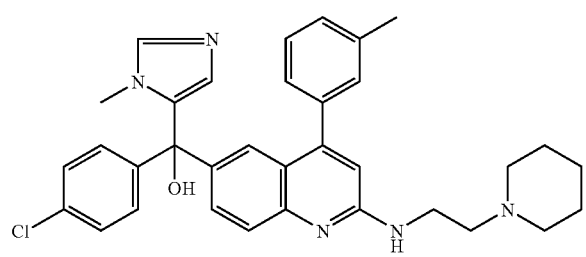
[B18] ms. 566 568

-continued
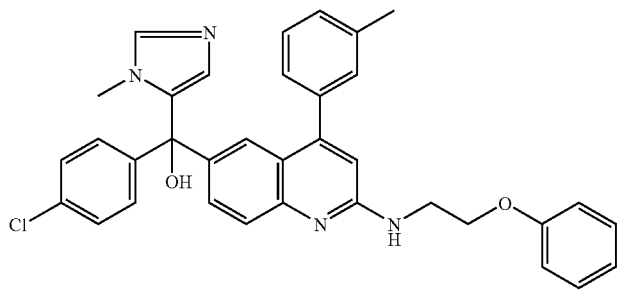
[B18] ms. 575 577
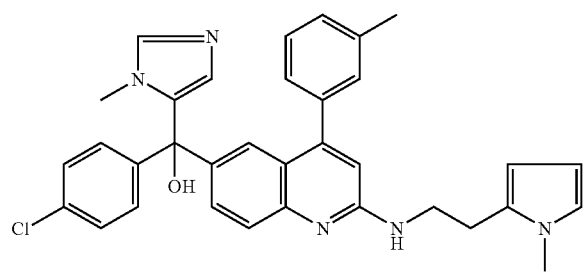
[B18] ms. 562 564
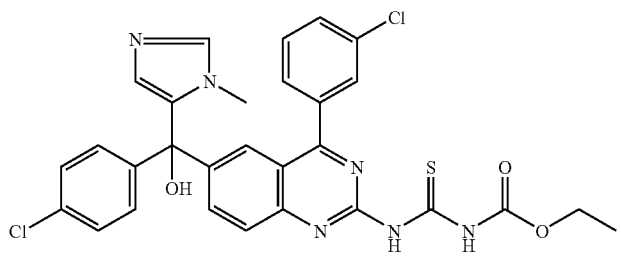
[B21] ms. 607 609 611
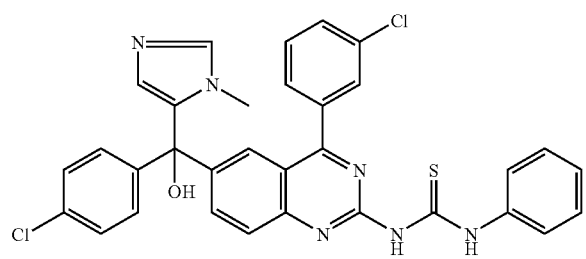
[B21] ms. 611 613 615
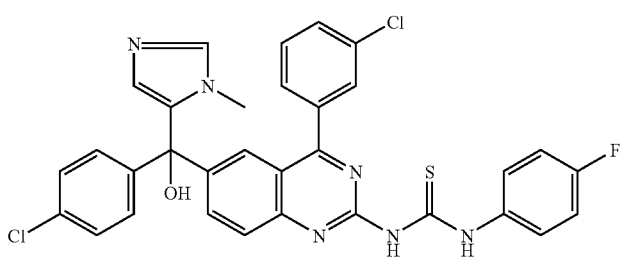
[B21] ms. 629 631 633

-continued
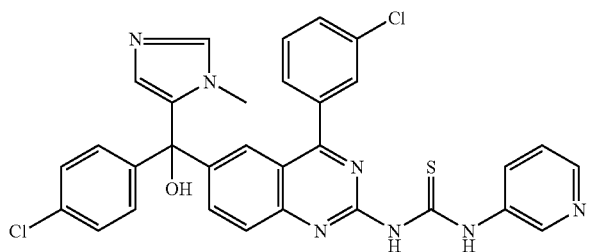
[B21] ms. 612 614 616
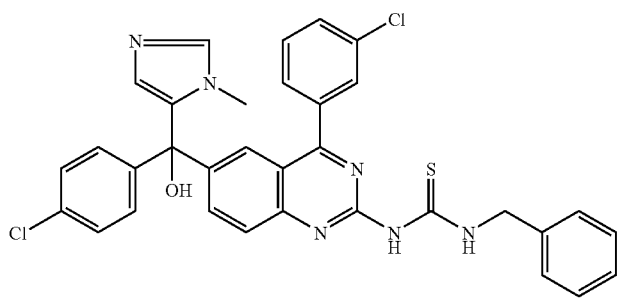
[B21] ms. 625 627 629
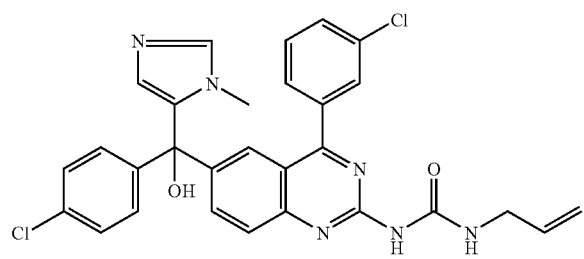
[B22] ms. 559 561 563
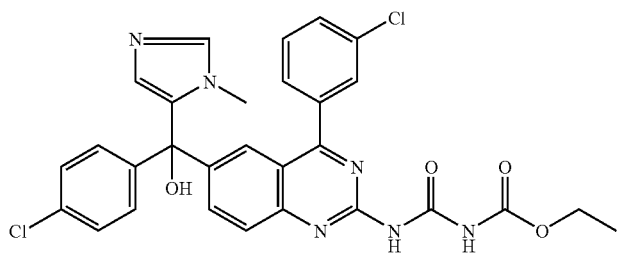
[B22] ms. 591 593 595
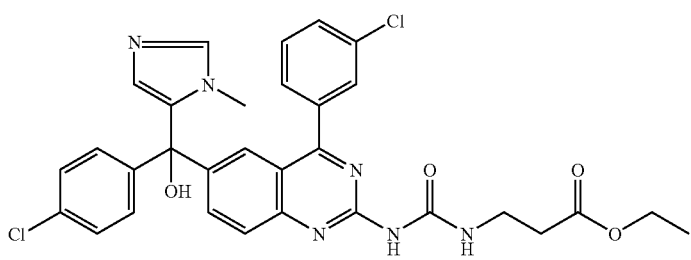
[B22] ms. 619 621 623

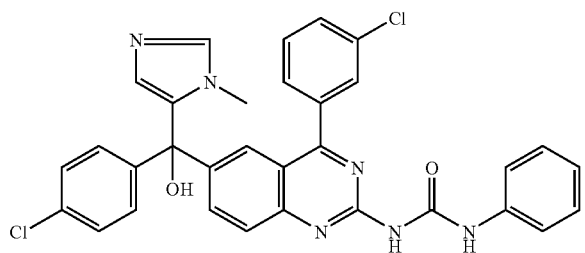
[B22] ms. 595 597 599
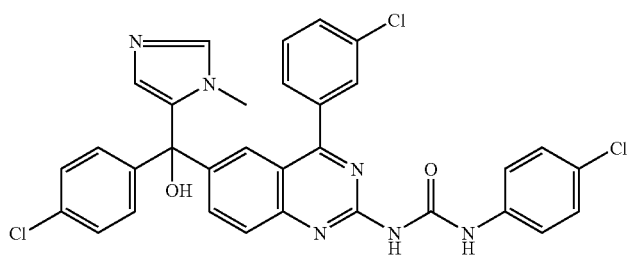
[B22] ms. 629 631 633 635
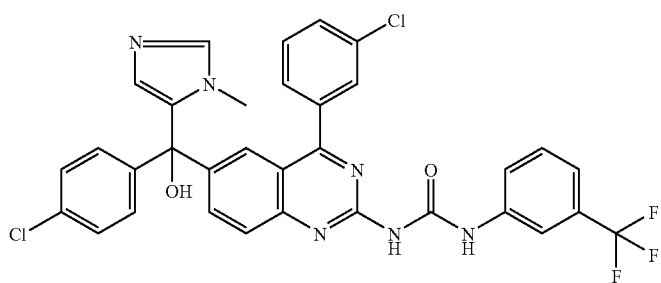
[B22] ms. 663 665 667
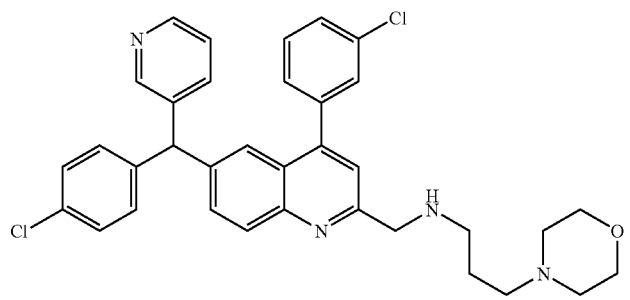
[B24] ms. 597 599 601

-continued
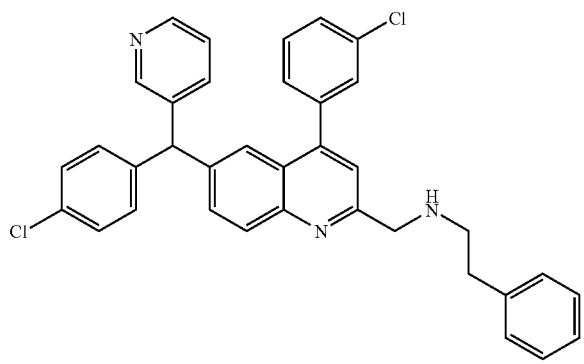
[B24] ms. 574 576 578
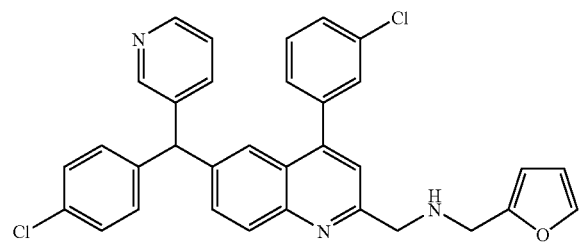
[B24] ms. 550 552 554
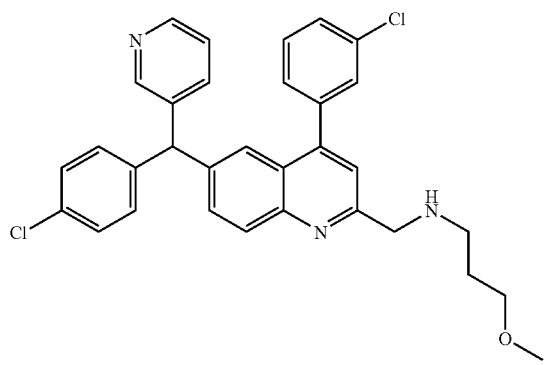
[B24] ms. 554 556 558
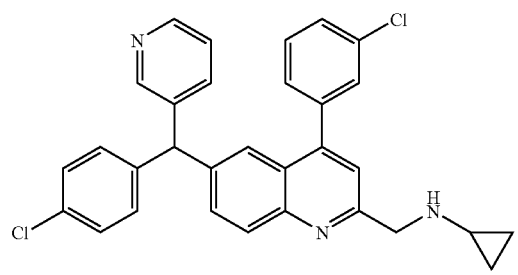
[B24] ms. 510 512 514

-continued
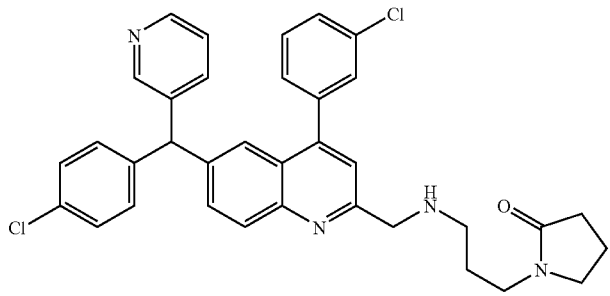
[B24] ms. 595 597 599
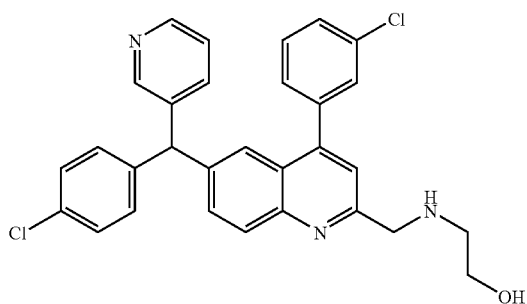
[B24] ms. 514 516 518
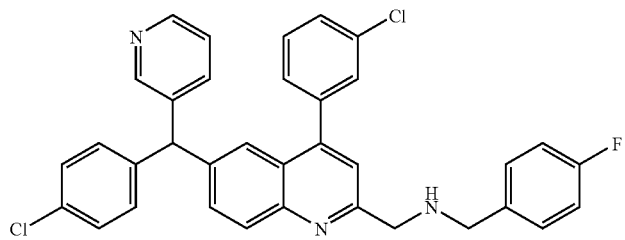
[B24] ms. 578 580 582
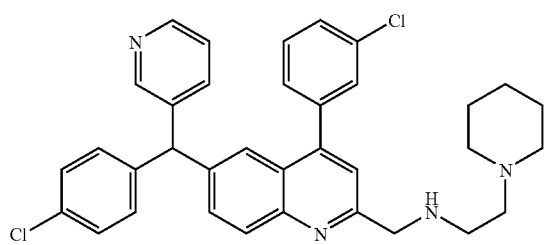
[B24] ms. 581 583 585
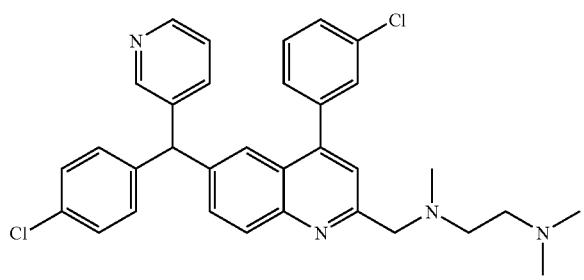
[B24] ms. 555 557 559

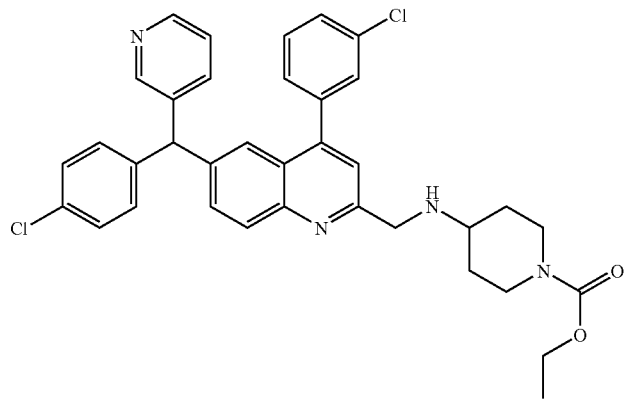
[B24] ms. 625 627 629
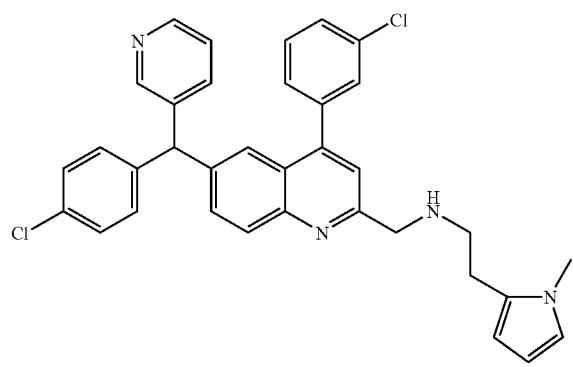
[B24] ms. 577 579 581
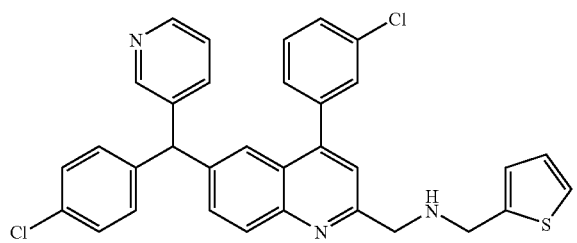
[B24] ms. 566 568 570
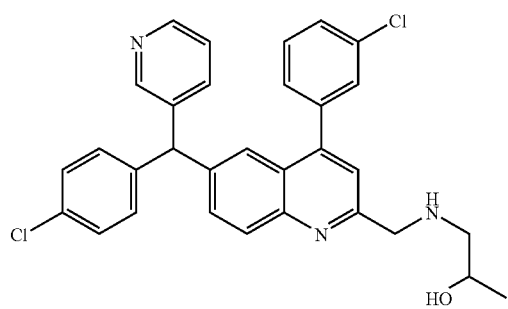
[B24] ms. 528 530 532

-continued
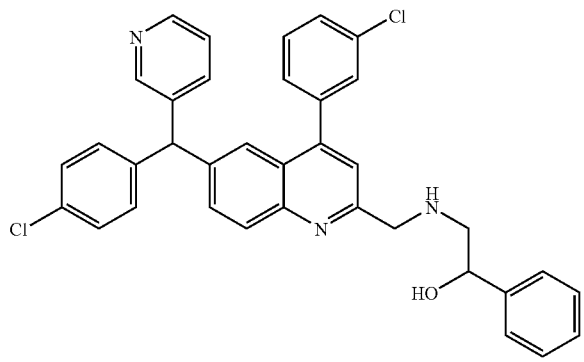
[B24] ms. 590 592 594
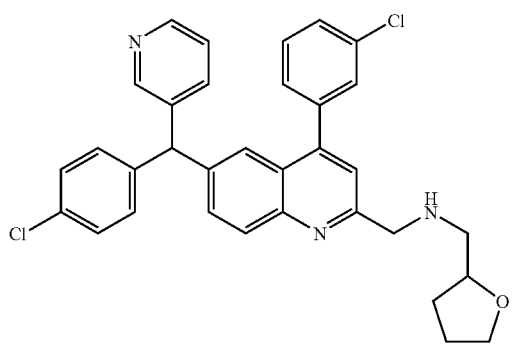
[B24] ms 554 556 558
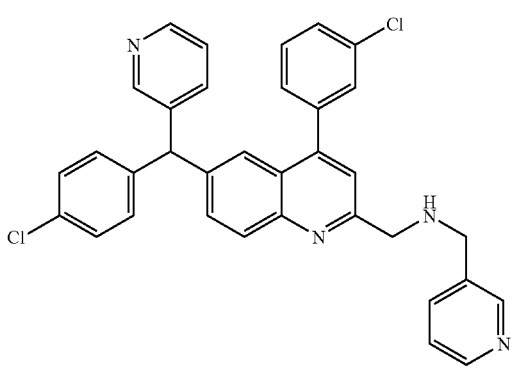
[B24] ms. 561 563 565
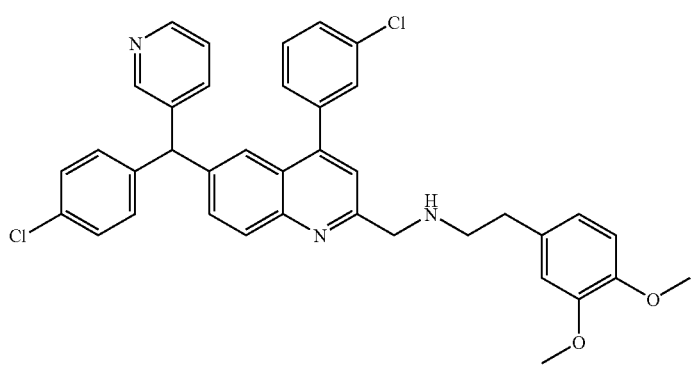
[B24] ms. 634 636 638

-continued

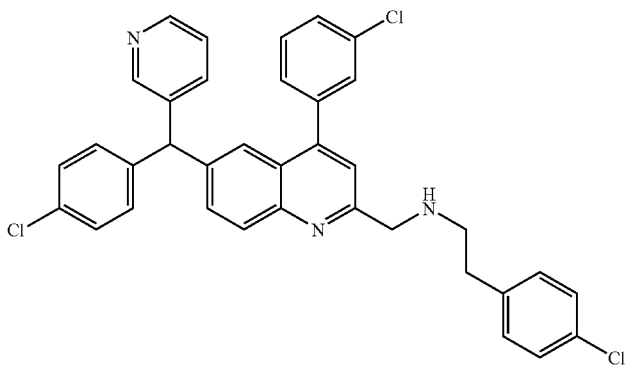

[B24] ms. 608 610 612 614

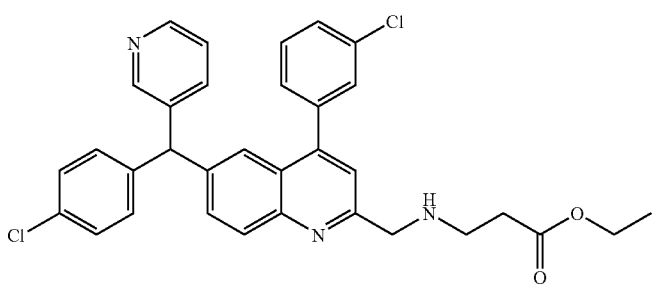

[B24] ms. 570 572 574

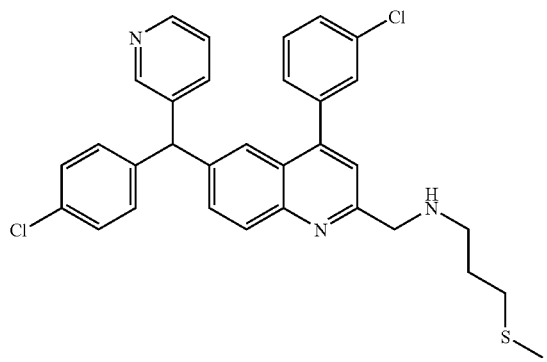

[B24] ms. 558 560 562

C. Pharmacological Examples

Example C.1

"In Vitro Assay for Inhibition of Farnesyl Protein Transferase":

An in vitro assay for inhibition of farnesyl transferase was performed essentially as described in WO 98/40383, pages 33–34.

Example C.2

"Ras-Transformed Cell Phenotype Reversion Assay".

The ras-transformed cell phenotype reversion assay was performed essentially as described in WO 98/40383, pages 34–36.

Example C.3

"Farnesyl Protein Transferase Inhibitor Secondary Tumor Model".

The farnesyl protein transferase inhibitor secondary tumor model was used as described in WO 98/40383, page 37.

D. Composition Example

Film-Coated Tablets

Preparation of Tablet Core

A mixture of 100 g of a compound of formula (I), 570 g lactose and 200 g starch is mixed well and thereafter humidified with a solution of 5 g sodium dodecyl sulfate and 10 g polyvinyl-pyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

The invention claimed is:

1. A compound of formula (I):

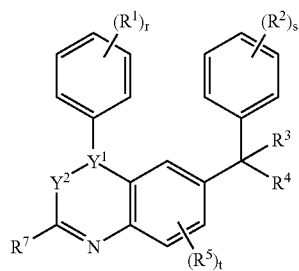

or a pharmaceutically acceptable salt or N-oxide or stereochemically isomeric form thereof, wherein r and s are each independently 0, 1, 2, 3, 4 or 5;
t is 0, 1, 2 or 3;
$>Y^1{-}Y^2{-}$ is a trivalent radical of formula $$>C{=}N{-} \quad (y\text{-}1)$$

$$>C{=}CR^9{-} \quad (y\text{-}2)$$

wherein $R^9$ is hydrogen, halo, cyano, $C_{1-6}$alkyl, hydroxyC$_{1-6}$alkyl, $C_{1-6}$alkyloxyC$_{1-6}$alkyl, $-(CR^{20}R^{21})_p-C_{3-10}$cycloalkyl, $C_{2-6}$alkenyl, $C_{2-6}$alkynyl, $C_{1-6}$alkyloxy, halocarbonyl, hydroxycarbonyl, $C_{1-6}$alkyloxycarbonyl, aryl or a group of formula $-NR^{22}R^{23}$, $-C_{1-6}$alkyl-NR$^{22}$R$^{23}$, $-C_{2-6}$alkenyl-NR$^{22}$R$^{23}$, $-CONR^{22}R^{23}$ or $-NR^{22}-C_{1-6}$alkyl-NR$^{22}$R$^{23}$;
p is 0 to 5;
$R^{20}$ and $R^{21}$ are independently hydrogen or $C_{1-6}$ alkyl and are independently defined for each iteration of p in excess of 1;
$R^{22}$ and $R^{23}$ are independently hydrogen, $C_{1-6}$ alkyl or $-(CR^{20}R^{21})_p-C_{3-10}$cycloalkyl, or together with the adjacent nitrogen atom form a 5- or 6-membered heterocyclic ring optionally containing one, two or three further heteroatoms selected from oxygen, nitrogen or sulphur and optionally substituted by one or two substituents each independently selected from halo, hydroxy, cyano, nitro, $C_{1-6}$alkyl, haloC$_{1-6}$alkyl, $C_{1-6}$alkyloxy, OCF$_3$, hydroxycarbonyl, $C_{1-6}$alkyloxycarbonyl, aminocarbonyl, mono- or di-(C$_{1-6}$alkyl)aminocarbonyl, amino, mono- or di(C$_{1-6}$alkyl)amino, $C_{1-4}$alkylsulfonylamino, oxime, or phenyl;
each $R^1$ and $R^2$ are independently azido, hydroxy, halo, cyano, nitro, $C_{1-4}$alkyl, $-(CR^{20}R^{21})_p-C_{3-10}$cycloalkyl, cyanoC$_{1-6}$alkyl, hydroxyC$_{1-6}$alkyl, $C_{1-6}$alkyloxyC$_{1-6}$alkyl, hydroxycarbonylC$_{1-6}$alkyloxyC$_{1-6}$alkyl, $R^{24}$S C$_{1-6}$alkyl, trihalomethyl, arylC$_{1-6}$alkyl, Het$^2$C$_{1-6}$alkyl, $-C_{1-6}$alkyl-NR$^{22}$R$^{23}$, $-C_{1-6}$alkylNR$^{22}$C$_{1-6}$alkyl-NR$^{22}$R$^{23}$, $-C_{1-6}$alkylNR$^{22}$COC$_{1-6}$alkyl, $-C_{1-6}$alkylNR$^{22}$COAlkAr$^2$, $-C_{1-6}$alkylNR$^{22}$COAr$^2$, $C_{1-6}$alkylsulphonylaminoC$_{1-6}$alkyl, $C_{1-6}$alkyloxy, hydroxyC$_{1-6}$alkyloxy, $C_{1-6}$alkyloxyC$_{1-6}$alkyloxy, $-OC_{1-6}$alkyl-NR$^{22}$R$^{23}$, trihalomethoxy, arylC$_{1-6}$alkyloxy, Het$^2$C$_{1-6}$alkyloxy, $C_{1-6}$alkylthio, $C_{2-6}$alkenyl, cyanoC$_{2-6}$alkenyl, $-C_{2-6}$alkenyl-NR$^{22}$R$^{23}$, hydroxycarbonylC$_{2-6}$alkenyl, $C_{1-6}$alkyloxycarbonylC$_{2-6}$alkenyl, $C_{2-6}$alkynyl, $-$CHO, $C_{1-6}$alkylcarbonyl, hydroxyC$_{1-6}$alkylcarbonyl, hydroxycarbonyl, $C_{1-6}$alkyloxycarbonyl, $-$CONR$^{22}$R$^{23}$, $-$CONR$^{22}-C_{1-6}$alkyl-NR$^{22}$R$^{23}$, $-$CONR$^{22}-C_{1-6}$alkyl-Het$^2$, $-$CONR$^{22}-C_{1-6}$alkyl-Ar$^2$, $-$CONR$^{22}-O-C_{1-6}$alkyl, $-$CONR$^{22}-C_{1-6}$alkenyl, $-NR^{22}R^{23}$, $-OC(O)R^{24}$, $-CR^{24}{=}NR^{25}$, $-CR^{24}{=}N-OR^{25}$, $-NR^{24}C(O)NR^{22}R^{23}$, $-NR^{24}SO_2R^{25}$, $-NR^{24}C(O)R^{25}$, $-S(O)_{0-2}R^{24}$, a $-SO_2NR^{24}R^{25}$, $-C(NR^{26}R^{27}){=}NR^{28}$; $-Sn(R^{24})_3$, $-SiR^{24}R^{24}R^{25}$, $-B(OR^{24})_2$, $-P(O)OR^{24}OR^{25}$, aryloxy, Het$^2$-oxy, or a group of formula $$-Z, \ -CO\text{-}Z \text{ or } -CO-NR^y\text{-}Z$$

in which $R^y$ is hydrogen or $C_{1-4}$alkyl and Z is phenyl or a 5- or 6-membered heterocyclic ring containing one or more heteroatoms selected from oxygen, sulphur and nitrogen, the phenyl or heterocyclic ring being optionally substituted by one or two substituents each independently selected from halo, cyano, hydroxycarbonyl, aminocarbonyl, $C_{1-6}$alkylthio, hydroxy, $-NR^{22}R^{23}$, $C_{1-6}$-alkylsulphonylamino, $C_{1-6}$alkyl, haloC$_{1-6}$alkyl, $C_{1-6}$alkyloxy or phenyl; or two $R^1$ and $R^2$ substituents adjacent to one another on the phenyl ring may independently form together a bivalent radical of formula $$-O-CH_2-O- \quad (a\text{-}1)$$

$$-O-CH_2-CH_2-O- \quad (a\text{-}2)$$

$$-O-CH{=}CH- \quad (a\text{-}3)$$

$$-O-CH_2-CH_2- \quad (a\text{-}4)$$

$$-O-CH_2-CH_2-CH_2- \quad (a\text{-}5)$$

$$-CH{=}CH-CH{=}CH- \quad (a\text{-}6)$$

$R^{24}$ and $R^{25}$ are independently hydrogen, $C_{1-6}$alkyl, $-(CR_{20}R_{21})p$-C$_{3-10}$cycloalkyl or arylC$_{1-6}$alkyl;
$R^{26}$, $R^{27}$ and $R^{28}$ are independently hydrogen and $C_{1-6}$alkyl or C(O) $C_{1-6}$alkyl;
$R^3$ is hydrogen, halo, cyano, $C_{1-6}$alkyl, $-(CR^{20}R^{21})_p-$C$_{3-10}$cycloalkyl, haloC$_{1-6}$alkyl, cyanoC$_{1-6}$alkyl, hydroxy C$_{1-6}$alkyl, $C_{1-6}$alkyloxyC$_{1-6}$alkyl, arylC$_{1-6}$alkyloxyC$_{1-6}$alkyl, $C_{1-6}$alkylthioC$_{1-6}$alkyl, hydroxycarbonylC$_{1-6}$alkyl, $C_{1-6}$alkylcarbonylC$_{1-6}$alkyl, $C_{1-6}$alkyloxycarbonylC$_{1-6}$alkyl, $C_{1-6}$alkyl-NR$^{22}$R$^{23}$, $C_{1-6}$alkyl-CONR$^{22}$R$^{23}$, arylC$_{1-6}$alkyl, Het$^2$C$_{1-6}$alkyl, $C_{2-6}$alkenyl, $-C_{2-6}$alkenyl NR$^{22}$R$^{23}$, $C_{2-6}$alkynyl, hydroxycarbonyl, $C_{1-6}$alkyloxycarbonyl, aryl, or Het$^2$; or a radical of formula $$-O-R^{10} \quad (b\text{-}1)$$

$$-S-R^{10} \quad (b\text{-}2)$$

$$-NR^{11}R^{12} \quad (b\text{-}3) \text{ or}$$

$$-N{=}CR^{10}R^{11} \quad (b\text{-}4)$$

wherein $R^{10}$ is hydrogen, $C_{1-6}$alkyl, $-(CR^{20}R^{21})_pC_{3-10}$ cycloalkyl, arylC$_{1-6}$alkyl, $C_{2-6}$alkenyl, $C_{2-6}$alkynyl, $C_{1-6}$alkylcarbonyl, aryl, a group of formula —NR$^{22}$R$^{23}$R or —C$_{1-6}$alkylC(O)OC$_{1-6}$alkyl NR$^{22}$R$^{23}$, or a radical of formula -Alk-OR$^{13}$ or -Alk-NR$^{14}$R$^{15}$;

R$^{11}$ is hydrogen, C$_{1-6}$alkyl, —(CR$^{20}$R$^{21}$)$_p$—C$_{3-10}$cycloalkyl, C$_{2-6}$alkenyl, C$_{2-6}$alkynyl, aryl or arylC$_{1-6}$alkyl;

R$^{12}$ is hydrogen, hydroxy, C$_{1-6}$alkyl, —(CR$^{20}$R$^{21}$)$_p$—C$_{3-10}$cycloalkyl, C$_{1-6}$alkylcarbonylC$_{1-6}$alkyl, arylC$_{1-6}$alkyl, C$_{2-6}$alkenyl, C$_{2-6}$alkynyl, aryl, C$_{1-6}$alkyloxy, a group of formula —NR$^{22}$R$^{23}$, C$_{1-6}$alkylcarbonylamino, C$_{1-6}$alkylcarbonyl, haloC$_{1-6}$alkylcarbonyl, arylC$_{1-6}$alkylcarbonyl, arylcarbonyl, C$_{1-6}$alkyloxycarbonyl, trihaloC$_{1-6}$alkyloxycarbonyl, C$_{1-6}$alkyloxyC$_{1-6}$alkylcarbonyl, aminocarbonyl, mono- or di(C$_{1-6}$alkyl)aminocarbonyl wherein the alkyl moiety may optionally be substituted by one or more substituents independently selected from aryl and C$_{1-6}$alkyloxycarbonyl substituents;

aminocarbonylcarbonyl, mono- or di(C$_{1-6}$alkyl)amino C$_{1-6}$alkylcarbonyl, or a radical of formula -Alk-OR$^{13}$ or Alk-NR$^{14}$R$^{15}$; wherein Alk is C$_{1-6}$alkanediyl;

R$^{13}$ is hydrogen, C$_{1-6}$alkyl, —(CR$^{20}$R$^{21}$)$_p$—C$_{3-10}$cycloalkyl, C$_{2-6}$alkenyl, C$_{2-6}$alkynyl, C$_{1-6}$alkylcarbonyl, hydroxyC$_{1-6}$alkyl, aryl or arylC$_{1-6}$alkyl;

R$^{14}$ is hydrogen, C$_{1-6}$alkyl, —(CR$^{20}$R$^{21}$)$_p$—C$_{3-10}$cycloalkyl, C$_{2-6}$alkenyl, C$_{2-6}$alkynyl, aryl or arylC$_{1-6}$alkyl;

R$^{15}$ is hydrogen, C$_{1-6}$alkyl, —(CR$^{20}$R$^{21}$)$_p$—C$_{3-10}$cycloalkyl, C$_{2-6}$alkenyl, C$_{2-6}$alkynyl, C$_{1-6}$alkylcarbonyl, aryl or arylC$_{1-6}$alkyl;

R$^4$ is a radical of formula

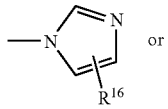

(c-1)

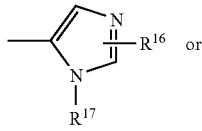

(c-2)

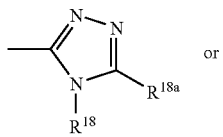

(c-3)

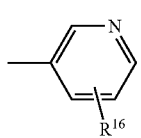

(c-4)

wherein R$^{16}$ is hydrogen, halo, C$_{1-6}$alkyl, —(CR$^{20}$R$^{21}$)$_p$—C$_{3-10}$cycloalkyl, hydroxyC$_{1-6}$alkyl, C$_{1-6}$alkyloxy C$_{1-6}$alkyl, C$_{1-6}$alkylS(O)$_{0-2}$C$_{1-6}$alkyl, C$_{1-6}$alkyloxy, C$_{1-6}$alkylthio, a group of formula —NR$^{22}$R$^{23}$, hydroxycarbonyl, C$_{1-6}$alkyloxycarbonyl or aryl, R$^{17}$ is hydrogen, C$_{1-6}$alkyl, —(CR$^{20}$R$^{21}$)$_p$—C$_{3-10}$cycloalkyl, hydroxyC$_{1-6}$alkyl, C$_{1-6}$alkyloxyC$_{1-6}$alkyl, aryl C$_{1-6}$alkyl, trifluoromethyl, trifluoromethylC$_{1-6}$alkyl, hydroxycarbonylCalkylC$_{1-6}$alkyloxycarbonylC$_{1-6}$alkyl, mono- or di (C$_{1-6}$alkyl)aminosulphonyl or —C$_{1-6}$alkyl P(O)OR$^{24}$OR$^{25}$;

R$^{18}$ is hydrogen, C$_{1-6}$alkyl, —(CR$^{20}$R$^{21}$)$_p$—C$_{3-10}$cycloalkyl, arylC$_{1-6}$alkyl or C$_{1-6}$alkyloxyC$_{1-6}$alkyl;

R$^{18a}$ is hydrogen, —SH or —SC$_{1-4}$alkyl

R$^5$ is cyano, hydroxy, halo, C$_{1-6}$alkyl, —(CR$^{20}$R$^{21}$)$_p$—C$_{3-10}$cycloalkyl , C$_{2-6}$alkenyl, C$_{2-6}$alkynyl, C$_{1-6}$alkyloxy, arylC$_{1-6}$alkyloxy, Het$^2$C$_{1-6}$alkyloxy, hydroxycarbonyl, C$_{1-6}$alkyloxycarbonyl, or a group of formula —NR$^{22}$R$^{23}$ or —CONR$^{22}$R$^{23}$;

R$^7$ is (A) a group selected from:

(A1) C$^{1-10}$alkyl, (A2) —(CR$^{20}$R$^{21}$)$_p$—C$_{3-10}$cycloalkyl, C$_{2-6}$alkenyl, or C$_{2-6}$alkynyl ; or (A3) C$_{1-6}$alkylthio, the groups (A1), (A2) and (A3) being optionally substituted by one or more substituents selected from:

(Aa) halo, cyano, —OR$^{29}$, COOR$^{29}$, —CONR$^{22}$R$^{23}$ , or —NR$^{22}$R$^{23}$; or (Ab) —OAlkNR$^{22}$R$^{23}$, —OAlkCONR$^{22}$R$^{23}$, —COOAlkAr$^2$, —NR$^{22}$Alk NR$^{22}$R$^{23}$, —NR$^{22}$AlkCN, —NR$^{22}$Alk-C$_{1-6}$hydroxyalkyl, —NR$^{22}$AlkOC$_{1-6}$alkyl, —NR$^{22}$AlkCOOC$_{1-6}$alkyl, —NR$^{22}$AlkSAlk-Ar$^2$, —NR$^{22}$Alk-Ar$^2$, —NR$^{22}$Alk-Het$^2$ or —NR$^{22}$ C$_{2-6}$alkenyl;

or R$^7$ is (B) a group selected from:

(B1) —COOR$^{29}$, —CHO, —COC$_{1-6}$alkyl, —CONR$^{22}$R$^{23}$, —NR$^{22}$R$^{23}$ or —NHCOC$_{1-15}$alkyl; or (B2) —COAlkAr$^2$, —COAlkHet$^2$, —CONR$^{22}$(CR$^{20}$R$^{21}$)$_p$—C$_{3-10}$cycloalkyl, —CONR$^{22}$C$_{2-6}$alkenyl, —CONR$^{22}$ Ar$^2$, —CONR$^{22}$Het$^2$, —CONR$^{22}$Alk NR$^{22}$R$^{23}$, —CONR$^{22}$ AlkAr$^2$, —CONR$^{22}$AlkHet$^2$, —NHCO(CR$^{20}$R$^{21}$)$_p$—C$_{3-10}$cycloalkyl, —NHCOC$_{2-10}$alkenyl, —NHCOAlkOC$_{1-6}$alkyl, —NHCOAlkOCOC$_{1-6}$alkyl, —NHCOAlkCOOC$_{1-6}$alkyl, —NHCOAr$^2$, —NHCOOAr$^2$, —NHCOAlkAr$^2$, —NHCOC$_{2-6}$alkenylAr$^2$, —NHCOAlkOAr$^2$, —NHCOAlkSAr$^2$, —NHCOHet$^2$, —NHCOAlkHet$^2$, —NHCO C$_{2-6}$alkenylHet$^2$, —NHCOAlkOHet$^2$, —NHCOAlkSHet$^2$, —NHCO NR$^{22a}$ R$^{23a}$, —NHCS NR$^{22a}$R$^{23a}$in which R$^{22a}$ and R$^{23a}$ represent groups represented by R$^{22}$ and R$^{23}$ above or in addition one or two groups selected from C$_{2-6}$ alkenyl, -AlkCOOC$_{1-6}$alkyl, Ar$^2$, Het$^2$, -AlkAr$^2$, -AlkHet$^2$, or —(CR$^{20}$R$^{21}$)$_p$—C$_{3-10}$cycloalkyl; and R$^{29}$ is hydrogen, C$_{1-6}$alkyl, Ar$^2$ C$_{1-6}$alkyl, Het$^2$ C$_{1-6}$alkyl; a group of formula —NR$^{24}$SO$_2$R$^{25}$; a group of formula —C(NR$^{26}$R$^{27}$)=NR$^{28}$; a group of formula —NH—NH—R$^{40}$ in which R$^{40}$ is Ar$^2$, Het$^2$, —C$_{1-6}$alkylAr$^2$, —C(O)Het$^2$, —C(O)Ar$^2$, —C(O)C$_{1-6}$alkyl, —C(O)C$_{1-6}$alkylAr$^2$, —C(O)NHAr2, —C(S)NHAr$^2$, —C(S)C$_{1-6}$alkyl, an oxime, C$_{1-6}$alkyl oxime or aryl C$_{1-6}$alkyl oxime group;

or R$^7$ is (C) a group of formula;

(C1)-Z-Ar$^2$ or -Z-Het$^2$, or (C2)-Z-O—Ar$^2$ or -Z-S—Ar$^2$ in which Z is (Ca) a chemical bond, or a C$_{1-6}$alkanediyl or C$_{2-6}$alkenediyl group optionally substituted by hydroxy, a group of formula —NR$^{22}$R$^{23}$, OR$^{24}$ or cyano; or (Cb) a carbonyl group;

Ar$^2$ is phenyl, naphthyl or phenyl or naphthyl substituted by one to five substituents each independently selected from halo, hydroxy, cyano, nitro, C$_{1-6}$alkyl, haloC$_{1-6}$alkyl, -alkylNR$^{22}$R$^{23}$, C$_{1-6}$alkyloxy, OCF$_3$, hydroxycarbonyl, C$_{1-6}$alkyloxycarbonyl, —CONR$^{22}$R$^{23}$, —NR$^{22}$R$^{23}$ , C$_{1-6}$alkylsulfonylamino, oxime or phenyl, or a bivalent substituent of formula —O—CH$_2$—O— or —O—CH$_2$—CH$_2$—O—;

Het$^2$ is a mono- or bi-cyclic heterocyclic ring containing one or more heteroatoms selected from oxygen, sulphur and nitrogen and optionally substituted by one or two substituents each independently selected from halo, hydroxy, cyano, nitro, C$_{1-6}$alkyl, haloC$_{1-6}$alkyl, -alkylNR$^{22}$R$^{23}$, C$_{1-6}$alkyloxy, OCF$_3$, hydroxycarbonyl, C$_{1-6}$alkyloxycarbonyl, —CONR$^{22}$R$^{23}$, —NR$^{22}$R$^{23}$, C$_{1-6}$alkylsulfonylamino, oxime or phenyl;

provided that (A) when r and s are each 1, t is 0, R$^1$ is 3-chloro, R$^2$ is 4-chloro, R$^3$ is hydroxy and R$^4$ is 1-methyl-1H-imidazol-5-yl, and (a) when >Y$^1$—Y$^2$ is a radical of formula (y-2), in which R$^9$ is hydrogen, then R$^7$ is not amino, methyl, —CHO or chloro, or (b) when >Y$^1$—Y$^2$ is a radical of formula (y-1), then R$^7$ is not chloro; and (B) when >Y$^1$—Y$^2$ is a radical of formula (y-2) and R$^4$ is a radical of formula (c-1), (c-2) or (c-4) then the group R$^7$ is (i) a group A1 substituted by substituents (Ab), a group (A2) substituted by substituents (Aa) (other than halo) or (Ab), or a group (A3) optionally substituted by substituents (Aa) or (Ab) as defined above; or (ii) a group (B2) as defined above; or (iii) a group(C1) in which Z is (Cb), or a group (C2) as defined above.

2. A compound of claim 1 wherein r and s are each independently 0, 1 or 2;

t is 0 or 1;

>Y$^1$—Y$^2$— is a trivalent radical of formula

>C=CR$^9$— (y-2)

wherein R$^9$ is hydrogen, cyano, halo, C$_{1-6}$alkyl, hydroxyC$_{1-6}$alkyl, hydroxycarbonyl or aminocarbonyl;

R$^1$ is halo, C$_{1-6}$alkyl, —(CR$^{20}$R$^{21}$)$_p$—C$_{3-10}$cycloalkyl, trihalomethyl, trihalomethoxy, C$_{2-6}$alkenyl, hydroxycarbonylC$_{2-6}$alkenyl, C$_{2-6}$alkynyl, C$_{1-6}$alkyloxy, hydroxyC$_{1-6}$alkyloxy, aminoC$_{1-6}$alkyloxy, C$_{1-6}$alkylthio, hydroxycarbonyl, C$_{1-6}$alkyloxycarbonyl, —CONR$^{22}$R$^{23}$, or —CH=NOR$^{25}$; or two R$^1$ substituents adjacent to one another on the phenyl ring may independently form together a bivalent radical of formula —O—CH$_2$—O— (a-1)

—O—CH$_2$—CH$_2$—O— (a-2)

R$^2$ is halo, cyano, nitro, cyanoC$_{1-6}$alkyl, C$_{1-6}$alkyl NR$^{22}$R$^{23}$; cyanoC$_{2-6}$alkenyl, —NR$^{22}$R$^{23}$, CHO, C$_{1-6}$alkyloxycarbonyl, —CO NR$^{22}$R$^{23}$; or two R$^2$ substituents adjacent to one another on the phenyl ring may independently form together a bivalent radical of formula —O—CH$_2$—O— (a-1)

—O—CH$_2$—CH$_2$—O— a-2)

R$^3$ is hydrogen, halo, C$_{1-6}$alkyl, —(CR$^{20}$R$^{21}$)$_p$—C$_{3-10}$cycloalkyl, haloC$_{1-6}$alkyl, cyanoC$_{1-6}$alkyl, hydroxyC$_{1-6}$alkyl, C$_{1-6}$alkyloxyC$_{1-6}$alkyl, —C$_{1-6}$alkyl NR$^{22}$R$^{23}$, Het$^2$C$_{1-6}$alkyl, —C$_{2-6}$alkenyl NR$^{22}$R$^{23}$, or -Het$^2$; or a group of formula —O—R$^{10}$ (b-1)

—NR$^{11}$R$^{12}$ (b-3)

wherein R$^{10}$ is hydrogen, C$_{1-6}$alkyl, or —(CR$^{20}$R$^{21}$)$_p$—C$_{3-1}$cycloalkyl, or a group of formula -Alk-OR$^{13}$ or -Alk-NR$^{14}$R$^{15}$;

R$^{11}$ is hydrogen or C$_{1-6}$alkyl;

R$^{12}$ is hydrogen, hydroxy, C$_{1-6}$alkyl, —(CR$^{20}$R$^{21}$)$_p$—C$_{3-10}$cycloalkyl, C$_{1-6}$alkyloxy, C$_{1-6}$alkylcarbonyl, aminocarbonyl, or a radical of formula -Alk-OR$^{13}$ or Alk-NR$^{14}$R$^{15}$;

wherein Alk is C$_{1-6}$alkanediyl;

R$^{13}$ is hydrogen, C$_{1-6}$alkyl or —(CR$^{20}$R$^{21}$)$_p$—C$_{3-10}$cycloalkyl;

R$^{14}$ is hydrogen, C$_{1-6}$alkyl, or —(CR$^{20}$R$^{21}$)$_p$—C$_{3-10}$cycloalkyl;

R$^{15}$ is hydrogen or C$_{1-6}$alkyl;

R$^4$ is a radical of formula (c-2) or (c-3) wherein R$^{16}$ is hydrogen, halo or Calkyl, R$^{17}$ is hydrogen, C$_{1-6}$alkyl, —(CR$^{20}$R$^{21}$)$_p$—C$_{3-10}$cycloalkyl, C$_{1-6}$alkyloxy-C$_{1-6}$alkyl or trifluoromethyl;

R$^{18}$ is hydrogen, C$_{1-6}$alkyl or —(CR$^{20}$R$^{21}$)$_p$—C$_{3-10}$cycloalkyl; R$^{16a}$ is hydrogen;

R$^5$ is cyano, halo, C$_{1-6}$alkyl, C$_{2-6}$alkynyl, C$_{1-6}$alkyloxy or C$_{1-6}$alkyloxycarbonyl;

R$^7$ is a C$_{1-10}$alkyl, C$_{2-6}$alkenyl or C$_{2-6}$alkynyl group or a C$_{1-10}$alkyl, C$_{2-6}$alkenyl or C$_{2-6}$alkynyl group substituted by one or more substituents selected from cyano , —OR$^{29}$, —COOR$^{25}$ and —CONR$^{22}$R$^{23}$, —NR$^{22}$Alk NR$^{22}$R$^{23}$, —NR$^{22}$ C$_{2-6}$alkenyl; or a group of formula:

—COOR$^{29}$, —CONR$^{22}$R$^{23}$, —CONR$^{22}$—(CR$^{20}$R$^{21}$)$_p$—C$_{3-10}$cycloalkyl, —CONR$^{22}$C$_{2-6}$alkenyl, —CONR$^{22}$Het$^2$, —CONR$^{22}$Alk —NR$^{22}$R$^{23}$, —NH-COC$_{1-6}$alkyl, —NHCOHet$^2$ or —NHCOAlkHet$^2$;

Het$^2$ is a 5- or 6-membered monocyclic heterocyclic ring containing one, two or three heteroatoms selected from oxygen, sulphur or nitrogen for example pyrrolidinyl, imidazolyl, triazolyl, pyridyl, pyrimidinyl, furyl, morpholinyl, piperazinyl, piperidinyl, thiophenyl, thiazolyl or oxazolyl, or a 9- or 10-membered bicyclic heterocyclic ring especially one in which a benzene ring is fused to a heterocyclic ring containing one, two or three heteroatoms selected from oxygen, sulphur or nitrogen for example indolyl, quinolinyl, benzimidazolyl, benzotriazolyl, benzoxazolyl, benzothiazolyl or benzodioxolanyl.

3. A compound of claim 1 wherein >Y$^1$—Y$^2$— is a trivalent radical of formula (y-2), wherein R$^9$ is hydrogen, halo, C$_{1-4}$alkyl, hydroxycarbonyl, or C$_{1-4}$alkyloxycarbonyl;

r is 0, 1 or 2; s is 0 or 1; t is 0;

R$^1$ is halo, C$_{1-6}$alkyl or two R$^1$ substituents ortho to one another on the phenyl ring may independently form together a bivalent radical of formula (a-1);

R$^2$ is halo, cyano, nitro, CHO, oxime, or two R$^2$ substituents ortho to one another on the phenyl ring may independently form together a bivalent radical of formula (a-1);

R$^3$ is halo, Het$^2$ or a group of formula (b-1) or (b-3) wherein R$^{10}$ is hydrogen or a group of formula -Alk-OR$^{13}$;

R$^{11}$ is hydrogen;

R$^{12}$ is hydrogen, C$_{1-6}$alkyl, C$_{1-6}$alkylcarbonyl, hydroxy, C$_{1-6}$alkyloxy or mono- or di(C$_{1-6}$alkyl)aminoC$_{1-6}$alkylcarbonyl;

Alk is C$_{1-6}$alkanediyl and R$^{13}$ is hydrogen;

R$^4$ is a group of formula (C-2) or (c-3) wherein R$^{16}$ is hydrogen, halo or mono- or di(C$_{1-4}$alkyl)amino;

R$^{17}$ is hydrogen or C$_{1-6}$alkyl;

R$^{18}$ is hydrogen or C$_{1-6}$alkyl;

R$^{8a}$ is hydrogen;

R$^7$ is a C$_{1-10}$alkyl group or a C$_{1-10}$alkyl group substituted by amino, —NR$^{22}$Alk NR$^{22}$R$^{23}$ or —NR$^{22}$ C$_{2-6}$alkenyl; or R$^7$ is C$_{2-6}$alkenyl, COOR$^{29}$, —CONR$^{22}$R$^{23}$, —CONR$^{22}$Het$^2$, —CONR$^{22}$ C$_{18}$alkyl Het$^2$, —CONR$^{22}$(CR$^{20}$R$^{21}$)$_p$—C$_{3-10}$cycloalkyl, —NHCOC$_{1-6}$alkyl or Z-Het$^2$ where Z is a carbonyl group; and aryl is phenyl.

4. A compound of claim 1 wherein >Y$^1$—Y$^2$ is a trivalent radical of formula (y-2), r is 0 or 1, s is 1, t is 0, R$^1$ is halo, C$_{(1-4)}$alkyl or forms a bivalent radical of formula (a-1), R$^2$ is halo, cyano or C$_{1-4}$alkyl, R$^3$ is hydrogen or a radical of formula (b-1) or (b-3), $R^{10}$ is hydrogen or -Alk-$OR^{13}$, $R^{11}$ is hydrogen and $R^{12}$ is hydrogen or $C_{1-6}$alkylcarbonyl and $R^{13}$ is hydrogen; $R^4$ is a radical of formula (c-2) or (c-3), wherein $R^{16}$ is hydrogen, $R^{17}$ is $C_{1-6}$alkyl, $R^{18}$ is $C_{1-6}$alkyl, $R^{18a}$ is hydrogen;

and $R^7$ is a $C^{1-10}$alkyl or $C_{2-6}$alkenyl group or a $C_{1-10}$alkyl or $C_{2-6}$alkenyl group substituted by one or more substituents selected from: $-NR^{22}R^{23}$, $-NR^{22}$Alk $NR^{22}R^{23}$ and $-NR^{22}$ $C_{2-6}$alkenyl;

or $R^7$ is substitutent selected from the group consisting of $-COOR^{29}$, $-CO\ NR^{22}R^{23}$, $-CONR^{22}(CR^{20}R^{21})_g-C_{3-10}$cycloalkyl, $-CONR^{22}$ $C_{2-6}$alkenyl, $-CONR^{22}$ $Ar^2$, $-CONR^{22}Het^2$, $-CONR^{22}$Alk $NR^{22}R^{23}$, $-CONR^{22}$AlkAr$^2$, $-CONR^{22}$AlkHet$^2$ or $-NHCOC_{1-10}$alkyl;

or a group of formula -Z-Het$^2$ in which Z is a chemical bond or a carbonyl group.

5. A compound of claim 1 wherein >$Y^1$—$Y^2$ is a trivalent radical of formula (y-2), r is 0 or 1, s is 1, t is 0, $R^1$ is halo, preferably chloro and most preferably 3-chloro, $R^2$ is halo, preferably 4-chloro or 4-fluoro, or cyano, preferably 4-cyano, $R^3$ is hydrogen or a radical of formula (b-1) or (b-3), $R^9$ is hydrogen, $R^{10}$ is hydrogen, $R^{11}$ is hydrogen and $R^{12}$ is hydrogen, $R^4$ is a radical of formula (c-2) or (c-3), wherein $R^{16}$ is hydrogen, $R^{17}$ is $C_{1-6}$alkyl, $R^{18}$ is $C_{1-6}$alkyl, $R^{18a}$ is hydrogen; and $R^7$ is a substituents selected from the group consisting of $-COOR^{29}$; $-CONR^{22}R^{23}$; $-CONR^{22}(CR^{20}R^{21})_g-C_{3-10}$cycloalkyl; $-CONR^{22}$ $C_{2-6}$alkenyl ; $-CONR^{22}$Alk $NR^{22}R^{23}$; or a group of formula -Z-Het$^2$ in which Z is a chemical bond or a carbonyl group.

6. A compound of claim 1 wherein >$Y^1$—$Y^2$ is a trivalent radical of formula (y-2), r and s are 1, t is 0, $R^1$ is halo, preferably chloro, and most preferably 3-chloro or $R^1$ is $C_{1-6}$alkyl, preferably 3-methyl, $R^2$ is halo, preferably chloro, and most preferably 4-chloro, or cyano, preferably 4-cyano, $R^3$ is a radical of formula (b-1) or (b-3), $R^9$ is hydrogen, $R^{10}$ and $R^{11}$ are hydrogen and $R^{12}$ is hydrogen or hydroxy, $R^4$ is a radical of formula (c-2) or (c-3), wherein $R^{16}$ is hydrogen, $R^{17}$ is $C_{1-6}$alkyl preferably methyl, $R^{18}$ is $C_{1-6}$alkyl preferably methyl, $R^{16}$ is hydrogen; and $R^7$ is selected from hydroxycarbonyl, aminocarbonyl, methylaminocarbonyl, n-propylaminocarbonyl, n-butylam inocarbonyl, cyclopropylaminocarbonyl, prop-1-en-2-ylaminocarbonyl, 1-ethoxycarbonyl-piperidin-4-ylaminocarbonyl, dimethylaminoethylaminocarbonyl, 4-morpholinylethylaminocarbonyl, 4-methylpiperazinylcarbonyl or 3-pyridyl.

7. A compound of claim 1 selected from the group consisting of (±)-4-(3-chlorophenyl)-α-(4-chlorophenyl)-α-(1-methyl-1H-imidazol-5-yl)-2-[(2-propenylamino)methyl]-6-quinolinemethanol, (±)-4-(3-chlorophenyl)-α-(4-chlorophenyl)-2-[[[2—(diethylamino)ethyl]amino]methyl]-α-(1-methyl-1H-imidazol-5-yl)-6-quinolinemethanol, (±)-4-(3-chlorophenyl)-α-(4-chlorophenyl)-α-(1-methyl-1H-imidazol-5-yl)-2-[[[2-(1-pyrrolidinyl)ethyl]amino]methyl]-6-quinolinemethanol, (±)-4-(3-chlorophenyl)-6-[(4-chlorophenyl)(1-methyl-1H-imidazol-5-yl)methyl]-N-(2-propenyl)-2-quinolinecarboxamide, (±)-4-(3-chlorophenyl)-6-[(4-chlorophenyl)(1-methyl-1H-imidazol-5-yl)methyl]-N-[2-(dimethylamino)ethyl]-2-quinolinecarboxamide, (±)-4-(3-chlorophenyl)-6-[(4-chlorophenyl)(1-methyl-1H-imidazol-5-yl)methyl]-N-[2-(4-morpholinyl)ethyl]-2-quinolinecarboxamide, (±)-ethyl 4-[[[4-(3-chlorophenyl)-6-[(4-chlorophenyl)(1-methyl-1H-imidazol-5-yl)methyl]-2-quinolinyl]carbonyl]amino]-1-piperidinecarboxylate, (±)-1-[4-(3-chlorophenyl)-6-[(4-chlorophenyl)(1-methyl-1H-imidazol-5-yl)methyl]-2-quinolinylcarbonyl]piperidine, (±)-1-[4-(3-chlorophenyl)-6-[(4-chlorophenyl)(1-methyl-1H-imidazol-5-yl)methyl]-2-quinolinecarbonyl]-4-methylpiperazine, (±)-4-(3-chlorophenyl)-6-[(4-chlorophenyl)(1-methyl-1H-imidazol-5-yl)methyl]-N-(2-furanylmethyl)-2-quinolinecarboxamide, (±)-4-(3-chlorophenyl)-6-[(4-chlorophenyl)(1-methyl-1H-imidazol-5-yl)methyl]-N-cyclopropyl-2-quinolinecarboxamide, (±)-4-(3-chlorophenyl)-6-[(4-chlorophenyl)(1-methyl-1H-imidazol-5-yl)methyl]-N-[2-(1-pyrrolidinyl)ethyl]-2-quinolinecarboxamide, (±)-4-(3-chlorophenyl)-6-[(4-chlorophenyl)(1-methyl-1H-imidazol-5-yl)methyl]-N-(4-pyridinylmethyl)-2-quinolinecarboxamide, (±)-4-(3-chlorophenyl)-α-(4-chlorophenyl)-2-methyl-α-(4-methyl-4H-1,2,4-triazol-3-yl)-6-quinolinemethanamine, (±)-4-(3-chlorophenyl)-α-(4-chlorophenyl)-2-methyl-α-(1-methyl-1H-imidazol-5-yl)-6-quinazolinemethanol, (±)-4-(3-chlorophenyl)-α-(4-chlorophenyl)-2-methyl-α-(4-methyl-4H-1,2,4-triazol-3-yl)-6-quinolinemethanol, and (±)-2-amino-4-(3-chlorophenyl)-α-(4-chlorophenyl)-α-(1-methyl-1H-imidazol-5-yl)-6-quinazolinemethanol, and their pharmaceutically acceptable salts.

8. A process for preparing a compound of claim 1 comprising cyclising a compound of formula (II):

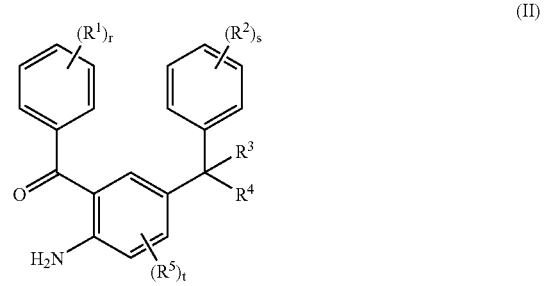

with (i) a compound of formula (III):

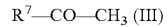

$R^7$—CO—$CH_3$ (III)

or (ii) a compound of formula $R^9CH_2CN$ to form a compound of formula (I) in which $R^7$ is amino and $R^9$ is hydrogen, $C_{1-6}$alkyl or aryl.

9. A process for preparing a compound of claim 1 comprising reacting a compound of formula (IV):

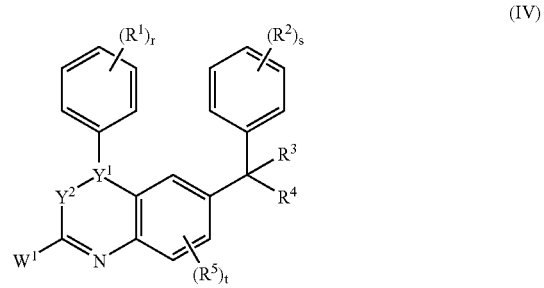

in which $W^1$ represents a replaceable or reactive group, with a reagent serving either to replace the $W^1$ group in compound (IV) with an $R^7$ group or to react with the $W^1$ group to form an $R^7$ group.

10. A process for preparing a compound of claim 1 consisting of reacting a compound of formula (V):

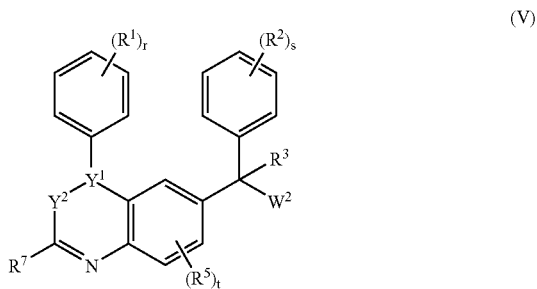

(V)

in which W2 is a replaceable group, with an imidazole reagent serving to replace the group $W^2$ with an $R^4$ group of formula (c-1).

11. A process for preparing a compound of claim 1 comprising reacting a compound of formula (VI):

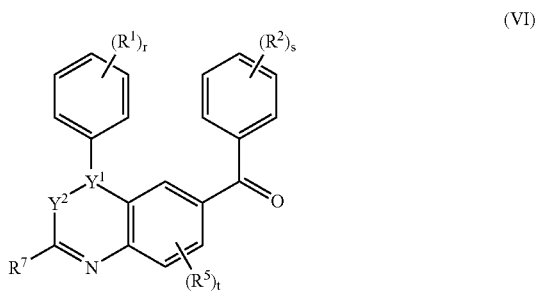

(VI)

with an imidazole reagent to form a compound of formula (I) in which $R^4$ is a group of formula (c-2), or with a 3-mercapto-4-methyl-1,2,4-triazole reagent to form a compound of formula (I) in which $R^4$ is a group of formula (c-3).

12. A method for inhibiting tumor growth comprising administering an effective amount of a compound of claim 1 to a subject in need of such treatment.

13. A pharmaceutical composition comprising a pharmaceutically acceptable carrier, and an active ingredient comprising a therapeutically effective amount of a compound of claim 1.

14. A pharmaceutical composition comprising a pharmaceutically acceptable carrier, and an active ingredient comprising a therapeutically effective amount of a compound of claim 2.

15. A pharmaceutical composition comprising a pharmaceutically acceptable carrier, and an active ingredient comprising a therapeutically effective amount of a compound of claim 3.

16. A pharmaceutical composition comprising a pharmaceutically acceptable carrier, and an active ingredient comprising a therapeutically effective amount of a compound of claim 4.

17. A pharmaceutical composition comprising a pharmaceutically acceptable carrier, and an active ingredient comprising a therapeutically effective amount of a compound of claim 5.

18. A pharmaceutical composition comprising a pharmaceutically acceptable carrier, and an active ingredient comprising a therapeutically effective amount of a compound of claim 6.

19. A pharmaceutical composition comprising a pharmaceutically acceptable carrier, and an active ingredient comprising a therapeutically effective amount of a compound of claim 7.

* * * * *